US007189201B2

(12) United States Patent
Borst et al.

(10) Patent No.: US 7,189,201 B2
(45) Date of Patent: *Mar. 13, 2007

(54) METHOD AND APPARATUS FOR TEMPORARILY IMMOBILIZING A LOCAL AREA OF TISSUE

(75) Inventors: Cornelius Borst, Bilthoven (NL); Hendricus J. Mansvelt Beck, Bilthoven (NL); Paul F. Grundeman, Amsterdam (NL); Cornelis Wilhelmus Jozef Verlaan, Soest (NL)

(73) Assignee: Medtronic, Inc., Minneapolis, MN (US)

( * ) Notice: Subject to any disclaimer, the term of this patent is extended or adjusted under 35 U.S.C. 154(b) by 214 days.

This patent is subject to a terminal disclaimer.

(21) Appl. No.: 10/137,159

(22) Filed: Apr. 30, 2002

(65) Prior Publication Data

US 2003/0078470 A1 Apr. 24, 2003
US 2004/0260145 A9 Dec. 23, 2004

Related U.S. Application Data

(60) Continuation of application No. 09/678,203, filed on Oct. 2, 2000, which is a continuation-in-part of application No. 09/493,466, filed on Jan. 28, 2000, now Pat. No. 6,371,906, which is a division of application No. 09/334,531, filed on Jun. 16, 1999, now Pat. No. 6,364,826, which is a division of application No. 08/725,371, filed on Oct. 3, 1996, now Pat. No. 6,015,378, which is a continuation-in-part of application No. 08/531,363, filed on Sep. 20, 1995, now Pat. No. 5,836,311.

(51) Int. Cl.
*A61F 2/00* (2006.01)
*A61F 13/00* (2006.01)
*A47J 45/00* (2006.01)
*A61B 19/00* (2006.01)

(52) U.S. Cl. .................. 600/37; 128/897; 128/898; 294/64.1

(58) Field of Classification Search .................. None
See application file for complete search history.

(56) References Cited

U.S. PATENT DOCUMENTS 452,131 A 5/1891 Haughawout (Continued)

FOREIGN PATENT DOCUMENTS

DE 9004513.0 4/1990

(Continued)

OTHER PUBLICATIONS

Mammary Artery-Coronary Artery Anastomosis as Method of Treatment for Angina Pectoris, V.I Kolessov, MD/Thoracic and Cardiovascular Surgery, vol. 54, No. 4, Oct. 1967 pp. 535-544.

(Continued)

*Primary Examiner*—Robert L. Nasser
(74) *Attorney, Agent, or Firm*—Mike Jaro; Jeffrey J. Hohenshell

(57) ABSTRACT

A method and apparatus for temporarily immobilizing a local area of tissue. In particular, the present invention provides a method and apparatus for temporarily immobilizing a local area of tissue within a patient's body cavity. In one embodiment, the tissue immobilized is heart tissue to thereby permit surgery on a coronary vessel in that area without significant deterioration of the pumping function of the beating heart. The local area of heart tissue is immobilized to a degree sufficient to permit minimally invasive or micro-surgery on that area of the heart. The apparatus for temporarily immobilizing a local area of tissue includes a first tissue engaging member and a second tissue engaging member coupled to a spreader The spreader is operated by an actuator to selectively control the movement of the first tissue engager and the second tissue engager The method for temporarily immobilizing a local area of tissue includes controlling the spreading of the first tissue engaging member and the second tissue engaging member so a selective amount of spreading occurs.

114 Claims, 32 Drawing Sheets

U.S. PATENT DOCUMENTS

| | | | |
|---|---|---|---|
| 2,590,527 A | 3/1952 | Fluck | 123/67 |
| 3,577,982 A | 5/1971 | La Par | 128/2 R |
| 3,720,433 A | 3/1973 | Rosfelder | 294/64 R |
| 3,783,873 A | 1/1974 | Jacobs | 128/303 R |
| 3,786,815 A | 1/1974 | Ericson | 128/321 |
| 3,858,926 A | 1/1975 | Ottenhues | 294/64 R |
| 3,916,909 A | 11/1975 | Kletschka et al. | 128/54 |
| 3,951,138 A | 4/1976 | Akopov | 128/17 |
| 3,983,863 A | 10/1976 | Janke et al. | 128/1 R |
| 3,999,795 A | 12/1976 | Barker | 294/64 R |
| 4,047,532 A | 9/1977 | Phillips et al. | 128/303 R |
| 4,049,000 A | 9/1977 | Williams | 128/276 |
| 4,049,002 A | 9/1977 | Kletschka et al. | 128/318 |
| 4,096,864 A | 6/1978 | Kletschka et al. | 128/354 |
| 4,306,561 A | 12/1981 | De Medinaceli | 128/303.13 |
| 4,314,568 A | 2/1982 | Loving | 128/327 |
| 4,350,160 A | 9/1982 | Kolesov et al. | 128/334 R |
| 4,366,819 A | 1/1983 | Kaster | 128/334 C |
| 4,368,736 A | 1/1983 | Kaster | 128/334 C |
| 4,428,368 A | 1/1984 | Torii | 128/38 |
| 4,447,227 A | 5/1984 | Kotsanis | 604/95 |
| 4,463,980 A | 8/1984 | Orii | 294/64 R |
| 4,627,421 A | 12/1986 | Symbas et al. | 128/20 |
| 4,637,377 A | 1/1987 | Loop | 128/1 R |
| 4,646,747 A | 3/1987 | Lundbäck | 128/643 |
| 4,653,636 A * | 3/1987 | Armstrong | 206/711 |
| 4,688,570 A | 8/1987 | Kramer et al. | 128/305 |
| 4,711,247 A | 12/1987 | Fishman | 128/743 |
| 4,718,418 A | 1/1988 | L'Esperance, Jr. | 128/303.1 |
| 4,726,356 A | 2/1988 | Santilli et al. | 128/20 |
| 4,736,749 A | 4/1988 | Lundback | 128/643 |
| 4,767,142 A | 8/1988 | Takahashi et al. | 294/64.1 |
| 4,808,163 A | 2/1989 | Laub | 604/105 |
| 4,852,552 A | 8/1989 | Chaux | 128/20 |
| 4,854,318 A | 8/1989 | Solem et al. | 128/346 |
| 4,865,019 A | 9/1989 | Phillips | 128/20 |
| 4,892,343 A | 1/1990 | Hall | 294/64.1 |
| 4,904,012 A | 2/1990 | Nishiguchi et al. | 294/64 |
| 4,925,443 A | 5/1990 | Heilman et al. | 600/16 |
| 4,955,896 A | 9/1990 | Freeman | 606/210 |
| 4,962,758 A | 10/1990 | Lasner et al. | 128/41 |
| 4,973,300 A | 11/1990 | Wright | 600/37 |
| 4,989,587 A | 2/1991 | Farley | 128/20 |
| 4,991,578 A | 2/1991 | Cohen | 128/419 D |
| 5,009,660 A | 4/1991 | Clapham | 606/166 |
| 5,011,469 A | 4/1991 | Buckberg et al. | 604/4 |
| 5,053,041 A | 10/1991 | Ansari et al. | 606/148 |
| 5,098,369 A | 3/1992 | Heilman et al. | 600/16 |
| 5,108,412 A | 4/1992 | Krumeich et al. | 606/166 |
| 5,119,804 A | 6/1992 | Anstadt | 12/64 |
| 5,131,905 A | 7/1992 | Grooters | 600/16 |
| 5,133,737 A | 7/1992 | Grismer | 606/205 |
| 5,167,223 A | 12/1992 | Koros et al. | 128/20 |
| 5,171,254 A | 12/1992 | Sher | 606/166 |
| 5,207,467 A | 5/1993 | Smith | 294/64.1 |
| 5,287,861 A | 2/1994 | Wilk | 128/898 |
| 5,290,082 A | 3/1994 | Palmer et al. | 294/64.1 |
| 5,300,087 A | 4/1994 | Knoepfler | 606/207 |
| 5,324,087 A | 6/1994 | Shimose et al. | 294/64.1 |
| 5,336,252 A | 8/1994 | Cohen | 607/119 |
| 5,365,921 A | 11/1994 | Bookwalter et al. | 128/20 |
| 5,372,124 A | 12/1994 | Takayama et al. | 128/4 |
| 5,374,277 A | 12/1994 | Hassler | 606/205 |
| 5,383,840 A | 1/1995 | Heilman et al. | 600/17 |
| 5,417,709 A | 5/1995 | Slater | 606/205 |
| 5,425,705 A | 6/1995 | Evard et al. | 604/28 |
| 5,437,651 A | 8/1995 | Todd et al. | 604/313 |
| 5,452,733 A | 9/1995 | Sterman et al. | 128/898 |
| 5,472,438 A | 12/1995 | Schmit et al. | 606/1 |
| 5,503,617 A | 4/1996 | Jako | 600/201 |
| 5,509,890 A | 4/1996 | Kazama | 600/37 |
| 5,545,123 A | 8/1996 | Oritz et al. | 600/235 |
| 5,556,147 A | 9/1996 | Somekh et al. | 294/64.1 |
| 5,582,580 A * | 12/1996 | Buckman et al. | 601/41 |
| 5,607,421 A | 3/1997 | Jeevanandam et al. | 606/15 |
| 5,613,937 A | 3/1997 | Garrison et al. | 600/201 |
| 5,667,624 A | 9/1997 | Akimoto et al. | 156/389 |
| 5,702,420 A | 12/1997 | Sterling et al. | 606/205 |
| 5,727,569 A | 3/1998 | Benetti et al. | 128/898 |
| 5,730,757 A | 3/1998 | Benetti et al. | 606/198 |
| 5,749,892 A | 5/1998 | Vierra et al. | 600/204 |
| 5,772,583 A | 6/1998 | Wright et al. | 600/232 |
| 5,782,746 A | 7/1998 | Wright | 600/37 |
| 5,799,661 A * | 9/1998 | Boyd et al. | 128/898 |
| 5,807,243 A | 9/1998 | Vierra et al. | 600/204 |
| 5,827,216 A | 10/1998 | Igo et al. | 604/21 |
| 5,836,311 A | 11/1998 | Borst et al. | 128/897 |
| 5,875,782 A | 3/1999 | Ferrari et al. | 128/898 |
| 5,888,247 A | 3/1999 | Benetti | 623/66 |
| 5,894,843 A | 4/1999 | Benetti et al. | 128/898 |
| 5,906,607 A | 5/1999 | Taylor et al. | 606/1 |
| 5,921,979 A | 7/1999 | Kovac et al. | 606/1 |
| 5,927,284 A | 7/1999 | Borst et al. | 128/898 |
| 5,947,896 A | 9/1999 | Sherts et al. | 600/229 |
| 5,976,080 A | 11/1999 | Farascioni | 600/213 |
| 5,976,171 A | 11/1999 | Taylor | 606/198 |
| 6,015,378 A | 1/2000 | Borst et al. | 600/37 |
| 6,017,304 A | 1/2000 | Vierra et al. | 600/204 |
| 6,019,722 A | 2/2000 | Spence et al. | 600/210 |
| 6,032,672 A | 3/2000 | Taylor | 128/898 |
| 6,050,266 A | 4/2000 | Benetti et al. | 128/898 |
| 6,063,021 A | 5/2000 | Hossain et al. | 600/37 |
| 6,071,235 A | 6/2000 | Furnish et al. | 600/235 |
| 6,074,375 A | 6/2000 | Stiles | 604/268 |
| 6,110,187 A | 8/2000 | Donlon | 606/151 |
| 6,132,370 A | 10/2000 | Furnish et al. | 600/235 |
| 6,139,492 A | 10/2000 | Vierra et al. | 600/204 |
| 6,149,583 A | 11/2000 | Vierra et al. | 600/204 |
| 6,152,874 A | 11/2000 | Looney et al. | 600/214 |
| 6,183,486 B1 | 2/2001 | Snow et al. | 606/151 |
| 6,206,827 B1 | 3/2001 | Chin et al. | 600/217 |
| 6,213,941 B1 | 4/2001 | Benetti et al. | 600/235 |
| 6,254,535 B1 | 7/2001 | Furnish et al. | 600/213 |
| 6,290,644 B1 | 9/2001 | Green, II et al. | 600/235 |
| 6,306,085 B1 | 10/2001 | Farascioni | 600/213 |
| 6,315,717 B1 | 11/2001 | Benetti et al. | 600/210 |
| 6,328,688 B1 | 12/2001 | Borst et al. | 600/37 |
| 6,334,843 B1 | 1/2002 | Borst et al. | 600/37 |
| 6,336,898 B1 * | 1/2002 | Borst et al. | 600/37 |
| 6,346,077 B1 | 2/2002 | Taylor et al. | 600/204 |
| 6,350,229 B1 | 2/2002 | Borst et al. | 600/37 |
| 6,364,826 B1 * | 4/2002 | Borst et al. | 600/37 |
| 6,371,906 B1 | 4/2002 | Borst et al. | 600/37 |
| 6,379,297 B1 | 4/2002 | Furnish et al. | 600/213 |
| 6,394,948 B1 | 5/2002 | Borst et al. | 600/37 |
| 6,394,951 B1 | 5/2002 | Taylor et al. | 600/210 |
| 6,447,443 B1 * | 9/2002 | Keogh et al. | 600/37 |
| 6,464,629 B1 * | 10/2002 | Boone et al. | 600/37 |
| 6,581,889 B2 * | 6/2003 | Carpenter et al. | 248/160 |

FOREIGN PATENT DOCUMENTS

| | | |
|---|---|---|
| DE | 29708050 | 5/1997 |
| EP | 0 167 345 A1 | 1/1986 |
| EP | 0 293 760 A3 | 5/1988 |
| EP | 0 432 560 A2 | 11/1990 |
| EP | 0 630 629 A1 | 12/1994 |
| EP | 0 668 058 A1 | 8/1995 |
| EP | 0 808 606 A1 | 11/1997 |
| EP | 0 920 835 A1 | 6/1999 |
| GB | 2 140 695 A | 12/1984 |
| GB | 2 214 428 A | 9/1989 |
| GB | 2233561 | 1/1991 |
| GB | 2 214 428 B | 6/1991 |

| | | |
|---|---|---|
| GB | 2267827 | 12/1993 |
| JP | 59143408 | 8/1984 |
| JP | 01232945 | 9/1989 |
| JP | 06012045 | 1/1994 |
| JP | 02607600 | 5/1997 |
| WO | WO 87/04081 | 7/1987 |
| WO | WO 88/00481 | 1/1988 |
| WO | WO 94/03142 | 2/1994 |
| WO | WO 94/14383 | 7/1994 |
| WO | WO 94/14715 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 98/10705 | 3/1998 |
| WO | WO 98/17182 | 4/1998 |
| WO | WO 98/27869 | 7/1998 |
| WO | WO 99/16367 | 4/1999 |

OTHER PUBLICATIONS

Direct Myocardial Revascularization by Saphenous Vein Graft, R.G. Favaloro, MD; DG Effler, MD; LK Groves, MD; WG Sheldon, MD; and FM Sones, Jr., MD / The Annals of Thoracic Surgery, vol. 10, No. 2, Aug. 1970.

A Simple Technique and Device To Provide a Bloodless Operative Field in Coronary Artery Surgery Without Cross-Clamping the Aorta, M. Riahi, RJ Schlosser and LA Tomastis/The Journal of Thoracic and Cardiovascular Surgery, vol. 66, No. 6, Dec. 1973, pp. 974-978.

To Use or Not To Use the Pump Oxygenator in Coronary Bypass Operations, Drs. WG Trapp and R. Bisarya/The Annals of Thoracic Surgery, vol. 19, No. 1, Jan. 1975, pp. 108-109.

A Prospective Evaluation of the Pulsatile Assist Device, GL Zumbro, Jr., MD; G Shearer, CCP; ME Fishback, MD; and RF Galloway, MD / The Annals of Thoracic Surgery, vol. 28, No. 2, Aug. 1979, pp. 269-273.

Preservation of Interventricular Septal Function in Patients Having Coronary Artery Bypass Graft Without Cardiopulmonary Bypass, CW Akins, MD; CA Boucher, MD; and GM Pohost, MD / American Heart Journal, vol. 107, No. 2, Feb. 1984, pp. 304-309.

Coronary Artery Revascularization Without Cardiopulmonary Bypass, R. Archer, DO; DA Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, Mar. 1984, pp. 52-57.

Direct Myocardial Revascularization Without Cardiopulmonary Bypass, E. Buffolo; JCS Andrade, J Succi; LEV Leao; and C Gallucci. Thoac. Cardiovasc. Surgeon, 33 (1985) pp. 26-29.

Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May-Jun. 1985, pp. 217-222.

Heart-Mechanical Assis Device Interaction, JY Kresh; PLM Kerkhof; SM Goldman; and SK Brockman, Trans. Am. Soc. Artif. Intern. Organs, vol. XXXII, 1986, pp. 437-443.

Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, Sep. 1987, pp. 710-712.

Long-Term Follow-up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116-124.

Extended Clinical Support with an Implantable Left Ventricular Assist Device, MG McGee; SM Parnis; T. Nakatani; T Myers; K Dasse; MD Hare; JM Duncan; VL Poirier; and OH Frazier, Trans Am. Soc. Artif. Intern. Organs, vol. XXXV, 1989, pp. 614-616.

Current Status of Cardiac Surgery: A 40-Year Review, WE Richenbacher, MD; JL Myers, MD, FACC; JA Walhausen, MD, FACC, Journal of American College of Cardiology, vol. 14, No. 3, Sep. 1989, pp. 535-544.

Transfemoral Placement of the Left Ventricular Assist Device "Hemopump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, vol. 38 (1990) pp. 69-72.

Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100, No. 1, Jul. 1991.

Direct Myocardial Revascularization Without Extracorpoeal Circulation, FJ Benetti, MD; G Naselli, MD; M Wood, MD; and L Geffner, MD, Chest, vol. 100, No. 2, Aug. 1991, pp. 312-316.

Coronary Artery Bypass Without Cardiopulmonary Bypass Pfister et al, The Annals of Thoracic Surgery, vol. 54 #6 Dec. 1992 pp. 1085-1092.

Coronary Artery Operation Supported by the Hemopump: An Experimental Study on Pig, U Lonn, MD; B Peterzen, MD; H Granfeldt, MD; and H Casimir-Ahn, MD, Ph.D. The Annals of Thoracic Surgery, vol. 58, No. 1, Jul. 1994, pp. 516-523.

Regional Cardiac Wall Immobilization for Open Chest and Closed Chest Coronary Artery Bypass Grafting on the Beating Heart: The 'Octopus' Method, Circulation, vol. 92, No. 8 Supplement 1, I-177 (Oct. 15, 1995).

A Minimally Invasive Surgical Method for Coronary Revascularization—Preliminary Experience in Five Patients, MC Robinson, Dr Gross, and W Zeman, Circulation, (Oct. 15, 1995) vol. 92, No. 8, I-176.

Coronary Artery Bypass Grafting Without Cardiopulmonary Bypass and Without Interruption of Native Coronary Flow Using a Novel Astamosis Site Restraining Device("Octopus"), C. Borst et al., Journal of the American College of Cardiology, vol. 27, No. 6, 1356-1364 (May 1996).

Cardiogenic Shock Complicating Acute Myocardial Infarction: the Use of Coronary Angioplasty and the Integration of the New Support Device into Patient Management, GM Gacioch, MD; Stephen G. Ellism, MD, FACC; L Lee. MD; ER Bates, MD, FACC; M Kirsh, MD, FACC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD. Ph.D., The Annals of Thoracic Surgery, vol. 55, No. 2, Feb. 1993, pp. 486-489.

Enhanced Preservation of Acutely Ischemic Myocardium with Transeptal Left Ventricular Assist, JD Fonger, MD; Y Zhou, MD; H Matsuura, MD; GS Aldea, MD; and RJ Shemin, MD, The Annals of Thoracic Surgery, vol. 57, No. 3, Mar. 1994, pp. 570-575.

Transcatheter Radiofrequency Ablation of Atrial Tissue Using a Suction Catheter, Th Lavergne et al. (PACE, vol. 12, Jan. 1989, Part II, pp. 177-186.

Abstract: "Closed Chest Coronary Artery Bypass With Cardioplegic Arrest in the Dog", Stevens et al. 67th Scientific Sessions.

Placement of Coronary Artery Bypass Graft without Oxygenator, Trapp et al., Journal of The Society of Thoracic Surgeons and The Southern Thoracic Surgical Assn. vol. 19. No. 7 Jan. 1975.

Experimental Videothoracoscopic Cannulation of the Left Atrial Appendix: A Feasible Rapid Approach For Initiating Left Heart Bypass? PF Gründeman; DW Meijer; JJG Bannenberg; R tukkie; and PJ Klopper, Surgical Endoscopy (1993) 7: 511-513.

A.J. Delrossi, M.D., and G.M. Lemore, M.D., A New Retractor to Aid In Coronary Artery Surgery, The Annals of Thoracic and Caridovascular Surgery, vol. 36 Jul. 1983 pp. 101-102.

Stephen Westaby, FRCS, and Federico J. Benetti, MD., Less Invasive Coronary Surgery: Consensus From the Oxford Meeting, Annals of Thoracic Surgery 1996; 62: 924-31.

Kolessov V.I., The Surgery of CoronaryArteries of the Heart, Leningrad, Meditsina, 1977, pp. 360. (Russian Article).

Kosesssov V.I., The Surgery Of Coronary Arteries of the Heart, Leningrad, Meditsina., 1977, pp. 360. (English Translation).

Reexam Control No. 90/005,995 dated May 3, 2001.

Reexam Control No. 90/005,994 dated May 3, 2001.

* cited by examiner

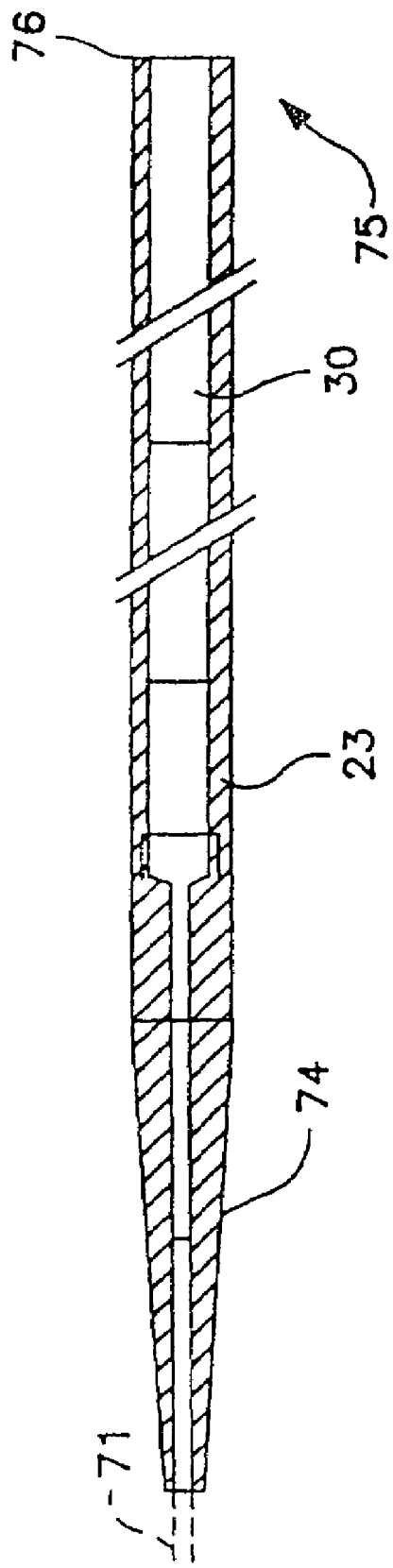
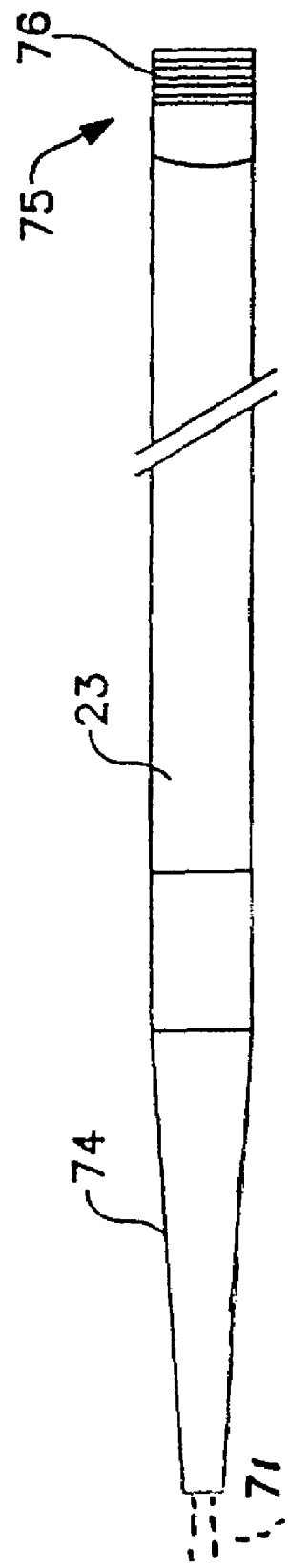

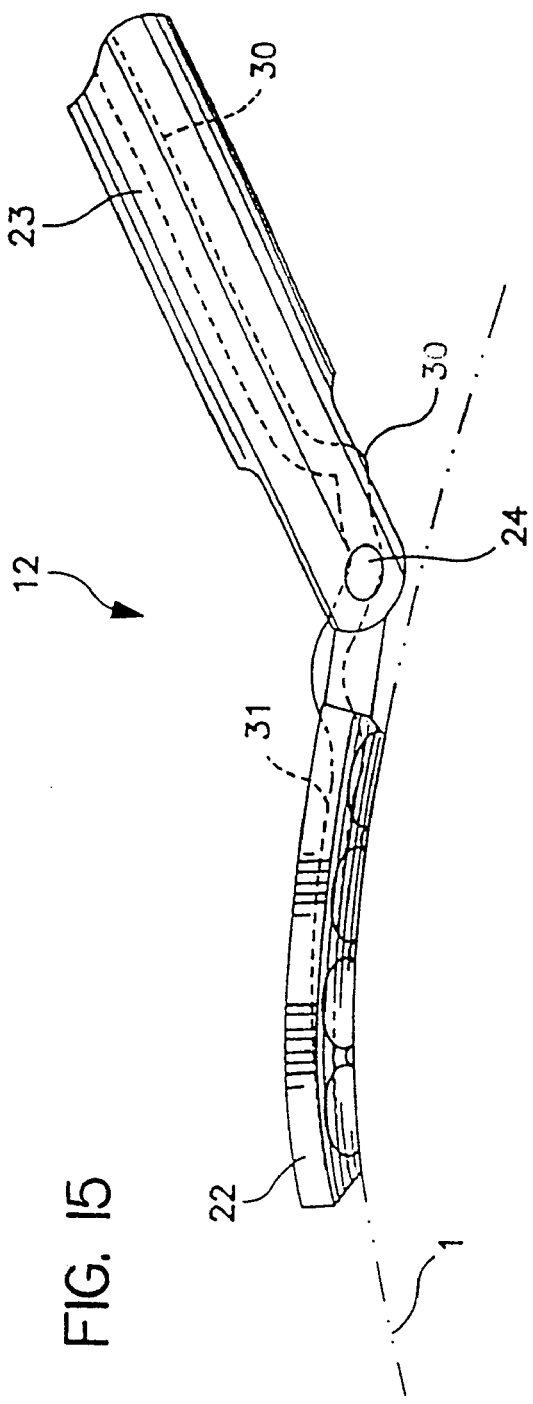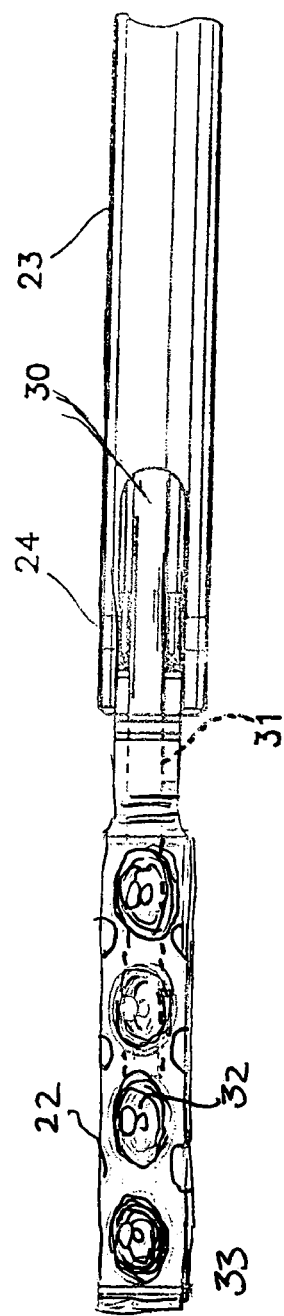
FIG. 15
FIG. 16

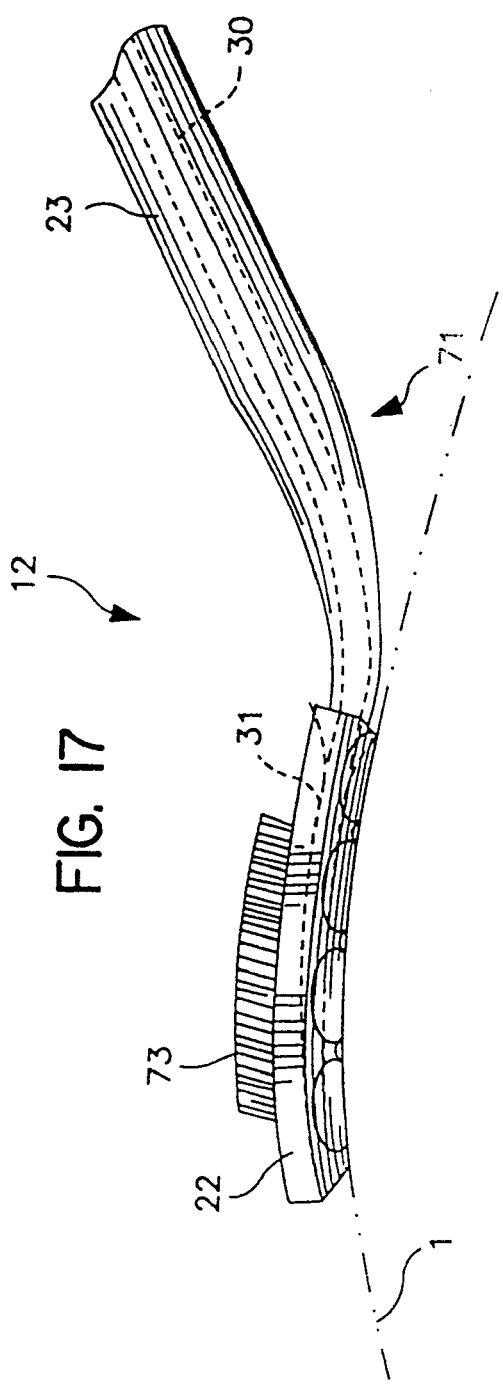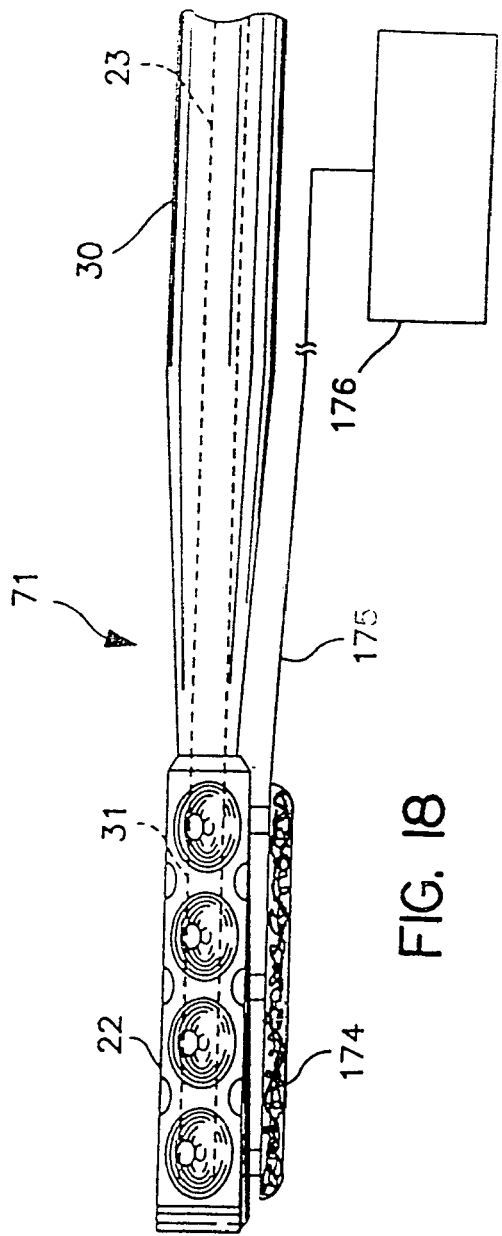

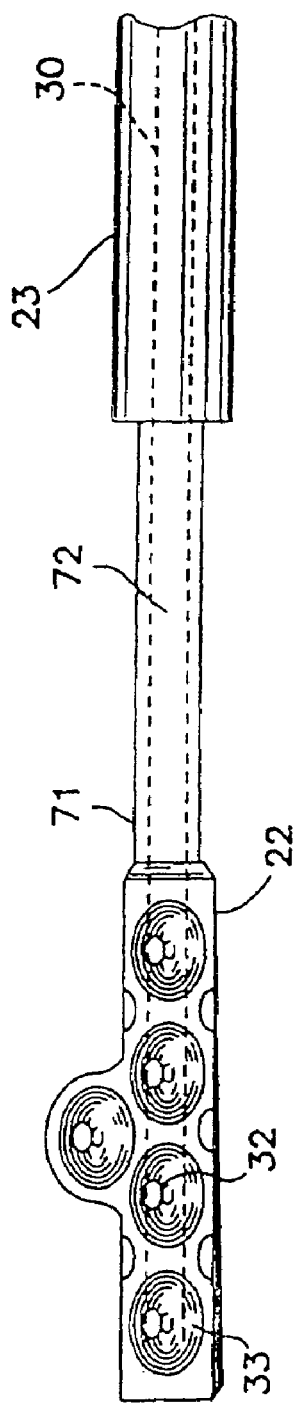
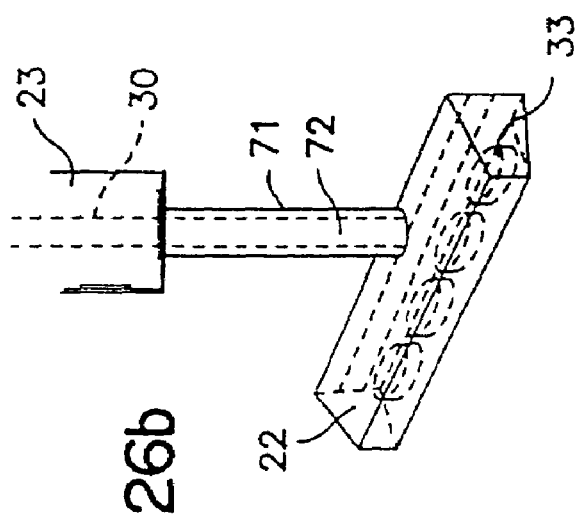
FIG. 26a
FIG. 26b

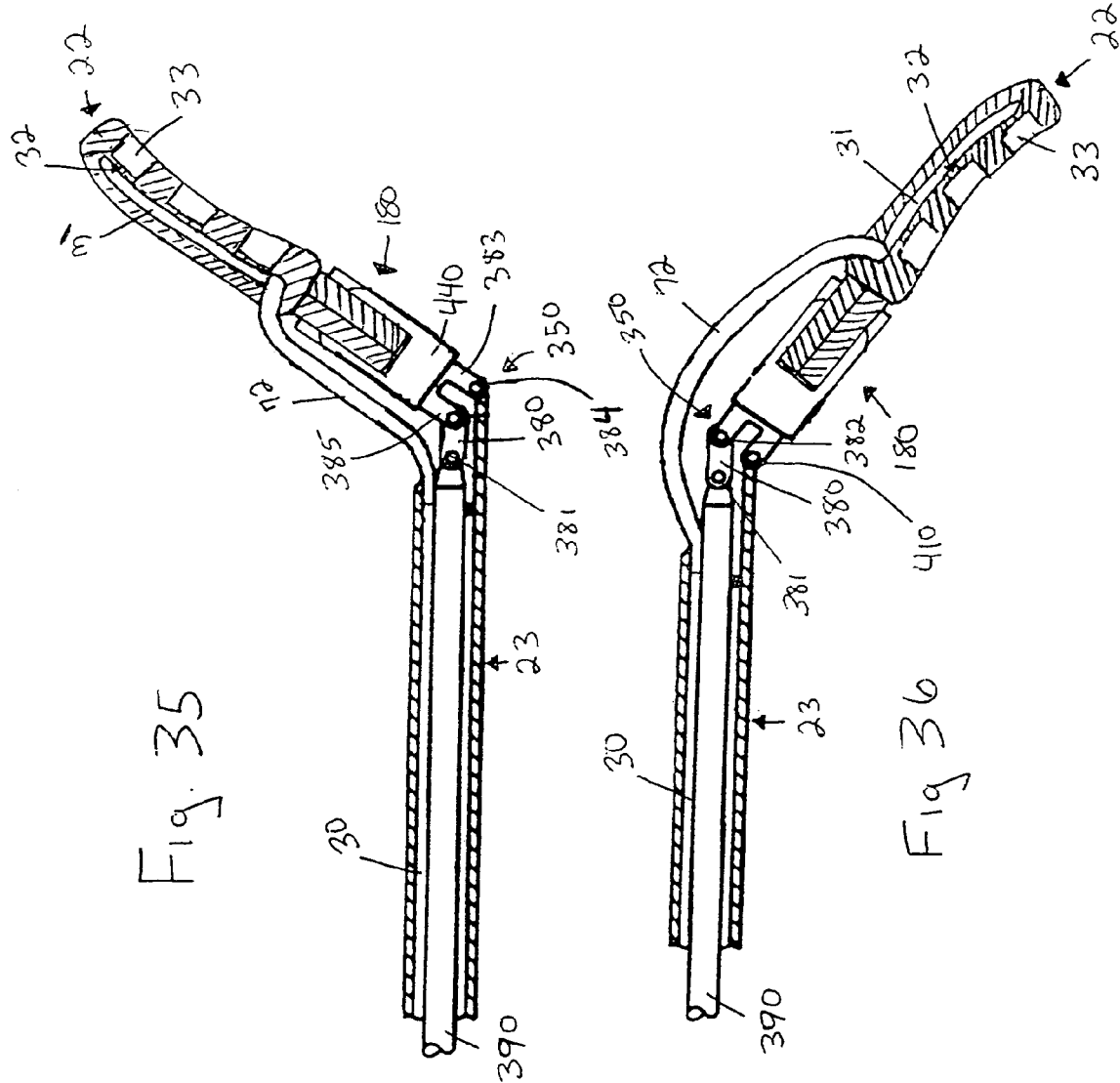

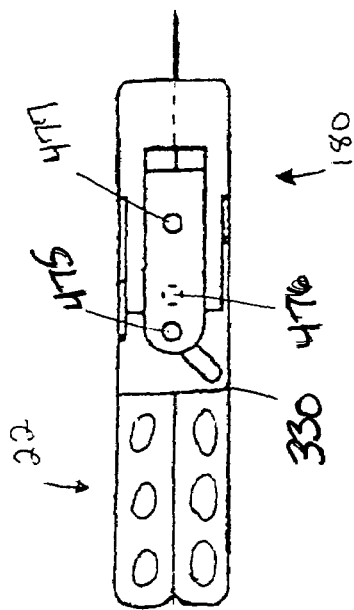
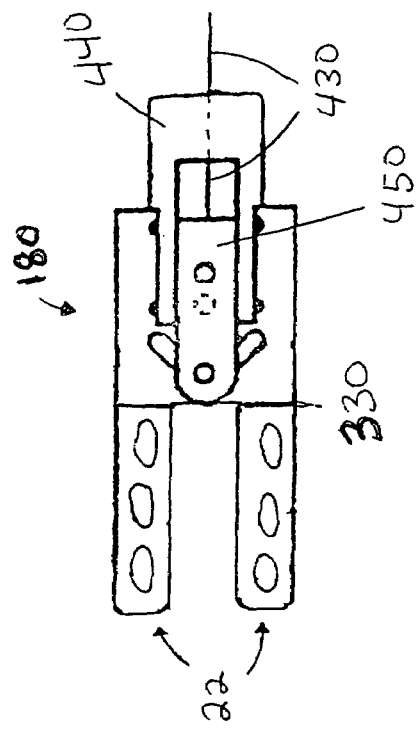

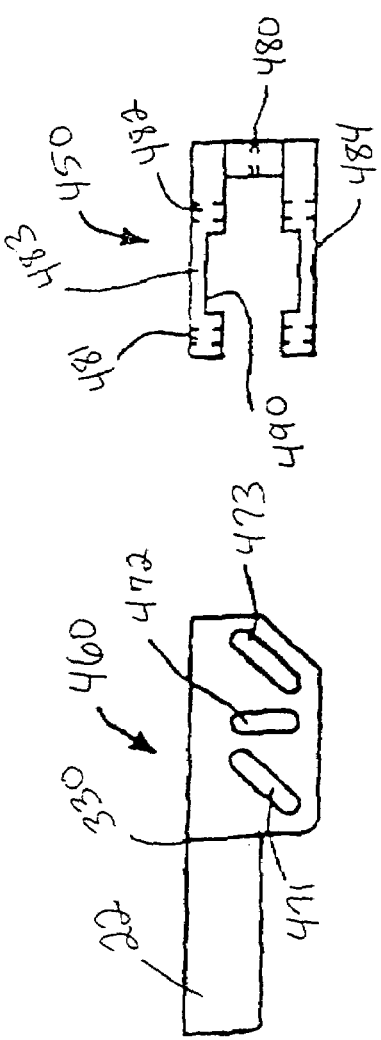
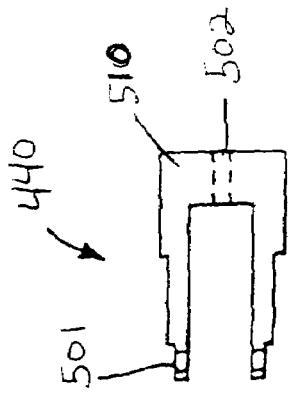
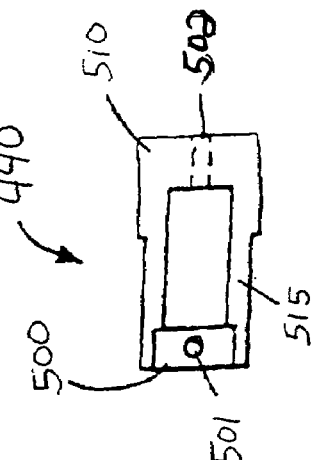
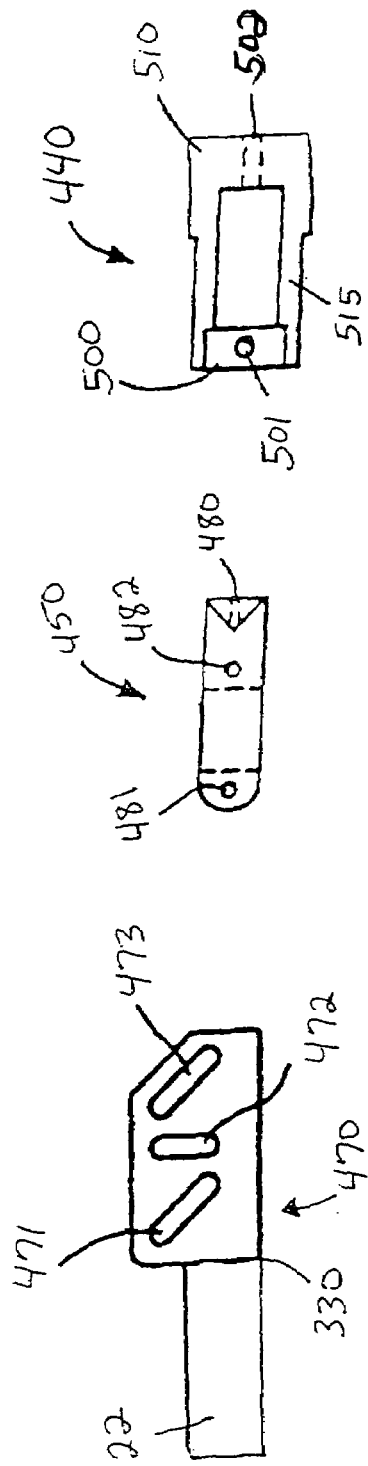

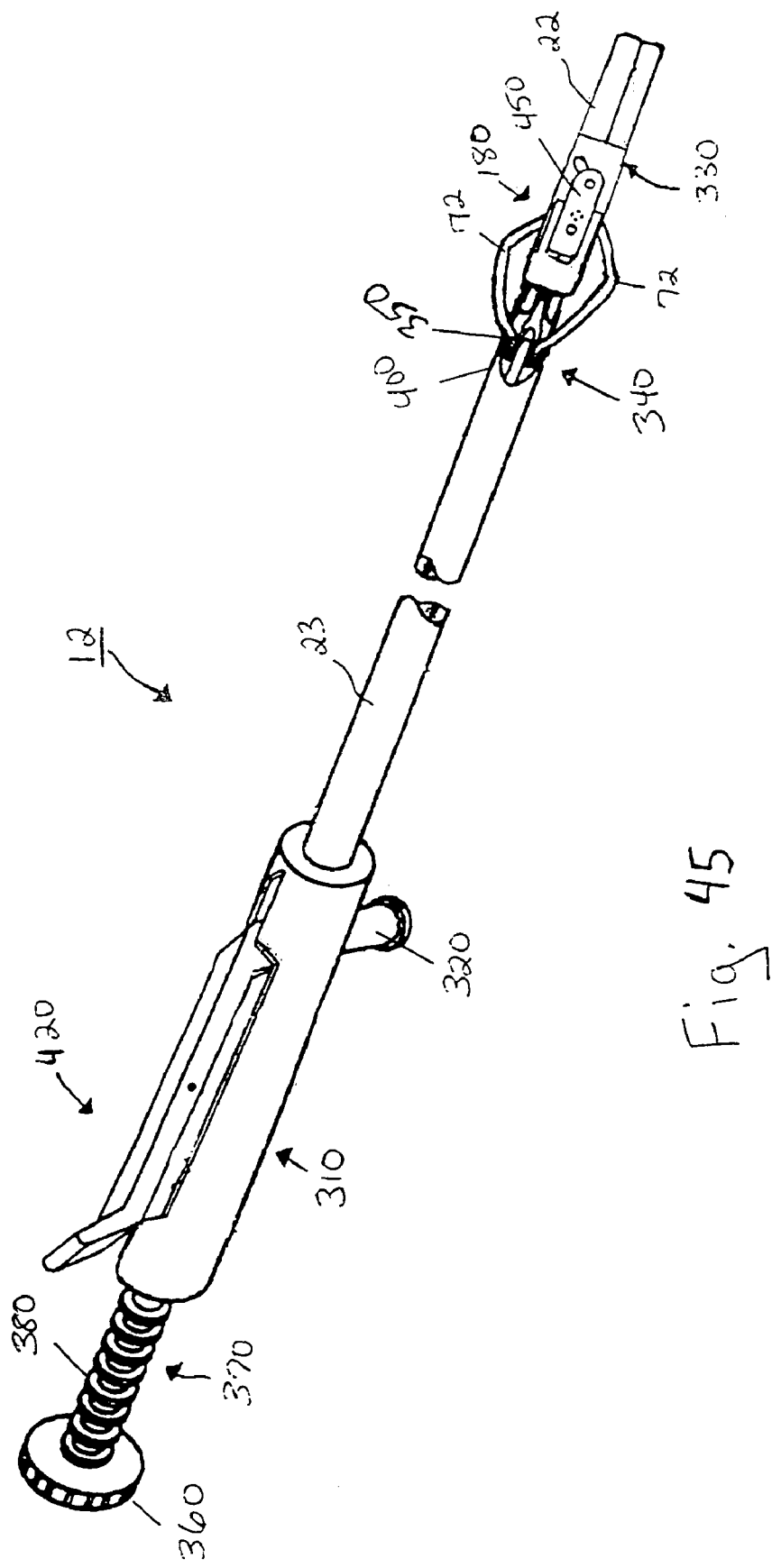

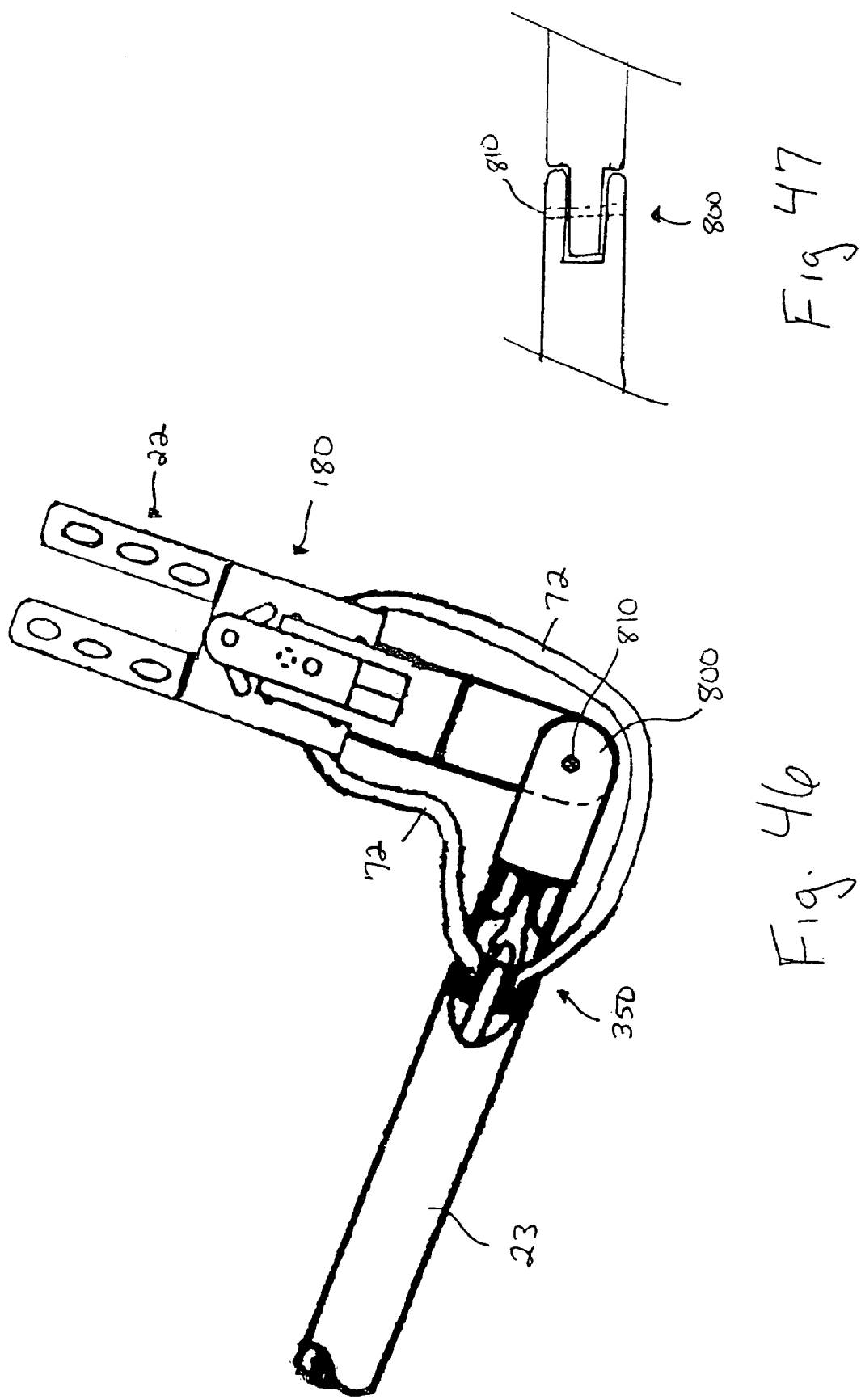

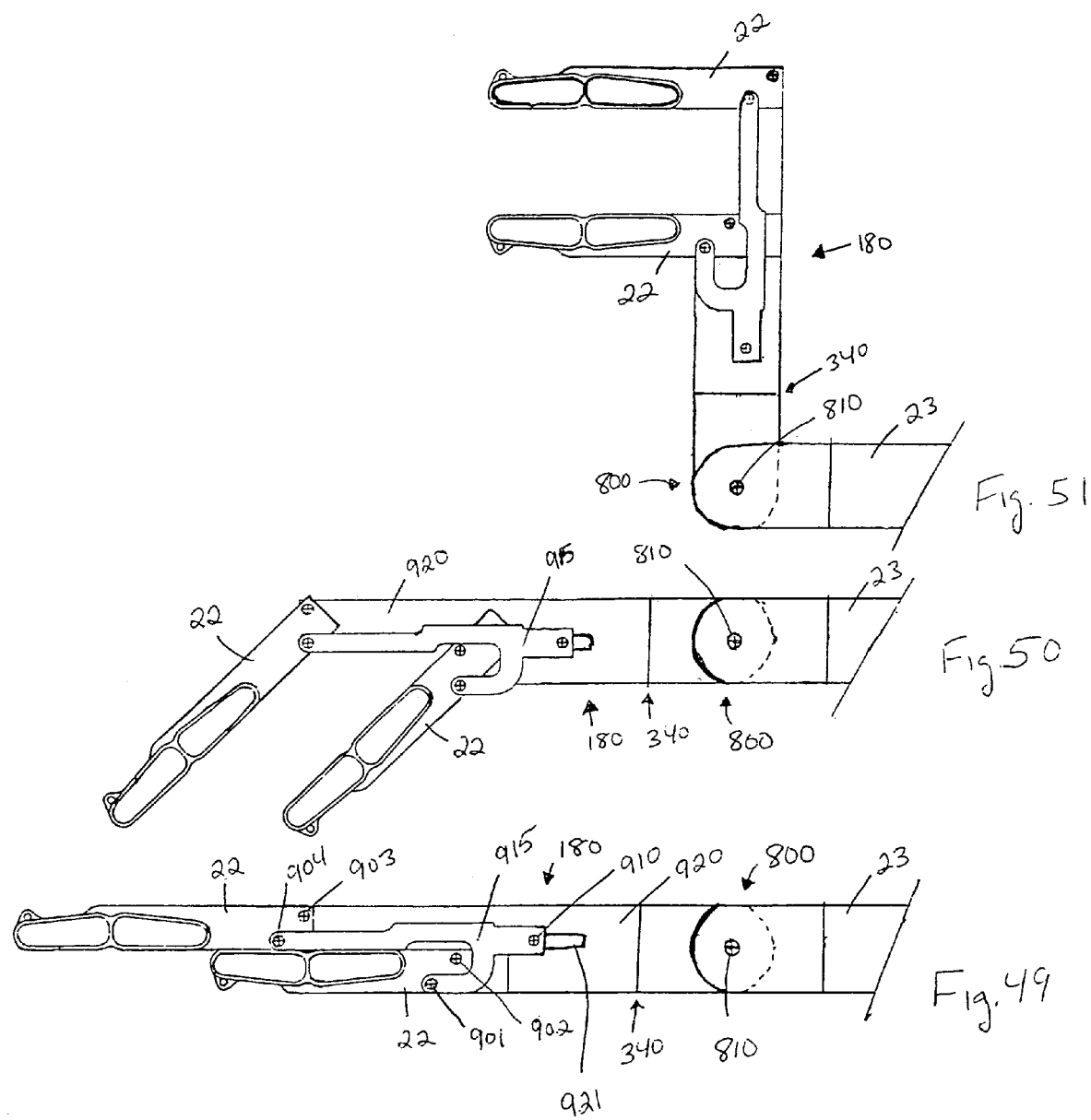

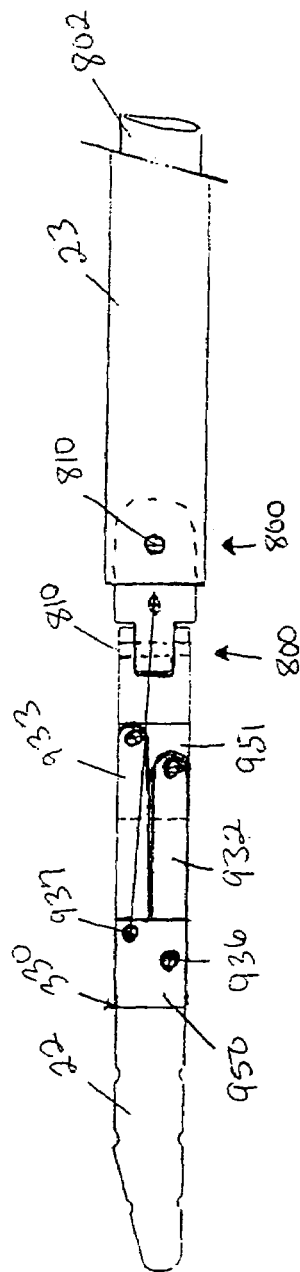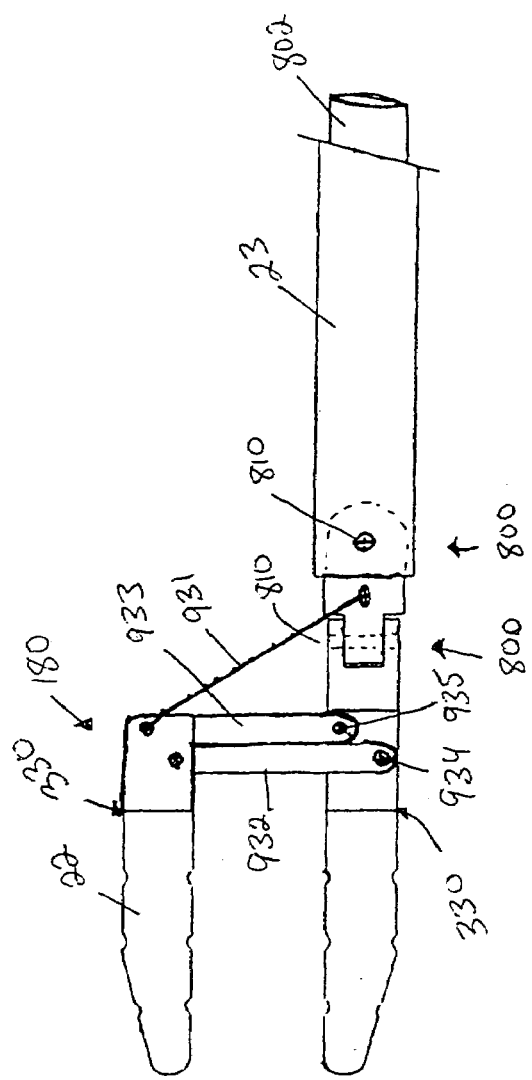

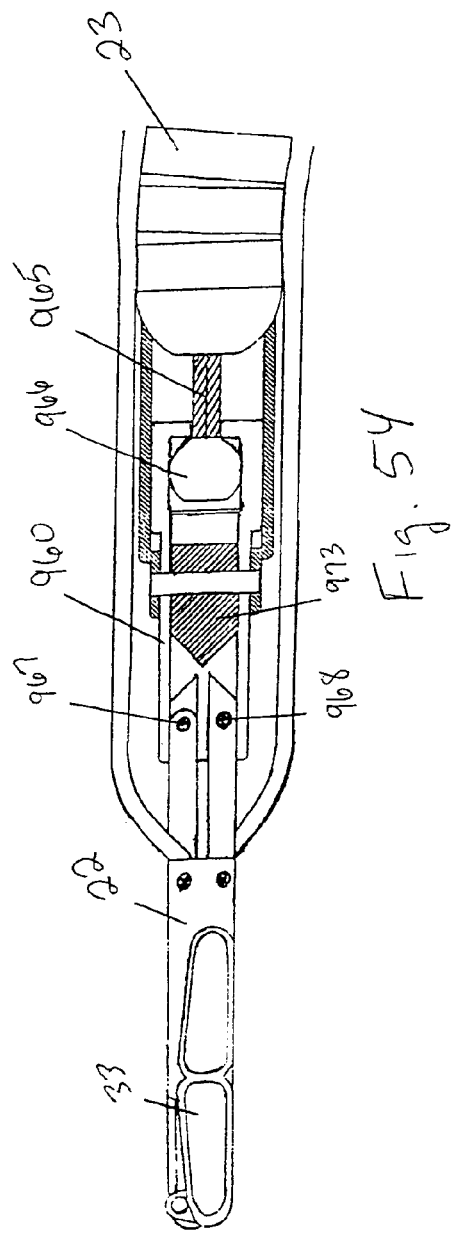
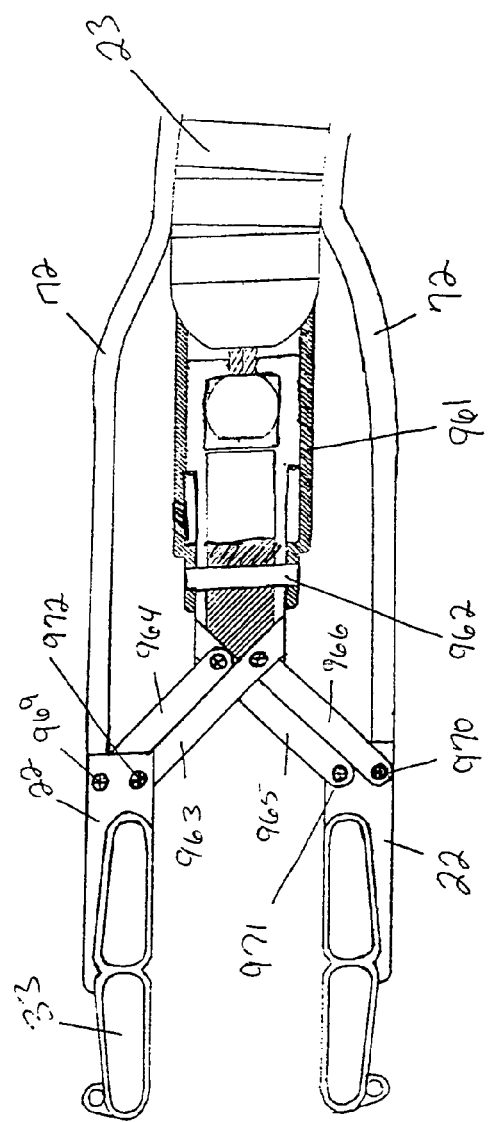

METHOD AND APPARATUS FOR TEMPORARILY IMMOBILIZING A LOCAL AREA OF TISSUE

RELATED APPLICATION

This is a continuation application claiming priority from U.S. patent application Ser. No. 09/678,203 filed Oct. 2, 2000 which is a continuation-in-part application claiming priority from U.S. patent application Ser. No. 09/493,466 filed Jan. 28, 2000 now U.S. Pat. No. 6,371,906, which is a divisional of prior U.S. patent application Ser. No. 09/334,531 filed Jun. 16, 1999 now U.S. Pat. No. 6,364,826, which is a divisional of prior U.S. patent application Ser. No. 08/725,371 filed Oct. 3, 1996 now U.S. Pat. No. 6,015,378, which is a continuation-in-part of prior U.S. patent application Ser. No. 08/531,363 filed Sep. 20, 1995 of Borst et al. entitled METHOD AND APPARATUS FOR TEMPORARILY IMMOBILIZING A LOCAL AREA OF TISSUE now U.S. Pat. No. 5,836,311.

FIELD OF THE INVENTION

The present invention generally relates to surgery on body tissues and organs. More specifically, the present invention relates to a method and apparatus for temporarily immobilizing a local area of tissue subject to motion, such as the heart wall, which permits a surgical procedure to be performed on that local area of tissue.

BACKGROUND OF THE INVENTION

Coronary artery disease remains the leading cause of morbidity and mortality in Western societies. Coronary artery disease is manifested in a number of ways. For example, disease of the coronary arteries can lead to insufficient blood flow to various areas of the heart. This can lead to the discomfort of angina and the risk of ischemia. In severe cases, acute blockage of coronary blood flow can result in irreversible damage to the myocardial tissue including myocardial infarction and the risk of death.

A number of approaches have been developed for treating coronary artery disease. In less severe cases, it is often sufficient to merely treat the symptoms, with pharmaceuticals, or treat the underlying causes of the disease, with lifestyle modification. In more severe cases, the coronary blockage can be treated endovascularly or percutaneously using techniques such as balloon angioplasty, atherectomy, laser ablation, stents, and the like.

In cases where these approaches have failed or are likely to fail, it is often necessary to perform a coronary artery bypass graft procedure. This procedure generally consists of the following steps: First, direct access to the heart is achieved. This is usually done by opening the chest by median sternotomy and spreading the left and right rib cage apart; and opening the pericardial sac to achieve direct access to the heart.

Next, a blood vessel or vessels for use in the graft procedure are mobilized from the patient. This usually entails mobilizing either a mammary artery or a saphenous vein, although other graft vessels may also be used.

Next, a heart-lung or cardiopulmonary bypass is performed. This usually entails arterial and venous cannulation, connecting the bloodstream to a heart-lung machine, cooling the body to about 32 degrees Celsius, cross-clamping of the aorta and cardioplegic perfusion of the coronary arteries to arrest and cool the heart to about 4 degrees Celsius. The arrest or stoppage of the heart is generally required because the constant pumping motion of the beating heart would make surgery upon the heart difficult in some locations and extremely difficult if not impossible in other locations Once cardiac arrest is achieved, then a graft (or grafts) is attached to the relevant portions of a coronary artery (or arteries) followed by weaning from the cardiopulmonary bypass, restarting the heart and decannulation. Finally the chest is closed.

One area which may create difficulties for the patient and extra expense and time for the procedure involves the cardiopulmonary bypass. In a cardiopulmonary bypass all the patient's blood, which normally returns to the right atrium, is diverted to a system which supplies oxygen to the blood and removes carbon dioxide and returns the blood, at sufficient pressure, into the patient's aorta for further distribution into the body. Generally such a system requires several separate components, including an oxygenator, several pumps, a reservoir, a blood temperature control system, filters as well as flow, pressure and temperature sensors.

Problems may develop during cardiopulmonary bypass due to the reaction blood has to non-endothelially lined surfaces, i.e. surfaces unlike those of a blood vessel. In particular, exposure of blood to foreign surfaces results in the activation of virtually all the humoral and cellular components of the inflammatory response, as well as some of the slower reacting specific immune responses. Other complications from cardiopulmonary bypass include loss of red blood cells and platelets due to shear stress damage. In addition, cardiopulmonary bypass requires the use of an anticoagulant, such as heparin. This may, in turn, increase the risk of hemorrhage. Finally cardiopulmonary bypass sometimes necessitates giving additional blood to the patient. The additional blood, if from a source other than the patient, may expose the patient to blood born diseases.

Due to the risks incurred during cardiopulmonary bypass, others have attempted to perform a coronary artery bypass graft procedure without cardiac arrest and cardiopulmonary bypass. For example, Trapp and Bisarya in "Placement of Coronary Artery Bypass Graft Without Pump Oxygenator", Annals Thorac. Surg. Vol. 19, No. 1, (January 1975) pgs. 1–9, immobilized the area of the bypass graft by encircling sutures deep enough to incorporate enough muscle to suspend an area of the heart and prevent damage to the coronary artery. More recently Fanning et al. in "Reoperative Coronary Artery Bypass Grafting Without Cardiopulmonary Bypass", Annals Thorac. Surg. Vol. 55, (February 1993) pgs. 486–489 also reported immobilizing the area of the bypass graft with stabilization sutures.

While these attempts have achieved some success, they generally require enhanced skill of the surgeon to properly create the anastomosis because, even with sutures, the beating heart continues to move in the relevant area more than desired.

SUMMARY OF THE INVENTION

In one embodiment of the invention, an actuator is configured to operate a spreader to selectively control the movement of a first tissue engaging member among a first position, a second position, and at least a third position, and selectively control the movement of the second tissue engaging member among a first position, a second position and at least a third position. The first tissue engaging member and the second tissue engaging member are coupled to the spreader. The spreader is carried on an arm distal end and the actuator is carried on the arm proximal end.

In another embodiment of the invention, the first tissue engaging member and the second tissue engaging member are further spread once they are coupled to a tissue surface to place the tissue between the first tissue engaging member and the second tissue engaging member under tension.

In still another embodiment of the invention, a method is employed to introduce the first tissue engaging member and second tissue engaging members into a patient's body. The tissue engaging members are spread and this spreading is controlled so a selective amount of spreading occurs. After the tissue engaging member have been spread a selective amount, the tissue engaging members are coupled to the tissue surface desired to be stabilized.

BRIEF DESCRIPTION OF THE DRAWINGS

The foregoing and other aspects of the present invention will best be appreciated with reference to the detailed description of the invention in conjunction with the accompanying drawings, wherein:

FIG. 6 is a longitudinal sectional view of the suction arm used in the present invention.

FIG. 7 is a plan view of the suction arm used in the present invention.

FIG. 15 is a side view of an alternate embodiment of the present invention, shown placed against the surface of the heart.

FIG. 16 is a bottom view of the alternate embodiment of the present invention device shown in FIG. 15.

FIG. 17 is a side view of a further alternate embodiment of the present invention, shown placed against the surface of the heart.

FIG. 18 is a bottom view of still further alternate embodiment of the present invention.

FIG. 26A is a view of the bottom of an alternate embodiment of a suction paddle used in the immobilizing device.

FIG. 26B is a perspective view of a further alternate embodiment of a suction paddle used in the immobilizing device.

FIG. 35 is a longitudinal cross-sectional view of the distal end of a suction device.

FIG. 36 is a longitudinal cross-sectional view of the distal end of a suction device.

FIG. 37 is a bottom view of a spreader with coupled suction paddles in a non-spread position.

FIG. 38 is a bottom view of spreader with coupled suction paddles in a spread position.

FIG. 39 is a plan view of a spreader member.

FIG. 40 is a plan view of a spreader member.

FIG. 41 is a plan view of a slide component of a spreader.

FIG. 42 is a side view of a slide component of a spreader.

FIG. 43 is a side view of an anchor component of a spreader.

FIG. 44 is a plan view of an anchor component of a spreader.

FIG. 45 depicts a further alternate embodiment of the present invention, and in particular of a suction device that may be used in an endoscopic procedure featuring an arm, and a pair of tissue engaging members and a spreader.

FIG. 46 depicts an alternate embodiment of of the present invention, and in particular of a suction device that may be used in an endoscopic procedure featuring an arm with joints, and a pair of tissue engaging members and a spreader.

FIG. 47 is a side view of a joint.

FIG. 49 depicts a further alternate embodiment of the present invention, and in particular of a suction device that may be used in an endoscopic procedure, as described earlier, featuring an arm with joints, and a pair of tissue engaging members and a spreader.

FIG. 50 depicts a further alternate embodiment of the present invention, and in particular of a suction device that may be used in an endoscopic procedure, as described earlier, featuring an arm with joints, and a pair of tissue engaging members and a spreader.

FIG. 51 depicts a further alternate embodiment of the present invention, and in particular of a suction device that may be used in an endoscopic procedure, as described earlier, featuring an arm with joints, and a pair of tissue engaging members and a spreader.

FIG. 52 depicts a further alternate embodiment of the present invention, and in particular of a suction device that may be used in an endoscopic procedure, as described earlier, featuring an arm with joints, and a pair of tissue engaging members and a spreader.

FIG. 53 depicts a further alternate embodiment of the present invention, and in particular of a suction device that may be used in an endoscopic procedure, as described earlier, featuring an arm with joints, and a pair of tissue engaging members and a spreader.

FIG. 54 depicts a further alternate embodiment of the present invention, and in particular of a suction device that may be used in an endoscopic procedure, as described earlier, featuring an arm with joints, and a pair of tissue engaging members and a spreader.

FIG. 55 depicts a further alternate embodiment of the present invention, and in particular of a suction device that may be used in an endoscopic procedure, as described earlier, featuring an arm with joints, and a pair of tissue engaging members and a spreader.

The drawings are not necessarily to scale.

DETAILED DESCRIPTION OF THE PREFERRED EMBODIMENT

Figure 1:
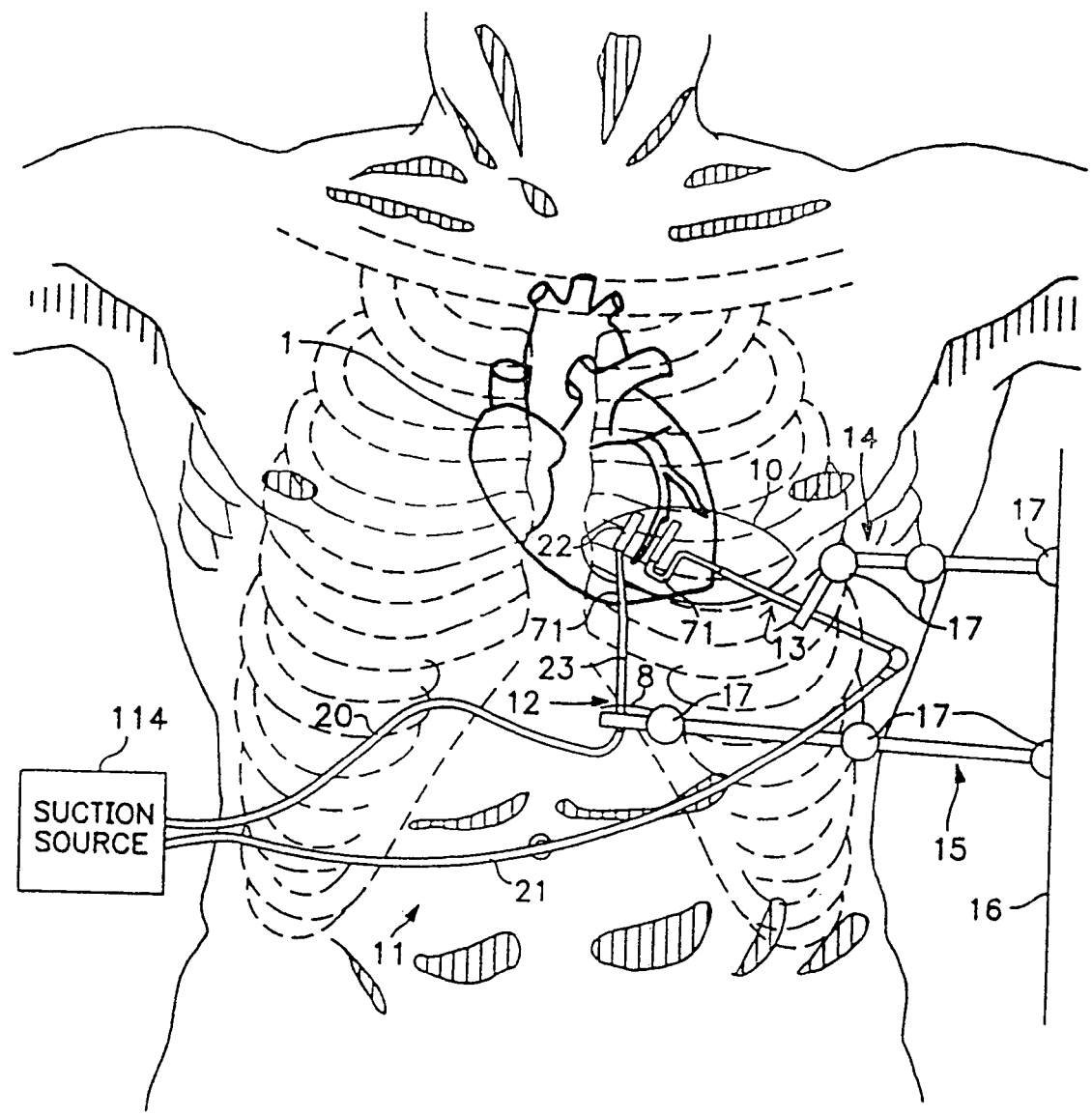
FIG. 1 is a plan view of the device being used to temporarily immobilize a local area of heart tissue in which access to the heart is achieved through a mini-thoracotomy.

FIG. 1 is a view of the immobilizing device 11 being used to temporarily immobilize an area of heart tissue. In the preferred embodiment, surgical access to the local area of heart tissue is achieved through a mini-thoracotomy, preferably performed within either the fourth or fifth intercostal space. An incision 10 of approximately 10 centimeters is made into chest cavity between the ribs (seen here in phantom.) The rib cartilage may be temporarily removed and the ribs surrounding the incision slightly spread apart using a retractor (not shown) to provide adequate surgical access to the mammary artery and the heart. As seen, a pair of suction devices 12, 13 are introduced. The first suction device 12 is introduced through a small stab wound 8 in between the ribs approximately 10 cm. below incision 10. This stab wound is made in any acceptable manner. Incidentally, once the surgery has been completed, the stab wound may be used for the thorax drain after the closure of the chest. As discussed below with reference to FIG. 19, the suction device has a covering 180, made from latex rubber, over the distal end when it penetrates the chest wall in order to avoid blood and tissue from entering the suction ports and block suction apertures. Once suction device is introduced, covering 180 is removed and the distal end is positioned onto heart. The second suction device 13 is introduced through incision 10 onto the surface of the heart. As seen, the distal end of each suction device is ultimately positioned in the local area of heart tissue to be immobilized, i.e. on either side of a coronary artery upon which a graft is to be made.

As seen, suction devices 12, 13 are secured using securing devices 14, 15 respectively to a stationary object, such as surgical table 16 Of course other. objects besides the surgical table may be used as a stationary object, including the floor, ceiling or even the patient, such as a portion of the skeletal system of the patient, e.g. the sternum, In the preferred embodiment, each securing device 14, 15 is a variable friction arm, model no. 244 available from Manfrotto Nord, Inc. of Zona Industriale di Villapaiera, I-32032 Feltre BL, Italy Each securing device 14, 15 has a series of variable elbow joints 17 which may be locked in position. Thus the securing device permits the suction device to be locked into any position desired within three-dimensional space. Although not show, each securing device (or each suction device or both) may also be interconnected such that a truss type structure is created and the entire stiffness or rigidity of the immobilizing device 11 is improved.

Suction devices 12, 13 are coupled to a suction source 114 through lines 20, 21. Suction source 114 is preferably the standard suction available in the operating room and coupled to the devices with a two liter buffer flask (not shown) for each device. Suction is provided at a negative pressure of between 200–600 mm Hg with 400 mm Hg preferred. As seen, each suction device has essentially two portions, a paddle 22 and an arm 23. FIGS. 2 and 3 detail suction devices 12 and 13 respectively.

Figure 2A:
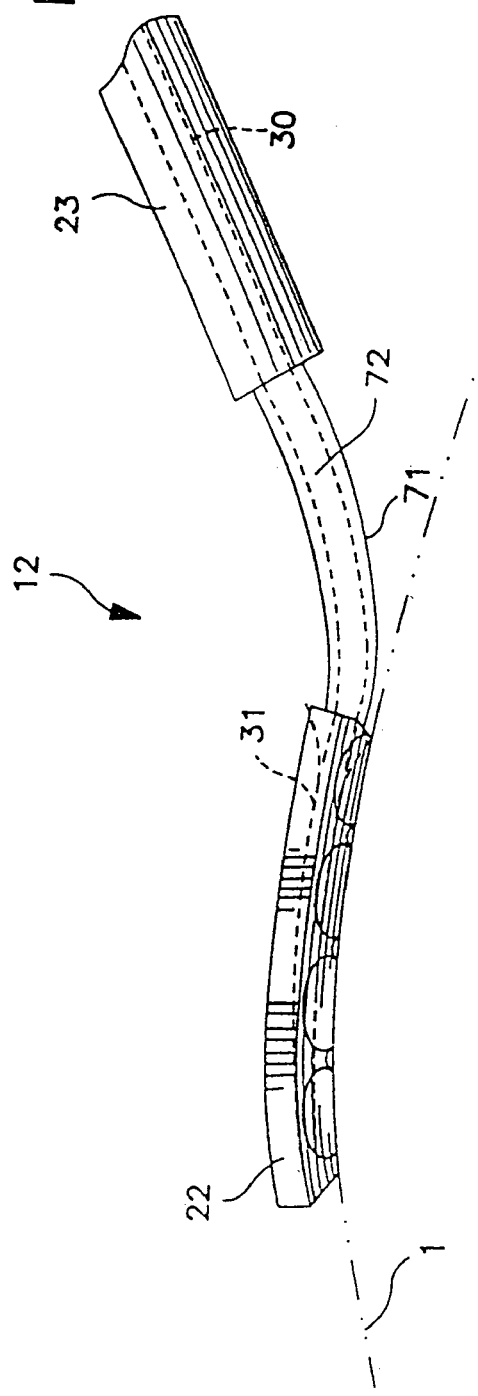
FIGS. 2a and 2b depict a first type of suction device shown in use in FIG. 1.
Figure 2B:
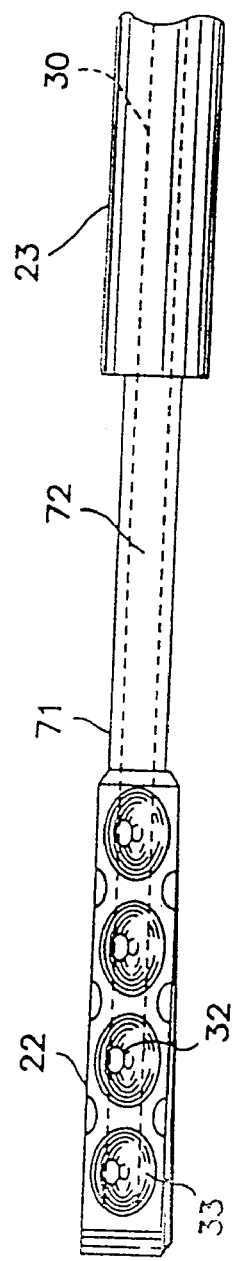

Turning now to FIGS. 2a and 2b, FIG. 2a is a side view of a suction device 12 showing its placement against the outline of a heart. As seen, the distal end of suction device comprises a paddle 22 and arm 23 coupled together by a continuous hinge or neck 71. Paddle 22 has a generally planar surface which conforms generally to the curvature of a heart 1, shown here in outline. In the preferred embodiment, suction arm 23 is coupled to suction paddle 22 such that suction paddle 22 may be rotated or bent to achieve the desired orientation relative to arm 23. This is accomplished by neck 71. Neck 71 is fashioned to be relatively bendable, that is to be bent by hand into the desired orientation, as opposed to paddle 22 and arm 23, which are rigid. In the preferred embodiment suction paddle 22 and suction arm 23 are constructed of stainless steel 316, while neck 71 is constructed of stainless steel 321. Of course other means may be provided to permit paddle 22 to move or rotate relative to arm 23 other than making neck 71 to be malleable by hand, such as a locking hinge as well as a remotely actuable joint, as is well known in the art. See for example, U.S. Pat. No. 5,374,277 of Hassler, incorporated herein by reference. A remotely actuable hinge is believed particularly advantageous for a suction device used endoscopically. In an alternate embodiment paddle may be fixed in a rigid orientation relative to arm. As seen, arm 23 has a suction lumen 30 therethrough which communicates with a suction conduit 31 in paddle 22 through neck lumen 72. Suction conduit 31 in paddle 22 further communicates through suction hole 32 (best seen in FIG. 2b) to suction port 33.

Figure 3A:
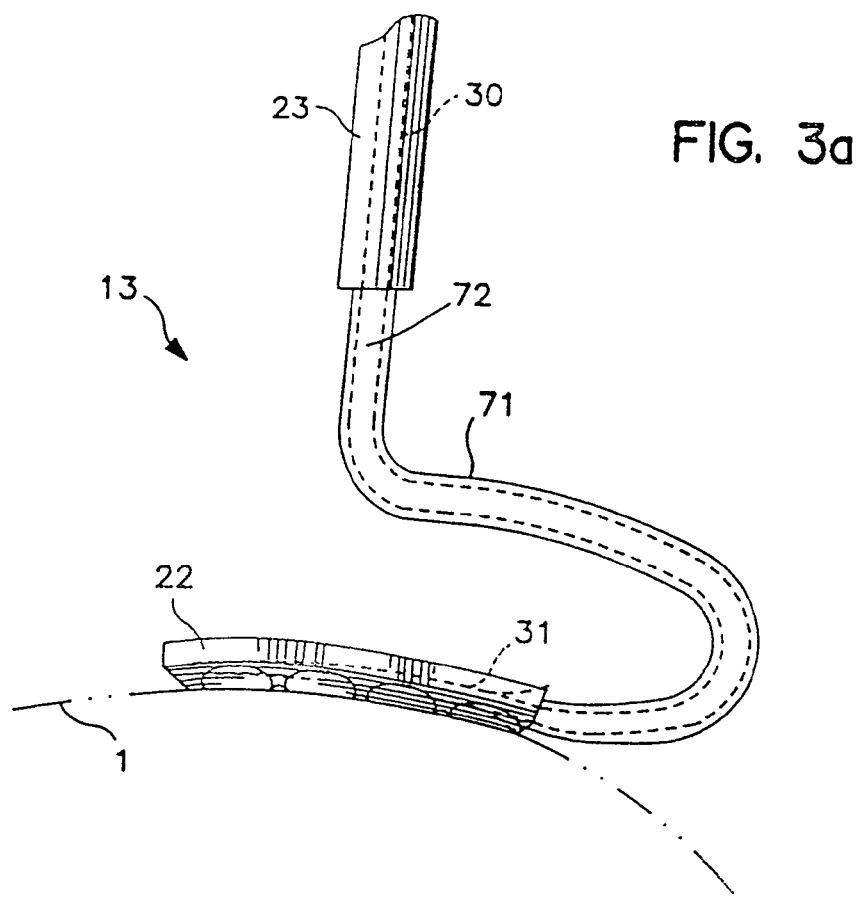
FIGS. 3a and 3b depict a second type of suction device shown in use in FIG. 1.
Figure 3B:
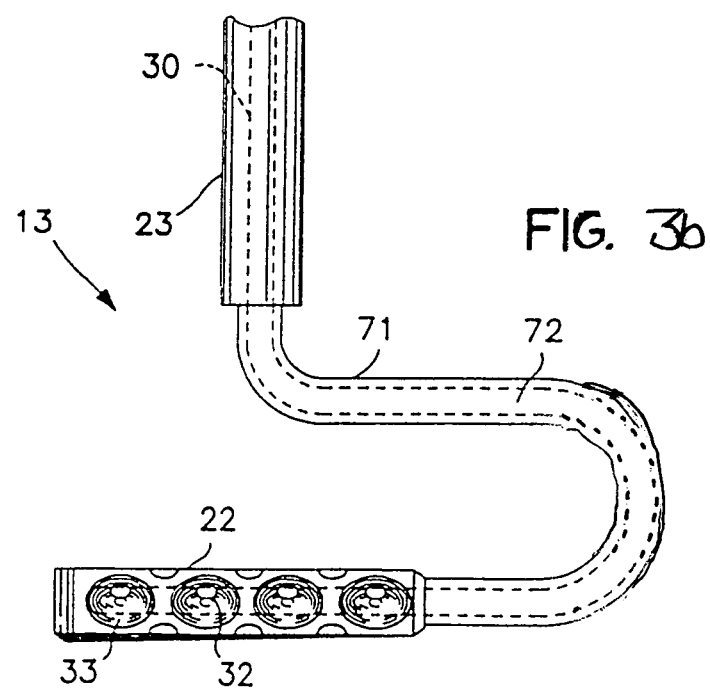

FIG. 2b is a view of the bottom of suction device 12. As seen, in the preferred embodiment four suction ports 33 in a row are featured, although the specific or exact number and position used may vary. Each suction port 33 has a suction aperture 32, each of which are preferably located at a position off-center from suction port 33. Suction apertures 32 are positioned off center from suction ports 33 so that if a large upwelling of tissue is caused by the suction (which may occur as a blister or bell-shaped curve) the tissue will not immediately close off the suction by obstructing suction aperture 32, as it would if the aperture were in the center of suction port 33. In addition, each suction aperture 32 has a much smaller diameter as compared to the diameter of suction port 33. This creates a high resistance pathway between suction port 33 and suction conduit 31 which permits the loss of a tissue-to-port seal in one suction port (and thus loss of fixation of the suction port to the tissue) to not also cause a precipitous pressure drop in the remainder of the suction ports. In the preferred embodiment suction aperture 32 has a diameter of 2 mm and suction port 33 has a diameter of 6 mm. As can be seen through a comparison between FIGS. 2A and 2B the relatively straight sided suction ports define a generally planar surface through the ends of each port Turning now to FIGS. 3a and 3b, FIG. 3a is a side view of a suction device 13 shown in FIG. 1. As seen, the distal end of suction device 13 comprises paddle 22 and arm 23 coupled together by a continuous hinge or neck 71. Paddle 22 has a generally planar surface which conforms generally to the curvature of a heart 1. In the preferred embodiment, suction arm 23 is coupled to suction paddle 22 such that suction paddle 22 may be rotated or bent along any of the three axes to achieve the desired orientation relative to arm 23. This is accomplished by neck 71. Neck 71 is substantially similar to that discussed in FIG. 2a but for the fact that suction device 13 has suction paddle 22 at an angled orientation to suction arm 23. In the preferred embodiment suction paddle 22 of suction device 13 is perpendicular to suction arm 23, although other angular orientations may be used.

FIG. 3b is a view of the bottom of suction device 13. As seen, in the preferred embodiment suction paddle 22 of suction device 13 is substantially similar to that described in FIG. 2b. In the preferred embodiment suction aperture 32 has a diameter of 2 mm and suction port 33 has a diameter of 6 mm.

Figure 4:
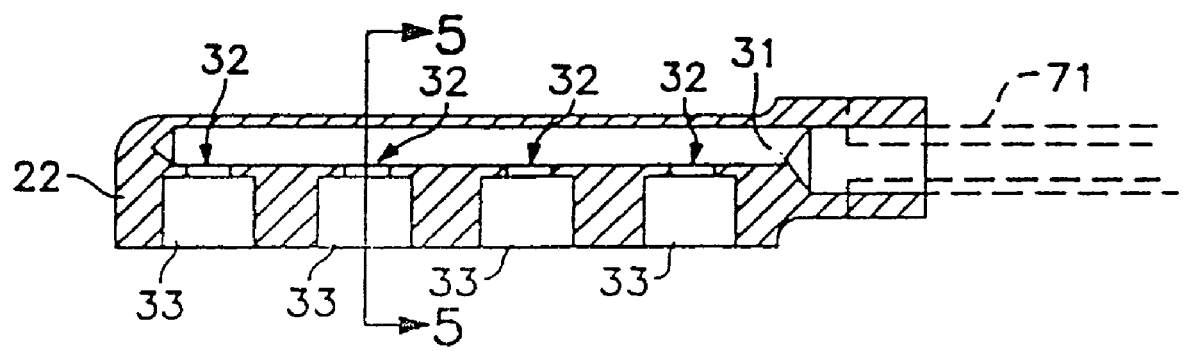
FIG. 4 is a longitudinal sectional view of the suction paddle used in the present invention.

FIG. 4 is a longitudinal cross-sectional view of suction paddle 22 used in immobilizing device 11. As seen, paddle 22 has a series of suction ports 33 each of which is connected to suction conduit 31 through a suction aperture 32. Each suction port 33 has generally straight, cylindrical sides. Of course other configurations may be used, such as cone-shaped suction ports, dome-shaped suction ports, etc. As can be seen through this FIG. it is the bottoms or ends themselves of the suction ports define a generally planar surface through the ends of each port along the bottom surface of the paddle. Moreover, although shown here as conjoined or defining a continuous surface, suction ports may be further arranged such that they are each separate and distinct from one another, but which would still define a planar surface along through their ends along the bottom of the paddle.

Figure 5:
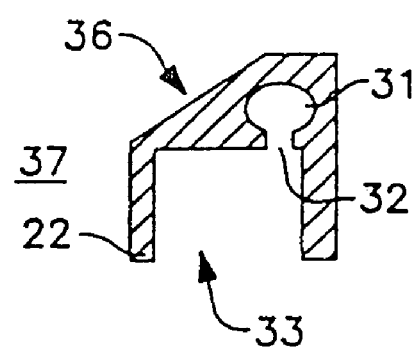
FIG. 5 is a cross-sectional view of the suction paddle used in the present invention taken along the line 5—5 of FIG. 4.

FIG. 5 is a cross-sectional view of the suction paddle 22 taken along the line 5—5 of FIG. 4 As seen, suction port 33 is connected to suction conduit 31 through suction aperture 32. Suction paddle 22 has a canted or slanted surface 36 at the top. Through this type of surface, area 37 may be better accessed for performing surgical procedures.

FIG. 6 is a longitudinal cross-sectional view of suction arm 23. Distal end 71 of suction arm 23 has neck 71 (not shown in this FIG.) fixed thereto. As seen, arm 23 has a suction lumen 30 therethrough which communicates with suction conduit 31 in paddle 22 through neck lumen 72 of neck 71 (shown in phantom in this FIG.). As seen in FIG. 7, which is a plan view of suction arm 23, proximal end 75 has a series of knurled ridges 76 to facilitate coupling a suction line coming from suction source (not shown in this FIG) to suction arm 23.

Figure 8:
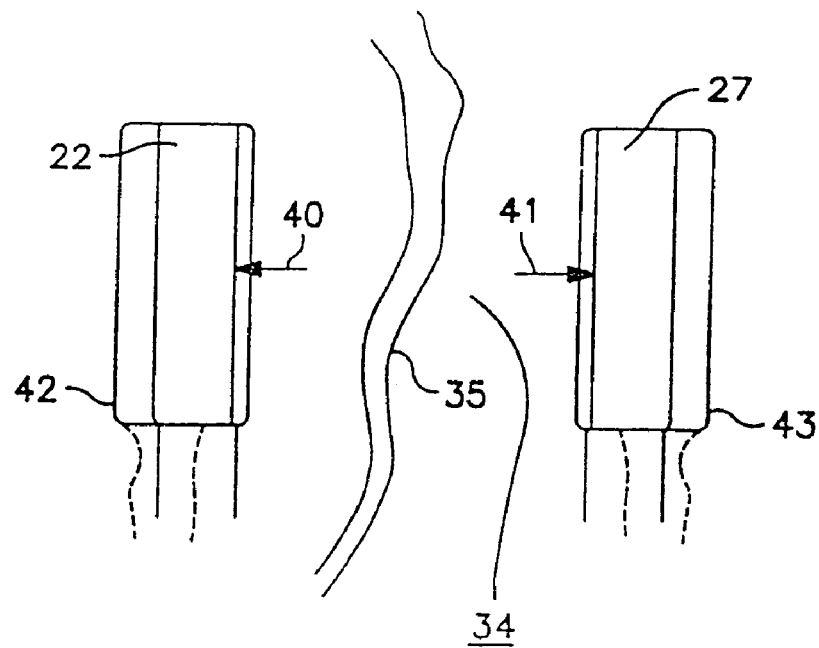
FIG. 8 is a detailed view of a pair of suction devices being positioned on a heart and spread apart.

FIG. 8 is a detailed view of a pair of suction devices 12, 13 being positioned on a heart and spread apart As seen, paddles 22, 27 of each device generally are placed in the area 34 in which temporary immobilization of the heart tissue is desired. When used for a coronary bypass graft, area 34 typically will have a coronary artery 35 running therethrough Area 34 is between paddles 22, 27. Once placed about area 34, suction is then created in the suction ports (not shown in this view.) Through the suction, the device then is fixed to or grabs hold of the heart tissue.

Once the suction is created and the paddles are secured to the heart tissue, each of the suction devices are then spread slightly apart as shown by the arrows 40, 41 to the positions shown as 42, 43. The effect of this spreading apart is to cause a tension to be created in the area 34 of the heart tissue between the paddles. The tension causes the area 34 to be further immobilized, and in particular in the Z-direction, i.e. in the direction normal to the plane defined by the surface of the heart. This is represented in FIGS. 9 and 10.

Figure 9:
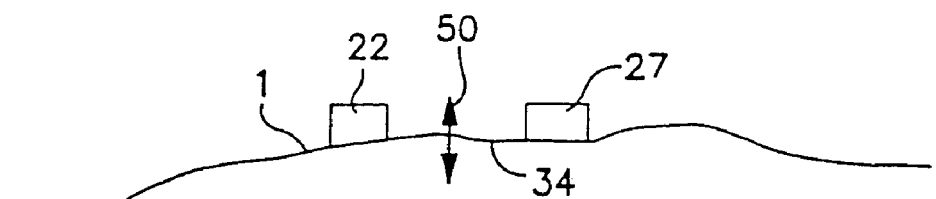
FIGS. 9 and 10 show the effect of the spread-apart motion depicted in FIG. 8.
Figure 10:
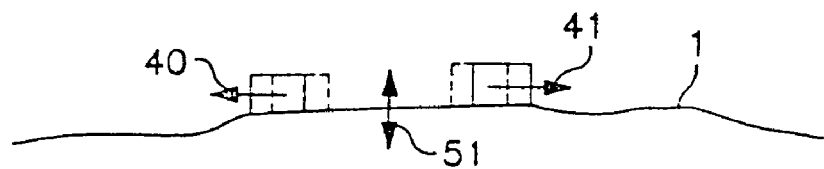

As seen in FIG. 9, the area of heart tissue between the paddles, even with the placement of the paddles, still has some vertical motion, shown here as arrow 50. When paddles 22, 27 are slightly spread apart to cause a tension in that area 34 of tissue between the paddles, as depicted in FIG. 10, then the amount of movement in the area 34 between the paddles 22, 27 due to the tension is further decreased, especially in the Z-direction, i.e. the direction perpendicular to the surface of the heart 1. Once the paddles 22, 27 are thus positioned and secured and the area of the tissue is temporarily immobilized, the coronary artery in that area may be operated upon.

In the preferred embodiment, the anastomosis of the coronary artery may be accomplished through any acceptable end-to-side or side-to-side technique. Of course, other methods of performing the anastomosis may be used, such as those methods which may be performed endoscopically.

Figure 12:
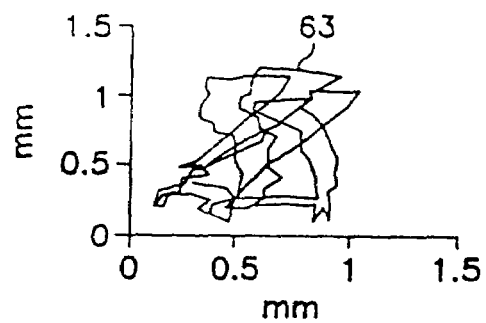
FIG. 12 is an enlarged portion of FIG. 11 depicting the motion of the same point on heart tissue when the suction devices are used.
Figure 11:
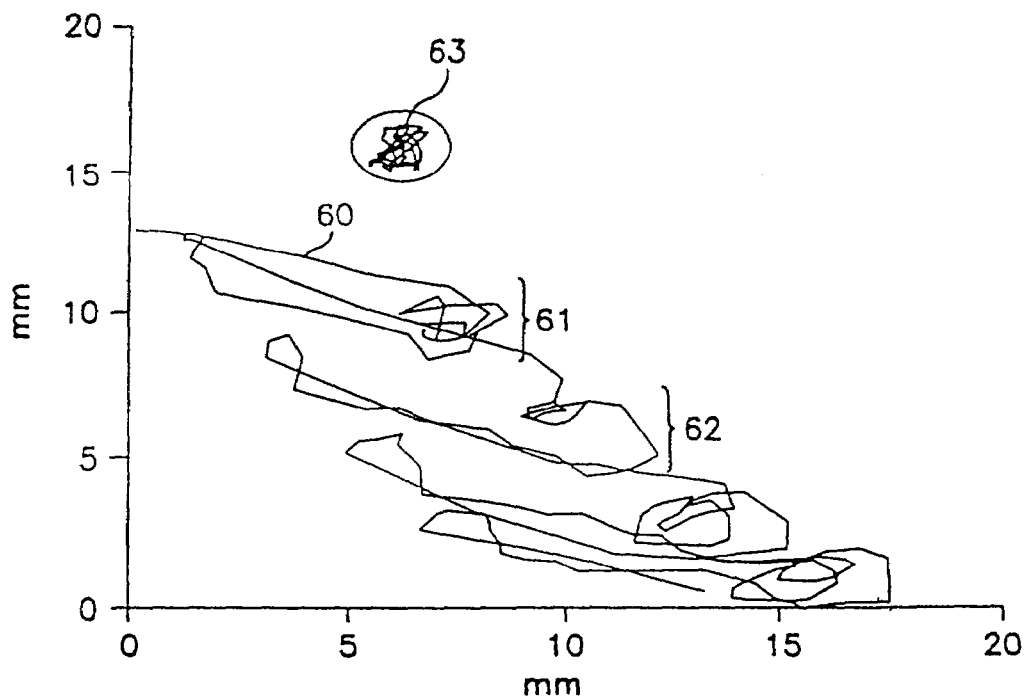
FIG. 11 is an example of the motion in the plane parallel to the surface of the heart of a point on heart tissue during one half respiratory cycle when the heart is unrestrained and also depicting the motion of the same point on heart tissue when the suction devices are used.
Figure 13:
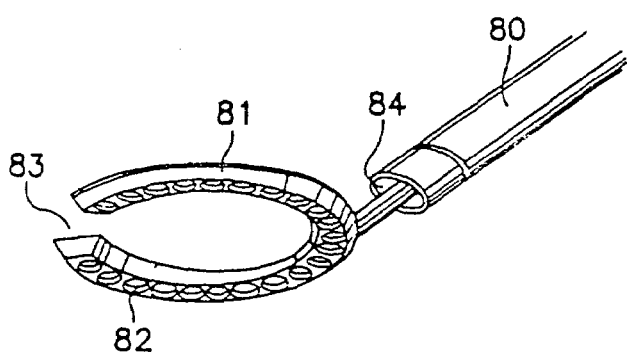
FIG. 13 is an alternate embodiment of the present invention.

FIG. 11 is an example of the motion in the plane parallel to the surface of the heart of a point on heart tissue during one half respiratory cycle when the heart is unrestrained and also depicting the motion of the same point on heart tissue when the suction devices are used. Line 60 is a tracing of the motion of a point of tissue on the cardiac surface. As seen by line 60, a point on the cardiac surface moves approximately 15 mm in each direction. Generally, each loop of movement depicts the motion of the beating heart within one cardiac cycle. Thus, loop 61 occurs due to one cardiac cycle. Loop 62 occurs due to the next cardiac cycle, but the entire heart has shifted in location somewhat due to the inflation or deflation of the lungs associated with respiration. Line 63 shows the motion of the same point of heart tissue when the suction device is placed near the area and the heart wall is immobilized by the present invention. As seen, the present invention functions to minimize heart wall movement in that area to approximately 1 mm in each direction. This is best seen in FIG. 12 which is an enlarged portion of FIG. 11 and in particular line 63. As seen, through the use of the present invention, heart wall movement has been decreased to only slightly more than 1 mm. Decreased to an amount in the area of the suction devices such that the still-beating heart may be operated upon in that area using an endoscope or any other method of minimally invasive surgery FIG. 13 is an alternate embodiment of the present invention. As seen, the embodiment of FIG. 13 comprises a suction sleeve 80 which is coupled to an annular suction head 81 via a ball bearing joint 84. Ball bearing joint 84 may be provided so as to permit remote actuation of the suction head 81 from a position outside the chest. The suction head 81 has a series of suction ports 82 located along a first planar surface. In the embodiment shown the planar surface upon which the suction ports 82 are located is conical in shape, although other types of planar surface may be used, such as frusto-conical for example. The suction head 81 may be constructed such that each half of the device is coupled to a separate suction source. Through such a configuration, if one-half of the suction head 81 were to lose contact with the surface the other one-half of the suction head 81 could maintain capture. The suction sleeve 80 is used as described above. That is the suction sleeve 80 itself is coupled to a suction source (not shown but the same as suction source 114) and is fixed or immobilized to a stationary point, such as the operating table or a retractor false not shown.) Suction through the suction source and the suction sleeve 80 then causes the suction ports 82 to suck upon the heart tissue Through this configuration then the heart tissue in the center of suction sleeve is immobilized. Interruption or opening 83 permits suction head 81 to be fixed to heart tissue while permitting a blood vessel to be grafted. In particular, if a mammary artery has been grafted end-to-side to a coronary artery, then the opening 83 permits the suction head 81 to be removed from around the grafted artery.

Figure 14:
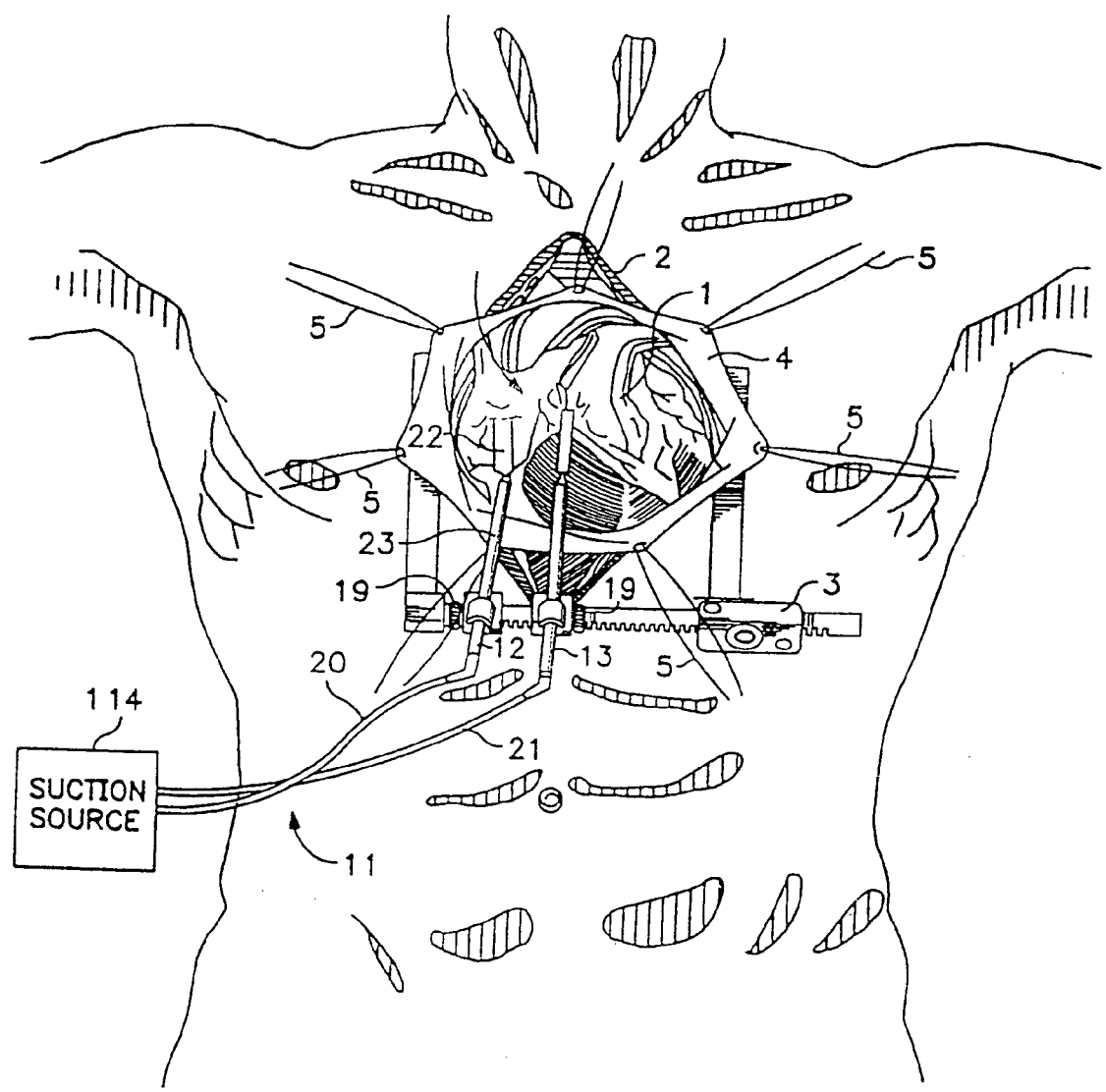
FIG. 14 is a plan view of the device being used to temporarily immobilize a local area of heart tissue in which access to the heart is achieved through a median sternotomy.

FIG. 14 is a view of the device being used to temporarily immobilize a local area of heart tissue using an alternative access procedure to the preferred mini-thoracotomy. In particular heart 1 is exposed with an incision 2 through the patient's sternum and the chest is spread apart by a retractor 3 to provide access to the heart 1. Access to the heart 1 is further effected by retraction of the pericardium 4 in the area of the heart 1 which is to be operated on. As shown pericardial retraction is accomplished through sutures 5.

As seen, the immobilizing device 11 comprises a pair of suction devices 12, 13 and a suction source 114. Suction devices 12, 13 are secured to patient be securing each to retractor 3 through a pair of clamps 19. Of course suction devices 12, 13 may also be secured to the operating table (not shown in this FIG. but using a securing device as described above.) Suction devices are coupled to suction source 114 through lines 20, 21. Suction source 114 is preferably the standard suction available in the operating room and coupled to the devices with a two liter buffer flask (not shown) for each device. Suction is provided at a negative pressure of between 200–600 mm Hg with 400 mm Hg preferred. As seen, each suction device has essentially two portions, a paddle 22 and an arm 23.

Turning now to FIG. 15 which is a side view of an alternate embodiment of suction device 12 showing its placement against the outline of a heart. As seen, the distal end of suction device comprises a paddle 22 and arm 23. Paddle 22 has a generally planar surface which conforms generally to the curvature of a heart 1, shown here in outline. The paddle 22 is coupled to arm 23 through a pin 24. The pin 24 permits the paddle 22 to be swiveled to the preferred angle relative to arm 23. As seen, arm 23 has a suction lumen 30 therethrough which communicates with a suction conduit 31 in paddle 22. Suction conduit 31, in turn, communicates through suction aperture 32 (best seen in FIG. 4) to suction port 33.

FIG. 16 is a view of the bottom of suction device 12 shown in FIG. 15. As seen, four suction ports 33 in a row are featured, although the specific or exact number and position used may vary.

FIG. 17 is a further alternate embodiment of a suction device 12 showing its placement against the outline of a heart. As seen, suction device 12 is substantially similar to that shown and described in FIG. 2, but for the addition of suture coil 73. Suture coil 73 is a tightly wound spring fixed to the top surface of suction paddle 22. Further temporary stabilization of the coronary anastomosis site may be achieved, if desired, by catching epicardial flaps with light traction sutures. Suture coil 73 permits these and any other sutures to be temporarily fixed in place by wedging the suture between within suture coil 73, as is known in the art.

FIG. 18 is a bottom view of a further alternate embodiment of suction device 12 As seen, suction device 12 is substantially similar to that shown and described in FIG. 2, but for the addition of electrode 174 along a side of suction paddle 22. Electrode 174 is coupled by lead 175 to pulse generator 176. Electrode 174, lead 175 and pulse generator 176 may be provided according to well know methods and materials so as to permit the heart to be paced, cardioverted or defibrillated while suction device 12 is fixed to the surface of the heart.

Figure 19:
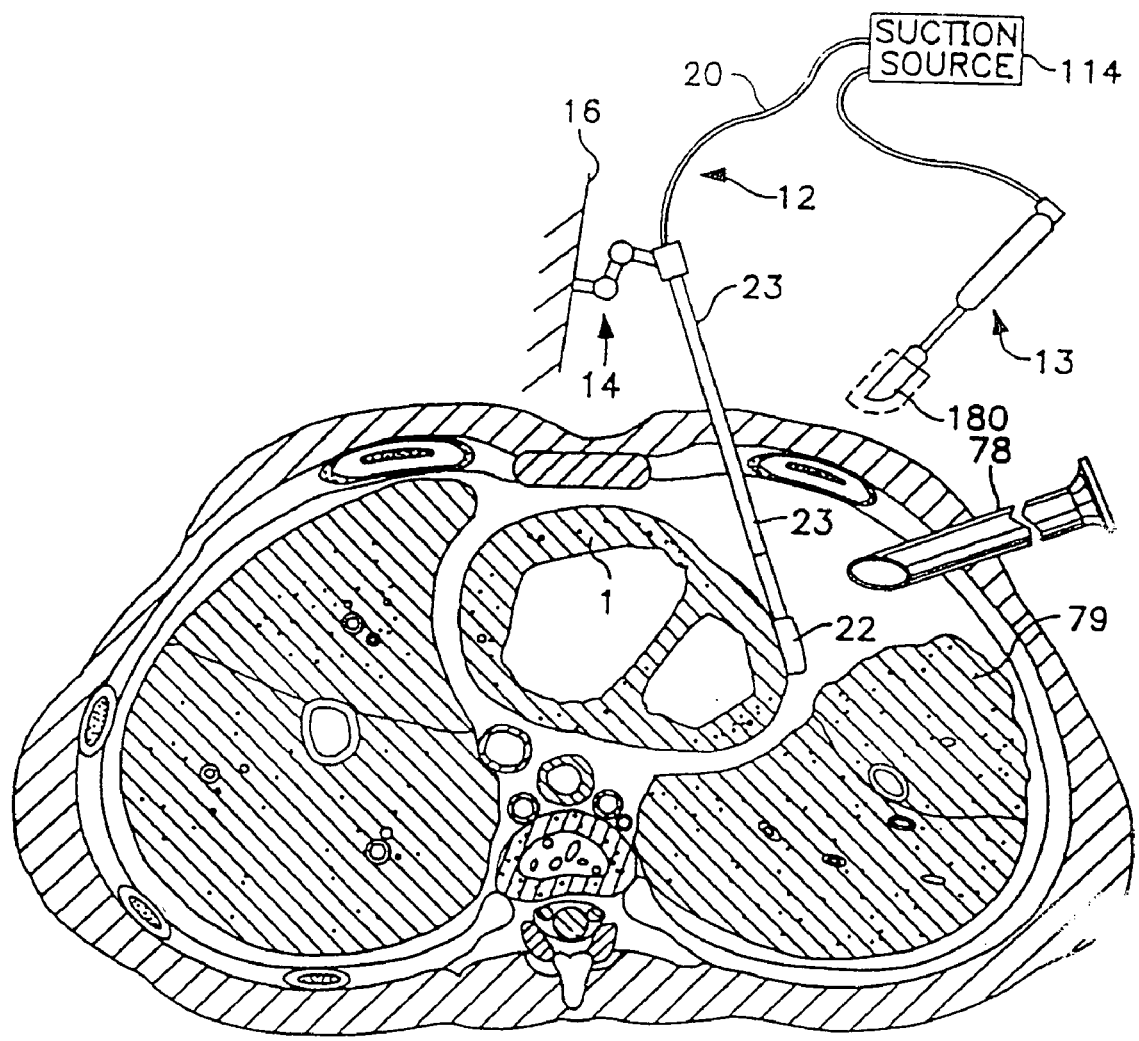
FIG. 19 is a cross-sectional view of a body showing an alternative method of achieving access to the surface of the heart, and in particular of achieving such access using minimally invasive trocars.

FIG. 19 is a cross-sectional view of a body showing an alternate method of achieving access to a surface of the heart and using the present invention to immobilize an area of tissue. As seen suction device 12 is introduced through a first stab wound. As discussed above, suction arm 23 of device 12 is secured by securing device 14 to a stationary object, such as operating table 16. A second suction device may also be introduced through a second stab wound to securely immobilize a local area of tissue. Each suction device has a covering 180, made from latex rubber, over the distal end when it penetrates the chest wall in order to avoid blood and tissue from entering the suction ports and block suction apertures. Two or more additional surgical trocars 78 may be introduced to permit endoscopy and surgical access to heart 1. In addition the left lung 79 may also be partially collapsed so as to provide an unencumbered area in which to manipulate the surgical instruments.

Figure 20A:
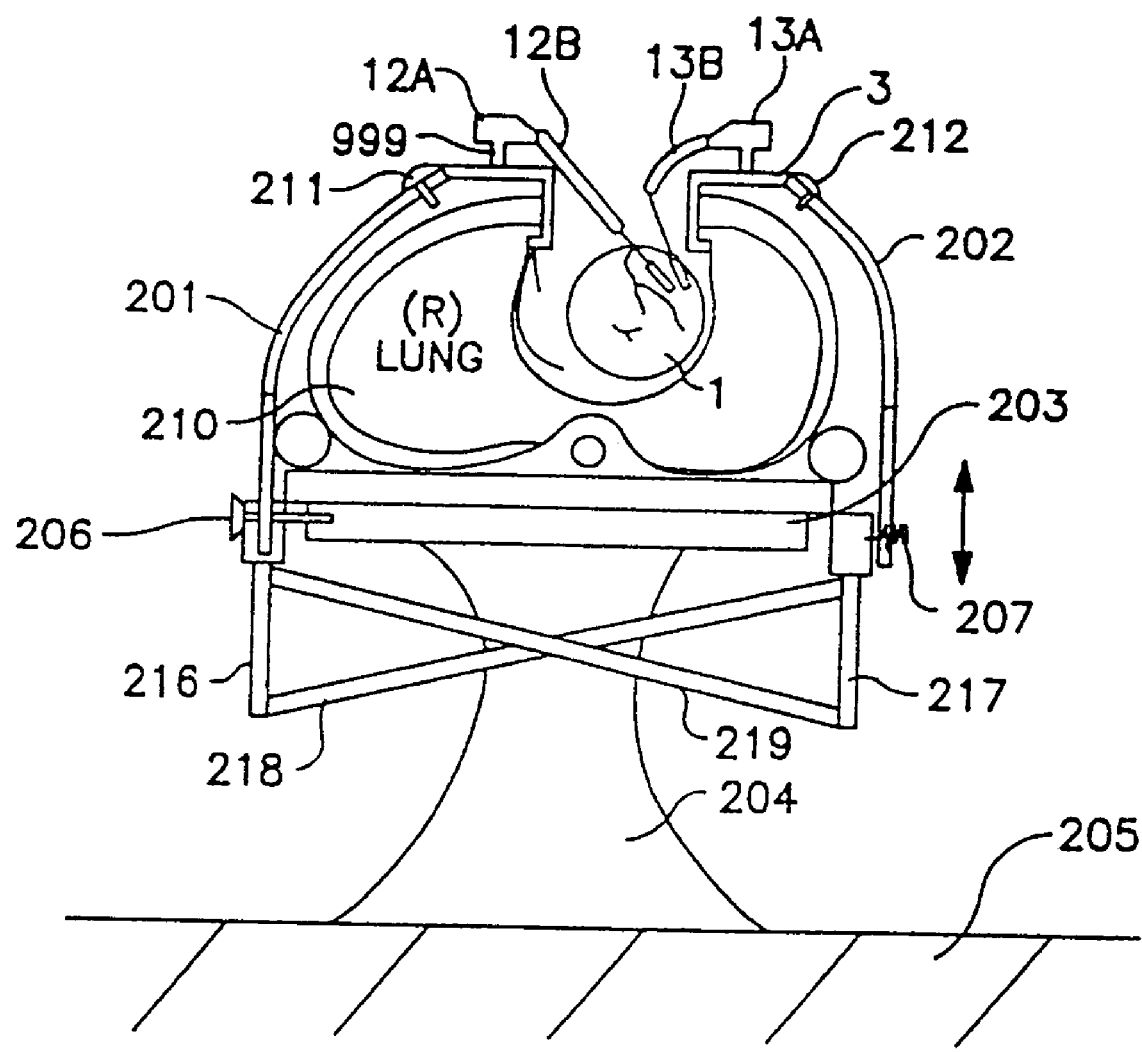
FIG. 20A is a cross-sectional view of a body showing an alternate embodiment of the present invention, and in particular, an alternate embodiment of the securing device.

FIG. 20A is a cross-sectional view of a body showing an alternate embodiment of the present invention, and in particular, an alternate embodiment of the securing device. In this embodiment, securing device comprises a pair of anchors 201, 202 which are attached to surgical table 203 As seen, surgical table is attached by pedestal 204 to the floor 205 Each anchor is attached on either side of the table using a pair of fasteners 206, 207. In the preferred embodiment, fasteners are a pair of screws which couple with longitudinal slots within each anchor to permit the anchors to be adjusted both in an inward and outward direction as well as up and down, as shown by the arrows As seen, anchors are designed to follow the contour of patient 210 to thereby provide a smooth surface over which a surgeon may operate. Each anchor is attached to retractor 3 by fasteners 211, 212. On the retractor 3 a mounting rail 999 is attached, best seen in FIG. 20B discussed below. Attached in turn to mounting rail is a pair of slip-grip type holders 12A, 13A or any other holder which permits an object to be quickly but securely mounted or removed, and mounted in turn to holders are a pair of suction devices 12B, 13B as has been already previously discussed above. In the preferred embodiment, each anchor is a strip of biocompatible metal, such as stainless steel, approximately 5–8 centimeters in width and 0.6–0.8 centimeters in thickness. As seen positioned at the bottom of anchors is a truss. In particular each anchor has fixed to it a descending member 216, 217, each of which are linked together by a pair of cross-braces 218, 219. Cross-braces may or may not be coupled together at their center points. As can be appreciated, through this truss construction the stability of anchors and thus the suction devices mounted thereto is increased.

Figure 20B:
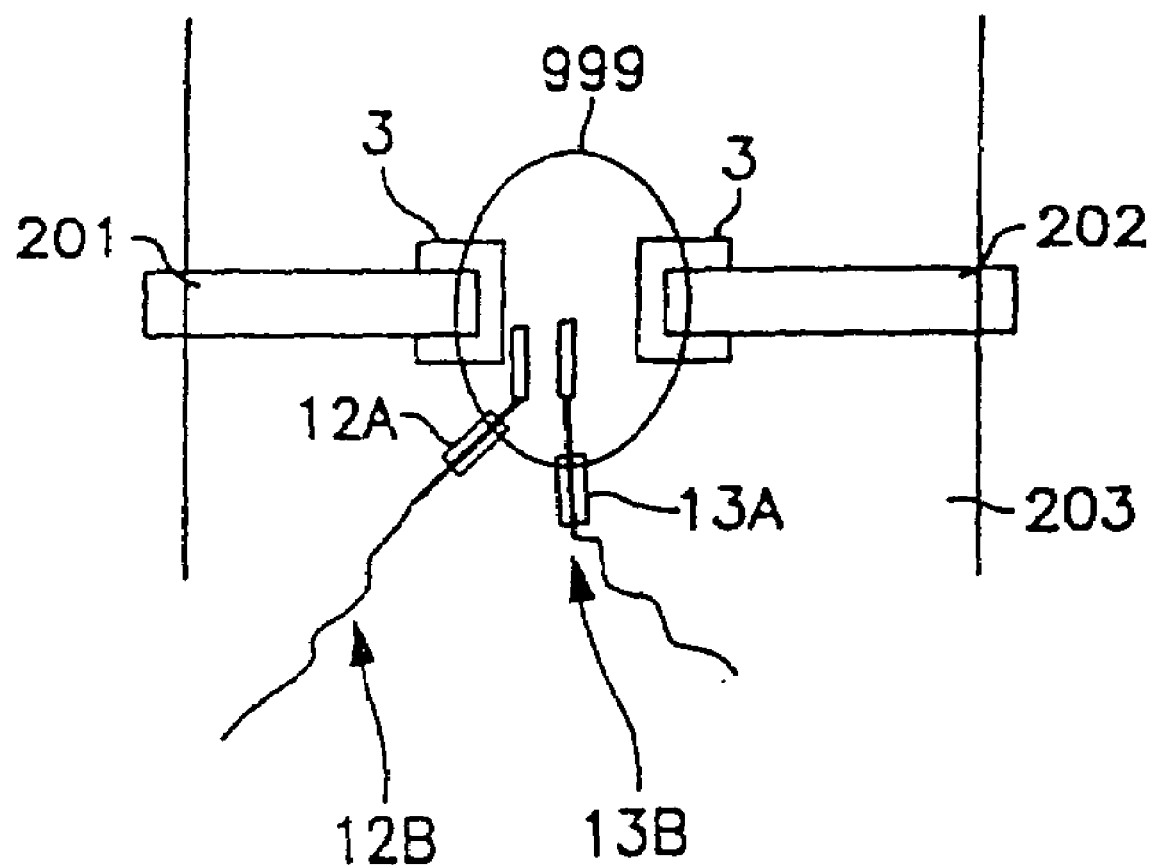
FIG. 20B is a top view of the embodiment shown in FIG. 20A.

FIG. 20B is a top view of the embodiment shown in FIG. 20A. As seen, mounted to anchors 201, 202 is a mounting rail 999 In the preferred embodiment mounting rail is ellipsoidal in shape. As seen mounting rail is used to mount slip-grip type holders 12A, 13A and their corresponding suction devices. To be precise, mounting rail permits the suction devices to be securely mounted but yet be easily moved in the area of the surgical procedure. The ellipsoidal shape, moreover, corresponds more suitably to the surgical area. Of course, other shapes may also be used, such as circular, or non-symmetrical, for example. Of course other configurations of a mounting rail, retractor and anchor may be used, such as a retractor integral with the anchors or a mounting rail integral with the retractor or both, to mention only two of the many possibilities.

In use, access to the heart is achieved and retraction of the chest wall is performed prior to the positioning of the anchors. Once the heart access is achieved, the retractor is coupled to the anchors and the anchors are then fixed to the table. At this point, the retractor is thus immobilized with respect to the table and provides a stationary object to which the immobilizing device featuring the a pair of suction devices 12B, 13B may be coupled.

Figure 21:
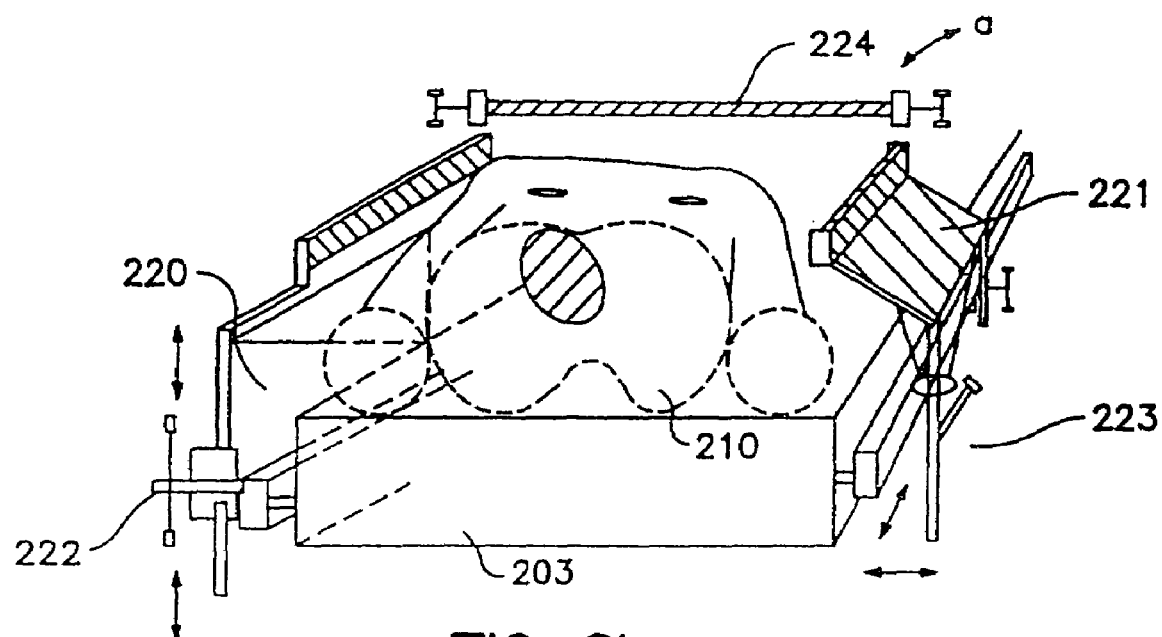
FIG. 21 is a perspective view of a securing device.
Figure 22:
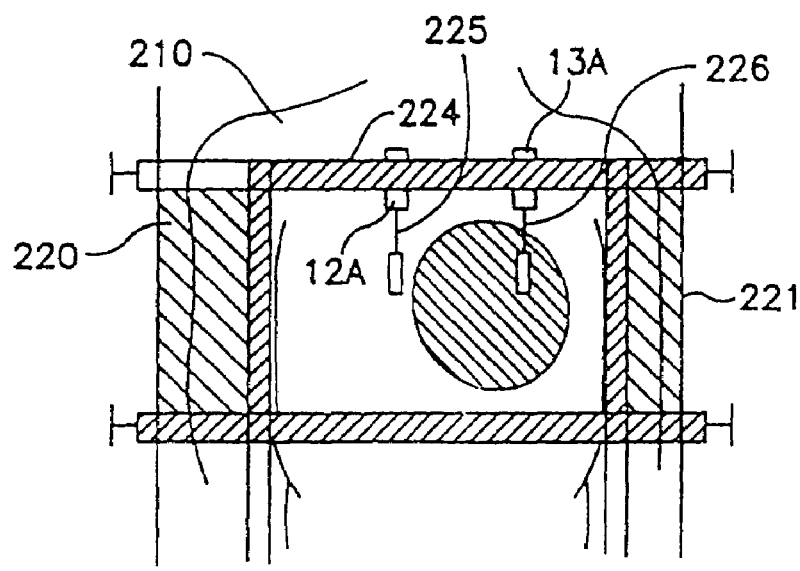
FIG. 22 depicts an overhead view of the securing device.

FIGS. 21 and 22 depict a further alternate embodiment of the securing device. FIG. 21 is a perspective view of a securing device. As seen, in this embodiment, the securing device comprises a pair of formed rails 220, 221. As seen, each rail is coupled to the surgical table 203 through a series of screws 222, 223. Although not shown in the FIGS each rail further features a truss-like structure such as that shown in FIG. 20A which is positioned below the table which provides additional rigidity and stability. As seen, each rail is further formed to slope inwardly toward the patient 210 (shown in outline in this FIG.) This provides for access above the patient by the surgeon. Straddling between each rail is a mounting 224. The mounting is adjustable along the rail. The mountings are further designed to have a suction device mounted thereto. In such a manner, the mounting 224 and rails 220, 221 provide a stationary object to which the suction device may be mounted.

FIG. 22 depicts an overhead view of the rails 220, 221 used to position a suction device to the heart. As seen, in this embodiment, two suction devices 225, 226 are fastened to the mounting using a pair of slip-grip type holders 12A, 13A as already discussed above.

Figure 23:
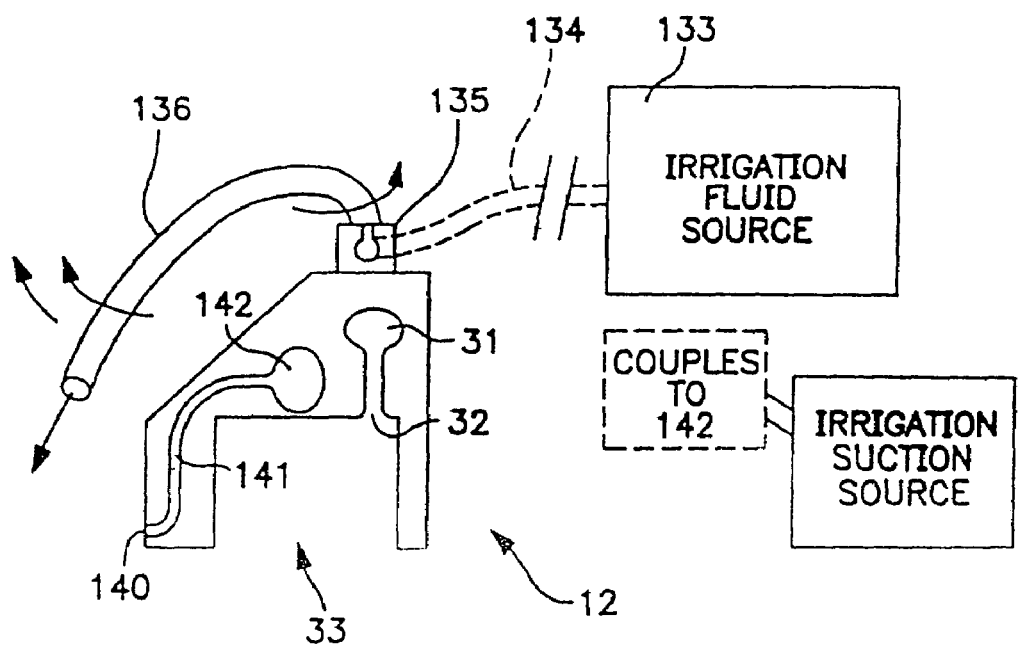
FIG. 23 is a side view of an alternate embodiment of suction device.

Turing now to FIG. 23 which is a side view of an alternate embodiment of suction device 12. As seen this alternate embodiment of suction device 12 features a suction port 33 as already described above. Each suction port is connected to a suction conduit 31 through a suction aperture 32 as also already described above. In this embodiment, however, the suction device further provides for the distribution of irrigation fluid onto the area of the heart where an anastomosis will be performed. As seen, the irrigation fluid source 133 is coupled by an irrigation line 134 to the irrigation fluid conduit 135. The irrigation fluid conduit, in turn, is coupled to an irrigation hose 136. As shown, irrigation hose is designed to have some flexibility to permit it to be rotated and moved along several angles and is preferably a braided stainless steel hose. Irrigation hose dispenses irrigation fluid at its end. Irrigation fluid preferably is a warm saline mist which prevents the exposed tissues from drying out. Moreover, the fluid is dispensed under pressure such that the mist has a force to it which permits the mist to be used to blow with sufficient force to assist in holding open a coronary artery such that the anastomosis may be performed more easily. Suction device further features a return irrigation fluid circuit. As seen, return irrigation fluid circuit comprises a return irrigation port 140 which is coupled to a return irrigation conduit 141. Return irrigation conduit is coupled to a suction source to provide suction to return irrigation pipe 142 such that the irrigation fluid which is dispensed may be readily removed from the surgical area. Although shown as an integral part of the suction device, both the irrigation system as well as the suction system may or may not be a part of the suction device.

Figure 24:
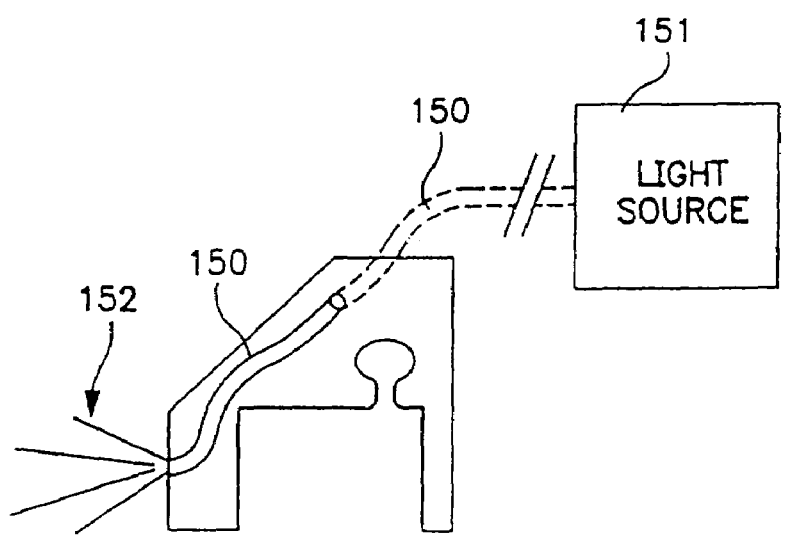
FIG. 24 is a further alternate embodiment of a suction device.

FIG. 24 is a further alternate embodiment of a suction device. As seen, suction device features the suction port, suction conduit and suction aperture as already described above. In this embodiment, however, the suction device further features an optical fiber 150 which is coupled at one end to the area of the suction device where the anastomosis will be performed and is further coupled to a light source 151. In this manner, the suction device may be used to provide additional light 152 to the area where the anastomosis will be performed.

Figure 25:
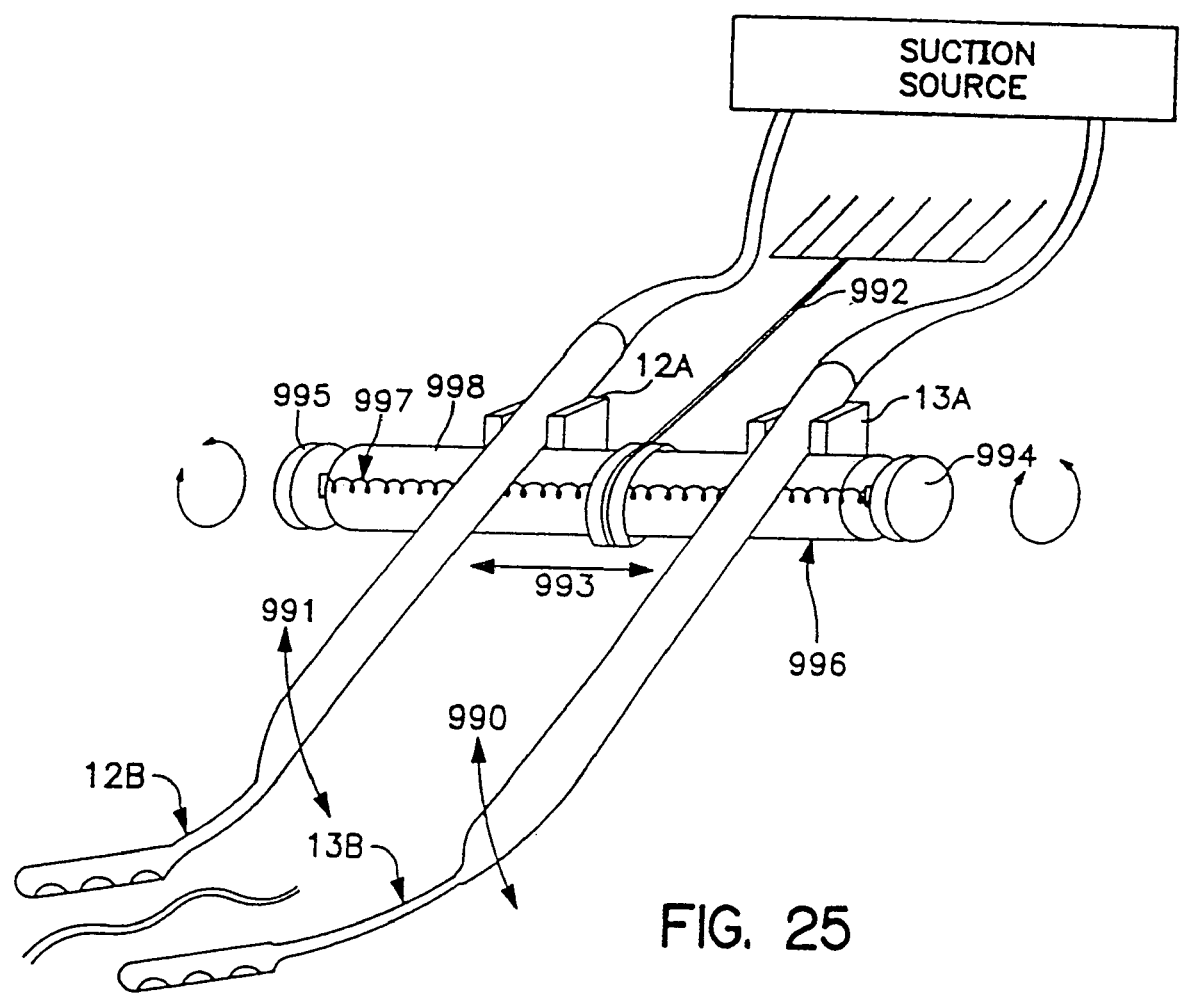
FIG. 25 is a perspective view of an alternate embodiment of an immobilizing device.

FIG. 25 is a perspective view of an alternate embodiment of an immobilizing device 11. As seen, in this embodiment, each suction device is coupled to a mounting beam 998 through a pair of holders 12A, 13 A as already described above with reference to FIG. 20A. Mounting beam 998 features two sections, each of which may be individually rotated about or spread apart or both. In particular mounting beam has a central screw members 997, 996. Each central screw member has an actuating knob 994, 995 at an end thereof. Rotation of each knob thereby causes the suction device mounted to that portion of the mounting beam to move either away or towards the center of the mounting beam, as indicated by line 993. Mounting beam 998 is mounted to a stationary object, such as a retractor, mounting rail or fixation arm through a central arm 992. Each suction device may further be rotated relative to the mounting beam through simply moving each of the relevant devices, as indicated by the lines 991, 990. The use of mounting beam to retain suction devices is of use when only one fixation arm is to be used. In such a manner mounting beam permits both device to be fixed to a stationary object as well as permitting suction devices to be moved apart to thereby provide additional immobilization to a local area of tissue as discussed above with regards to FIGS. 8–10.

FIG. 26A is a view of the bottom of an alternate embodiment of suction paddle 22 used in the immobilizing device As seen, paddle has a series of suction ports, each of which is connected to suction conduit through a suction aperture. In this embodiment, the paddle features five suction ports. The additional side suction port is presented on the side of the suction paddle which will not be near the coronary artery or, in general, the surgical target. The additional port increases the suction surface area. Each suction port 33 has a 6 mm diameter while each suction aperture 32 has a 2 mm diameter.

FIG. 26B is a perspective view of the bottom of an alternate embodiment of suction paddle 22 used in the immobilizing device. As seen in this embodiment the paddle 22 is oriented at a ninety degree angle relative to the neck portion 71 and arm 23. Of course paddle may also be oriented at another suitable angle other than ninety degrees relative to neck portion. In this embodiment, the paddle features four suction ports, although more or less ports may also be provided. Each suction port 33 has a 6 mm diameter while each suction aperture 32 has a 2 mm diameter.

Figure 27:
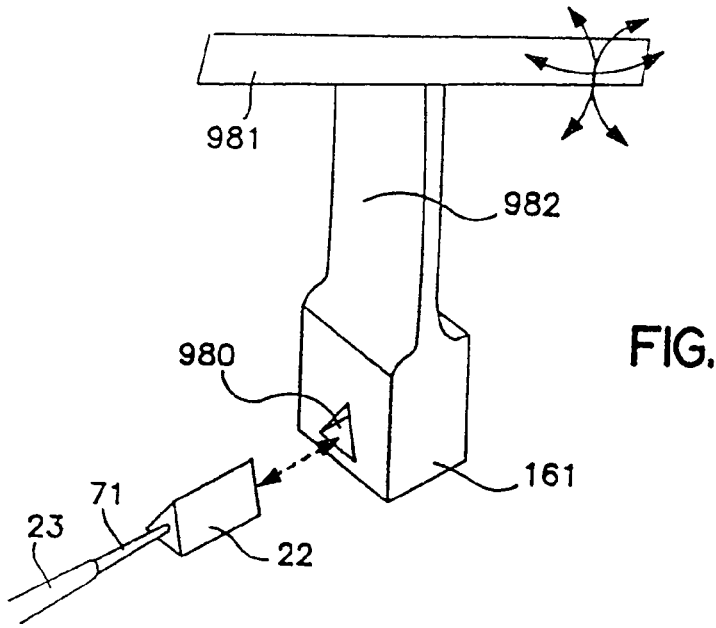
FIG. 27 is a perspective view of a turning handle used to bend or orient the suction paddle portion of the immobilizing device.

FIG. 27 is a perspective view of a turning handle 161 used to bend or orient the suction paddle 22 portion of the immobilizing device. As discussed above neck 71 is fashioned to be relatively bendable, as opposed to paddle 22 and arm 23. As seen, handle 161 features opening 980 having the same shape and dimension of paddle such that paddle may thus be inserted therein. Handle also features neck portion 982 and grip portion 981, Neck and grip portion are dimensioned to provide leverage against opening 980 and thus paddle, neck and arm. To use, paddle is inserted into opening. Once inserted manipulation of grip portion relative to arm causes bending in the area of neck. Such a handle may be advantageous as compared to bending of the device by hand in that it avoids the surgeon from straining hand muscles which will be needed to perform delicate manipulations.

Figure 28:
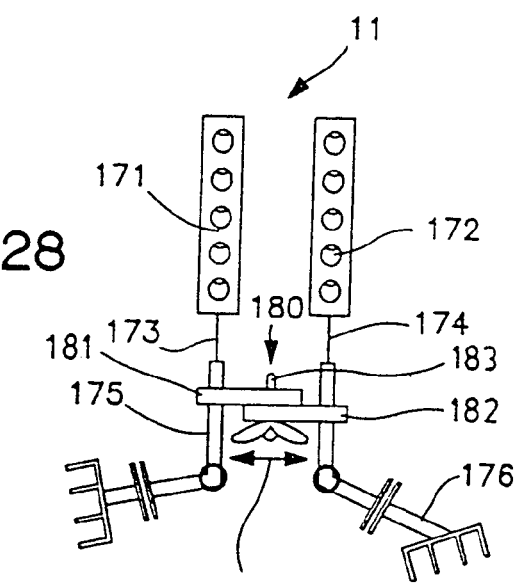
FIG. 28 is a bottom view of an alternate embodiment of immobilizing device.

FIG. 28 is a bottom view of an alternate embodiment of immobilizing device 11 As seen, immobilizing device features a pair of suction paddles 171, 172, each of which is coupled to an arm by a continuous hinge or neck as discussed above The arm in turn, is coupled to a stationary object, also discussed above. In this embodiment, the arms are further fastened together using a spreader 180. As seen, spreader 180 permits the arms to be moved relatively apart or together. As already discussed above, the movement of the arms apart is performed once the paddles are engaging by suction the surface of the heart to thereby increase epicardial tension locally and thus dampen or decrease the motion of the surface of the heart due to the intrinsic beating of the heart. Spreader also functions to provide additional stability to paddles due to its function as a truss-like member.

Figure 29:
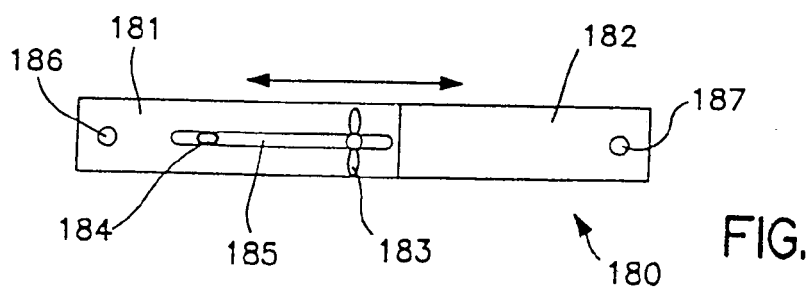
FIG. 29 is a plan view of a spreader used in an alternate embodiment of the present invention.

Turning to FIG. 29, spreader 180 comprises a pair of bars 181, 182 which are coupled together using a wing nut 183. One bar features an engagement pin 184 while the other bar features an engagement slot 185. Each bar is further coupled to each of the respective arms of the immobilizing device by a respective lumen 186, 187. In such a manner, each bar is securely coupled to each arm. By longitudinally manipulating each of the bars apart as shown by arrow 188, each arm and thus each paddle may be securely positioned relatively closer or further apart.

Figure 30:
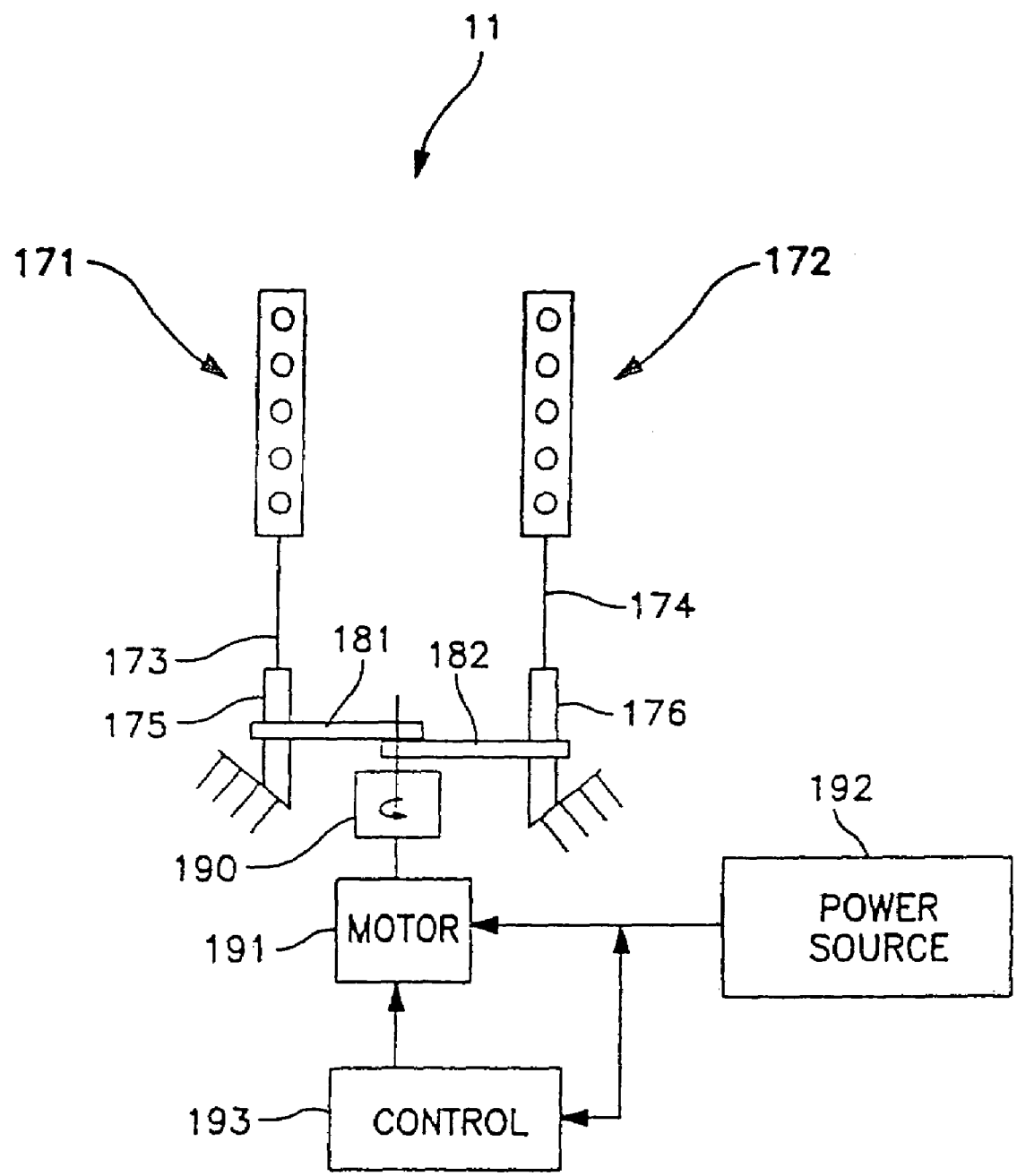
FIG. 30 depicts an alternate embodiment of spreader.

FIG. 30 depicts an alternate embodiment of spreader 180. As seen, spreader features a pair of bars which couple to each of the arms of a respective suction device, as described above. Bars are further coupled together using gearing 190. Gearing, in turn, is coupled to a motor 191 As seen, motor is further coupled to a power source 192. Coupling both motor and power source together is a control 193. Control automatically detects the amount of spread within the suction devices caused by spreader. In the preferred embodiment, control senses the amount of power or energy required by motor to further spread spreader and thus suction paddles apart. When a threshold amount is reached, control shuts down the source of power for motor, thereby locking the spreader in the present position. The feature thus permits a spreader to automatically spread the suction paddles apart to a degree sufficient to dampen wall motion without permitting the spreader to spread paddles apart too much such that capture of the heart wall due to suction is lost. Of course, further designs to control the spreading of suction paddles may also be used, such as other mechanical or hydraulic actuated or controlled systems.

Figure 31:
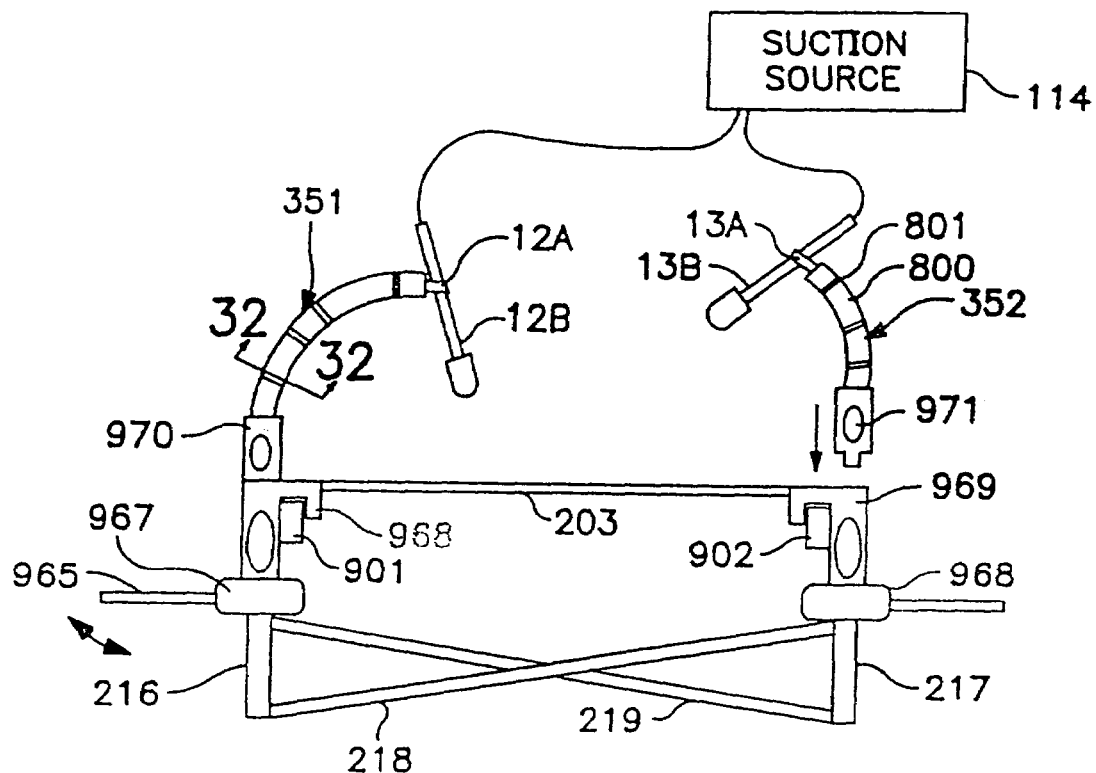
FIG. 31 depicts an alternate embodiment of immobilizing device and, in particular, an alternate embodiment of the securing device used to secure each suction paddle to the operating table rail.

FIG. 31 depicts an alternate embodiment of immobilizing device and, in particular, an alternate embodiment of the securing device used to secure each suction paddle. As seen this system features a pair of arms 351, 351 having a ball and socket construction. As seen each arm features at its free end a slip and grip-type holder 12A and 13A as discussed above. The opposite end of each arm fits into a footing 970, 971. Each footing is lockable to a rail clamp unit 968, 969 which locks onto the rail 901, 902 at the side edges of table 203. Positioned at the bottom of rail clamp unit is locking actuator 967, 968. Each locking actuator cooperates within the arm to thereby cause the arm to be locked into position when the respective handle is turned in one of the directions indicated by arrows 965. In particular locking actuator causes a cable located with the respective arm to tighten, which, due to the ball and socket construction thereby causes the arm to be locked into position. Positioned at the bottom of each locking actuator is a truss. In particular each locking actuator has fixed to it a descending member 216, 217, each of which are linked together by a pair of cross-braces 218, 219. Cross-braces may or may not be coupled together at their center points. As can be appreciated, through this truss construction the stability of anchors and thus the suction devices mounted thereto is increased, as described earlier in FIG. 20A.

Figure 32:
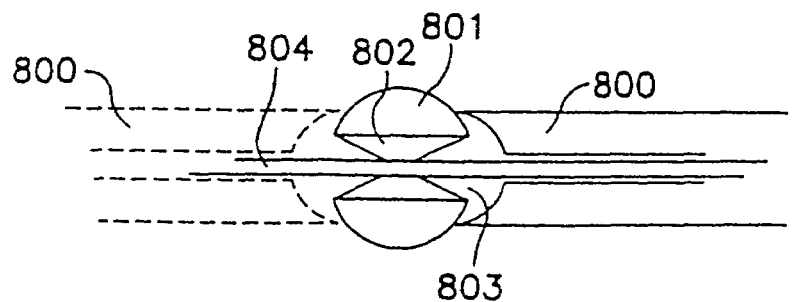
FIG. 32 is a cross sectional view of the arm shown in FIG. 31.

FIG. 32 is a cross sectional view of an arm shown in FIG. 31, and in particular showing a detail of the ball and socket construction. As seen only one portion is shown to illustrate the ball and socket construction. Each tube 800 (several of which are used to create arm) has its end fashioned to correspond to the shape of the ball 801, that is each relevant end of tube features a hemispherical hollow having a radius which corresponds to the outer surface of the ball such that a larger portion of the tube contacts the ball as compared to if the end of the tube were only cut straight across. This geometry increases the surface area between the tube and each ball which thereby increases the stability of the arm when fixed into position. Each ball 801 further features an internal bushing 802. As seen each internal bushing is shaped to have a tapered opening 803 at each end. Positioned through the length of arm, and in particular within each tube element and ball is cable 804. Cable is preferably constructed from kevlar and features a polyurethane covering and is fastened to either end of the arm such that by tensioning the cable the ball and tube portions are brought together and fixed in relation due to friction. The operation of arm is as follows. When no tension is placed on the cable, each tube element may slip relatively easily relative to each ball. Tension on the cable, however, increases the friction between tube and ball. Sufficient tension thereby results in the ball and tube becoming immovable relative to each other. The taper 803 within each bushing 802 permits the cable to remain at the same length regardless of the orientation of each tube element and each ball. That is, if the arm is bent and has a radius of curvature, the taper permits the cable to remain at the same length regardless. This thus permits the arm to be more easily moved and thereafter locked into place.

Figure 33:
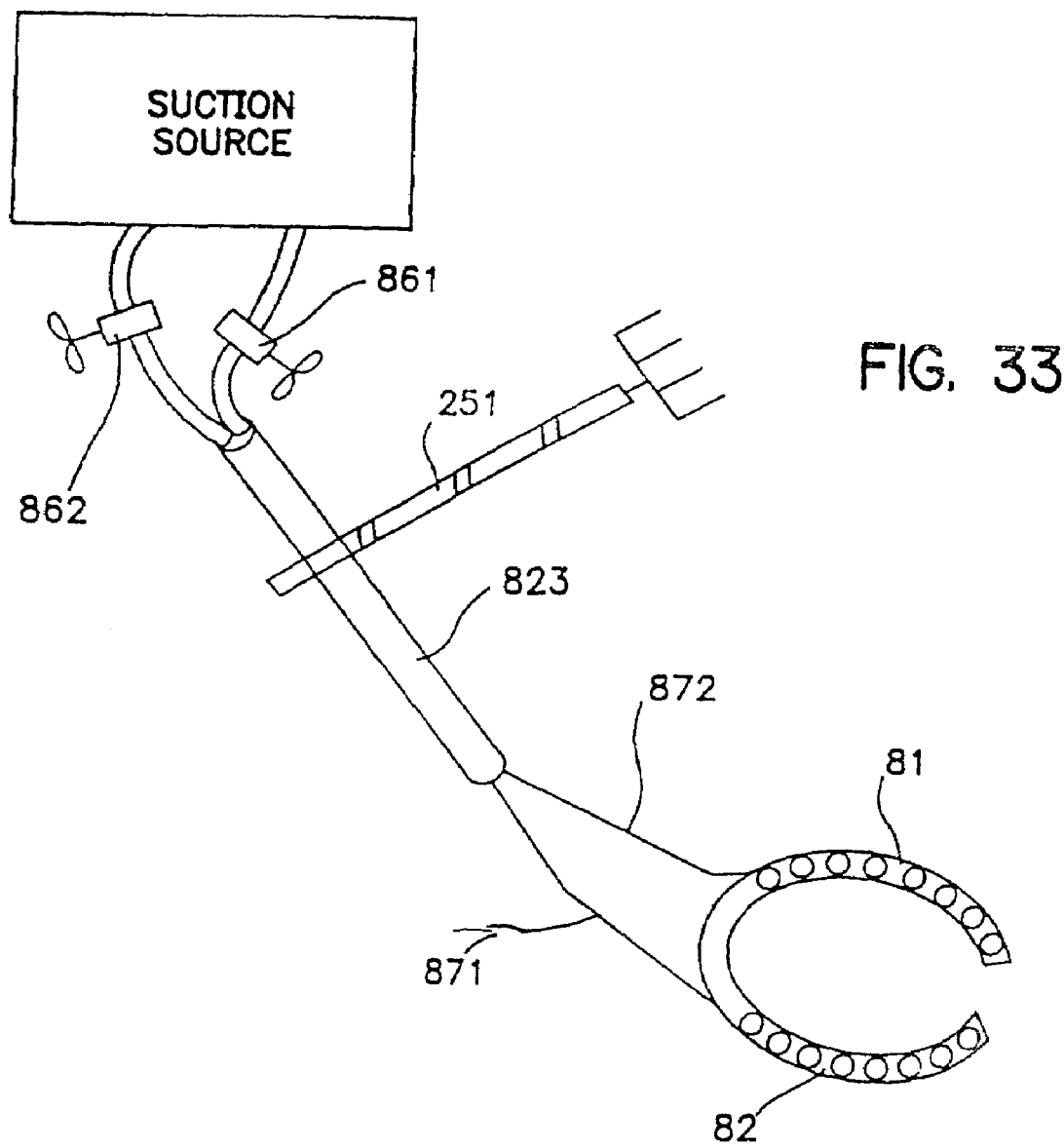
FIG. 33 depicts a further alternate embodiment of the present invention, and in particular of a suction device substantially similar to that shown in FIG. 13 but for that the suction ports are located at the top of the suction paddle.

FIG. 33 depicts a further alternate embodiment of the present invention, and in particular of a suction device substantially similar to that shown in FIG. 13 but for that two separate sets of suction ports are located at the top of the suction paddle. As seen each suction line has a stopcock 861, 862 to permit either or both sets of related suction ports to be independently disconnected from their respective suction source. Arm 823 contains lumens for each suction line and ends where necks 871, 872 begin, As discussed above, each neck is designed to bend. Suction paddle is mounted to necks and as seen features an encircling array of suction ports, located at the upper surface of the paddle relative to the arm. Suction paddle features sixteen suction ports, arranged as a set of eight along one side 81 coupled to one suction line and a second set of eight along another side 82 coupled to another suction line. Through this arrangement even if one side loses capture with the tissue, because the other side is coupled to another suction source, pressure is not lost on that side and capture in that area is maintained. In the embodiment shown the suction ports are located along a generally conical planar surface at the top of the paddle, although other types of planar surfaces may be used, such as frusto-conical for example. The orientation of the suction ports along the top of the encircling paddle is most useful to access the posterior or backside of the heart so as to move or reposition the heart to achieve better access to areas which would otherwise be difficult to access.

To further assist in the exposure of the surgical site, access retractors may also be used in conjunction with the immobilizing device, such as spoon shaped probes to move other tissue from the area of surgical interest.

Figure 34:
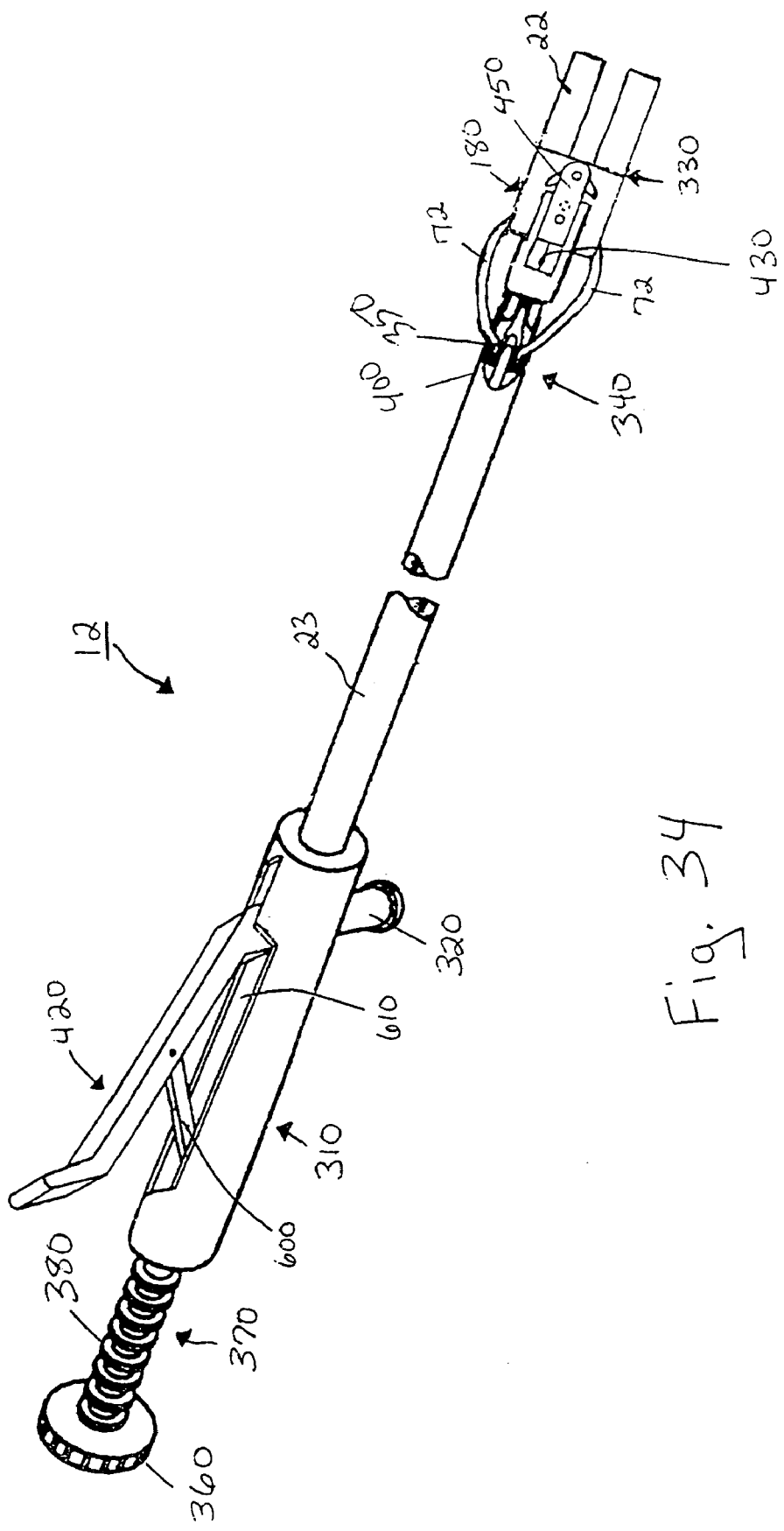
FIG. 34 depicts a further alternate embodiment of the present invention, and in particular of a suction device that may be used in an endoscopic procedure featuring an arm, and a pair of tissue engaging members and a spreader.

FIG. 34 depicts a further alternate embodiment of the present invention, and in particular of a suction device 12 that may be used in an endoscopic procedure featuring at its distal end an arm, i.e., suction arm 23. and a pair of tissue engaging members, i.e., suction paddles 22, each of which is coupled to a spreader means, i.e, spreader 180. The distal end of suction device 12 is suitably configured for delivery through a small, percutaneous penetration, for example a small cut, incision, stab wound, hole, port, cannula, trocar sleeve or the like. The term "trocar sleeve" appearing herein also refers to cannulae and ports. Suction arm 23 of suction device 23 has a proximal end and a distal end. Although suction arm 23 is shown as having a circular cross-sectional shape, suction arm 23 may alternatively have a rectangular, triangular, oval or channel cross-sectional shape. As shown in FIG. 34, suction device 12 also features a handle 310 located at its proximal end. Suction device 12 may be coupled to a suction source 114 through suction line 20 (both not shown) to suction fitting 320 located on handle 310. Suction paddles 22 may be rigidly coupled to spreader 180 at 330, as seen in FIG. 34. Alternatively, suction paddles 22 may be rotatably or pivotably coupled to spreader 180 at 330, thereby permitting suction paddles 22 to freely or controllably move or rotate relative to spreader 180.

Spreader 180 may be rigidly coupled to suction arm 23 at 340. Alternatively, spreader may be rotatably or pivotably coupled to suction arm 23 at 340, thereby permitting spreader 180 to freely or controllably move or rotate relative to suction arm 23. As seen in FIG. 34, in this embodiment of the invention, spreader 180 may be controllably moved relative to suction arm 23 since spreader 180 is coupled to suction arm 23 via remotely actuable linkage 350. Actuator knob 360 on handle 310 is used to remotely and controllably actuate linkage 350. Knob 360 is fixed to rod 370. The proximal end of rod 370 is threaded at 380 so that rod 370 mates with a threaded inner bore (not shown) within handle 310. Rotation of knob 360 moves knob 360 and rod 370 in an axial direction with respect to suction arm 23.

As seen in FIGS. 35 and 36 which are longitudinal cross-sectional views of the distal end of suction device 12, linkage 350 comprises longitudinal rod 390 slidably disposed within suction arm 23 and a link 380 having a first and second ends 381, 382. The proximal end of rod 390 (not shown) is connected to the distal end of rod 370 within handle 310. Linkage 350 further comprises a coupling member 383 which has a bifurcated proximal end with first and second coupling points 384 and 385. First end 381 of link 380 is coupled to the distal end of rod 390 and second end 382 of link 380 is coupled to coupling member 383 at coupling point 385. Suction arm 23 has an angled opening 400 (as seen in FIGS. 34, 35 and 36) at its distal end to allow spreader 180 to pivot into an orientation transverse to suction arm 23. Second coupling point 384 of coupling member 383 is pinned to distal end of suction arm 23 to form a pivot point 410. Spreader 180 which is connected to coupling member 383 will therefore pivot about a transverse axis through pivot point 410.

In the above described configuration, rotation of knob 360 moves rod 370 in an axial direction with respect to suction arm 23. Axial movement of rod 370 causes rod 390 to also move in an axial direction with respect to suction arm 23. Movement of rod 390 in the axial direction with respect to suction arm 23 controllably pivots spreader 180 and suction paddles 22 about pivot point 410, thereby allowing a surgeon to remotely control the orientation of suction paddles 22 relative to suction arm 23. Note that handle 310 may alternatively include another type of actuator mechanism to remotely control linkage 350, for example, a plunger mechanism, a pair of scissor-type handles, a lever mechanism, or a slidable button within a longitudinal slot. The actuator mechanism may be, for example, voice-activated comprising voice-recognition technologies. A visual and/or audible signal, such as a flashing light and/or beeping tone, may be incorporated to alert a surgeon to the completion or resumption of the actuator. Linkage 350 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

Referring again to FIGS. 35 and 36, suction paddles 22 are shown in this embodiment to comprise a series of three suction ports 33 each of which is connected in fluid communication to suction conduit 31 through suction aperture 32. Note that the exact number, position and/or size of suction ports 33 may vary. Each suction conduit 31 is connected in fluid communication to suction lumen 30 located within suction arm 23 through a separate suction line 72. Suction lumen 30 is connected in fluid communication to suction fitting 320 located on handle 310. Therefore, when suction fitting 320 is connected to a suction source 114 through suction line 20 (both not shown), suction is created in suction ports 33. Note that suction device 12 may include a suction controller, for example, handle 310 may include a suction controller (not shown) to control the amount of suction at suction ports 33. Suction controller may be, for example, a valve. Suction controller may also be, for example, voice-activated comprising voice-recognition technologies. A visual and/or audible signal, such as a flashing light and/or beeping tone, may be incorporated to alert a surgeon to the completion or resumption of suction. Suction controller may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

In this embodiment, suction paddles 22, suction ports 33, suction apertures 32 and suction conduits 31 are all generally similar to those previously described. Suction device 12 may be constructed such that each suction paddle 22 and/or each suction port 33 is coupled to a separate suction source allowing them to be independently disconnected from their respective suction source or suction device 12 may be constructed such that each suction paddle 22 and/or each suction port 33 is coupled to the same suction source, as described in this embodiment.

In FIGS. 35 and 36, suction paddles 22 are shown to have a surface which contacts a heart slightly curved such that the surface will conform generally to the curvature of the heart. Heart contacting surfaces of suction paddles 22 may also be generally planar. The heart contacting surfaces of suction paddles 22 may have a separate contact layer to cushion the contact between the paddles and the heart tissue and to facilitate forming a tight seal when suction is applied. The contact layer may cover substantially the entire bottom surface proximate to the openings of the suction ports. The contact layer may comprise of one or more materials, for example, commercially available polymers, such as silicon or polyurethane, which are pliable and biocompatible may be used. In addition, one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may also be used.

It should be understood that suction paddles 22, i.e., tissue engaging members, may comprise a variety of shapes and configurations so long as they have a relatively rigid portion with a contact or coupling surface suitable for engaging tissue. In fact, in this embodiment of suction device 12 comprising spreader means 180, friction paddles may be used in place of suction paddles. Friction paddles may also be rigidly, rotatably or pivotably coupled to spreader 180. Friction paddles may have a contact or coupling surface suitable for engaging tissue frictionally, for example, the contact surface may comprise a rough surface. Further, in this embodiment of suction device 12 comprising spreader 180, adhesive paddles may be used in place-of suction paddles. Adhesive paddles may also be rigidly, rotatably or pivotably coupled to spreader 180. Adhesive paddles may have a contact or coupling surface suitable for engaging tissue adhesively, for example, the contact surface may comprise a tissue adhesive.

FIG. 37 is a bottom view of spreader 180 with coupled suction paddles 22 in a non-spread position, whereas FIG. 38 is a bottom view of spreader 180 with coupled suction paddles 22 in a spread position. As seen in FIGS. 37 and 38, in this embodiment of the invention, suction paddles 22 are attached to spreader 180 such that suction paddles 22 are oriented parallel to each other. Cable 430 extends between spreader 180 and handle 310 through suction arm 23. The proximal end of cable 430 is connected to actuator lever 420 on handle 310. The distal end of cable 430 is connected to spreader 180. Lever 420 is used to remotely and controllably actuate spreader 180 as described below.

As shown in FIGS. 37 and 38, cable 430 passes through anchor 440 and is coupled to slide 450 which is slidably coupled to anchor 440. Cable 430 may be made of stainless steel. Referring to FIGS. 39 and 40, plan views of spreader members 460, 470 are shown with a suction paddle 22 rigidly coupled to each at 330. As previously discussed, suction paddles 22 may be rigidly coupled to spreader members 460, 470 at 330 or, alternatively, suction paddles 22 may be rotatably or pivotably coupled to spreader members 460, 470 at 330, thereby permitting suction paddles 22 to move or rotate relative to spreader members 460, 470. Spreader members 460, 470 include first, second and third slots 471, 472, 473 with the second slot 472 being oriented substantially perpendicular to the suction paddles 22. The second slot 472 of spreader members 460, 470 are aligned so that a pin passing through the second slots 472 helps maintain suction paddles 22 parallel to one another throughout movement between a non-spread and a spread position. The first and third slots 471, 473 of each of spreader members 460, 470 are parallel to one another and oriented 45 degrees relative to the suction paddles 22. Referring to FIG. 37, first, second and third pins 475, 476,477 pass through the first, second and third slots 471, 472, 473.

Referring to FIGS. 41 and 42, side and plan views of slide 450 are shown. Slide 450 includes throughhole 480 for receiving cable 430. The distal end of cable 430 preferably has an anchor (not shown) which prevents withdrawal of cable 430 through throughhole 480. Slide 450 includes first and second holes 481, 482 extending through first and second sides 483, 484. The first and third pins 475, 477 extend through first and second holes 481, 482 of slide 450 and first and third slots 471, 473 of spreader members 460, 470 for moving spreader members 460, 470 when slide 450 is moved. Slide 450 also includes grooves 490 extending between the first and second holes 481, 482.

Referring to FIGS. 43 and 44, side and plan views of anchor 440 are shown. Anchor 440 includes central guides 500 which are positioned in grooves 490 of slide 450. Central guides 500 and grooves 490 cooperate to help maintain the linearly slidable relationship between slide 450 and anchor 440. Central guides 500 also include holes 501 therethrough for receiving the second pin 476 which extends through second slots 472 in spreader members 460, 470. Anchor 440 includes throughhole 502 for receiving cable 430. Proximal end 510 of anchor 440 includes four arms 515, three of which are shown in FIGS. 43 and 44, which extend between central guides 500 and proximal end 510. Referring again to FIG. 35, anchor 440 of spreader 180 is connected to coupling member 383 of linkage 350.

Referring to FIGS. 34 and 45, actuation of lever 420, comprising a slidable member 600 within a longitudinal slot 610 in handle 310, controllably moves cable 430 and slide 450 proximally relative to suction arm 23. Cable 430 is connected to the end of slidable member 600 within handle 310. Actuation of lever 420 causes the slidable member 600 to move cable 430 and slide 450 proximally relative to suction arm 23. Movement of cable 430 and slide 450 in a proximal direction relative to suction arm 23 moves suction paddles 22 into a non-spread position as shown in FIGS. 37 and 45. The pin and slot configuration of spreader members 460, 470, slide 450 and anchor 440 cause spreader members 460, 470 to move suction paddles 22 parallel to one another as shown in FIGS. 34 and 38. Lever 420 includes a spring (not shown) to provide a biasing force to keep lever 420 in a non-actuated position and suction paddles 22 in a spread position as shown in FIG. 34.

Although, in this embodiment both suction paddles 22 are seen movable between the non-spread position of FIG. 37 and the spread position of FIG. 38, spreader 180 may also be configured with only one suction paddle 22 being movable.

In addition, handle 310 may alternatively include another type of actuator mechanism to remotely control spreader 180, for example, a knob, a plunger mechanism, a pair of scissor-type handles, or a slidable button within a longitudinal slot. The actuator mechanism may be, for example, voice-activated comprising voice-recognition technologies. A visual and/or audible signal, such as a flashing light and/or beeping tone, may be incorporated to alert a surgeon to the completion or resumption of the actuator. Spreader 180 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor. As previously discussed, spreader 180 may be coupled to gearing, which in turn, is coupled to a motor. The motor is further coupled to a power source. The motor and power source which may be used together are coupled to a controller which detects and controls the amount of spread or area between the suction paddles. Of course, further designs to control the spreading of suction paddles may also be used, such as other mechanical or hydraulic activated or controlled systems.

In FIG. 46, an alternate embodiment of suction device 12 is shown. In this embodiment, the distal end of suction arm 23 comprises two remotely actuated variable linkages or joints, as seen linkage 350 and joint 800. Suction arm 23 may include, for example, a plurality of remotely actuable variable joints such as elbows, wrists, hinges, linkages and/or ball and sockets, as is well known in the art. See for example, U.S. Pat. No. 5,374,277 of Hassler, again incorporated herein by reference. FIG. 47 is a side view of joint 800. As seen in FIGS. 46 and 47, joint 800 pivots at pivot point 810 which may comprise a pin. Joint 800 may be remotely actuable via cables (not shown) extending between joint 800 and handle 310 (not shown) through suction arm 23. The distal end of the cables would be connected to joint 800. The proximal end of the cables would be connected to an actuator mechanism (not shown) on arm or handle. The actuator mechanism used to remotely control joint 800 may be, for example, a knob, a lever mechanism, a plunger mechanism, a pair of scissor-type handles, or a slidable button within a longitudinal slot. The actuator mechanism may be, for example, voice-activated comprising voice-recognition technologies. A visual and/or audible signal, such as a flashing light and/or beeping tone, may be incorporated to alert a surgeon to the completion or resumption of the actuator. Joint 800 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

As described earlier, suction device 12 may include additional features, for example, an irrigation means for providing a distribution of irrigation fluid onto the area of the heart where the surgical procedure will be performed. Suction device 12 may feature a light means to provide light to where the surgical procedure will be performed, for example, via an optical fiber coupled to a remote light source. Suction device 12 may feature a suture securing or retaining means, such as a suture coil or a plurality of slots formed in the upper surfaces of suction paddles 22. Suction device 12 may feature one or more electrodes, a cutting means or a visual means.

Figure 48:
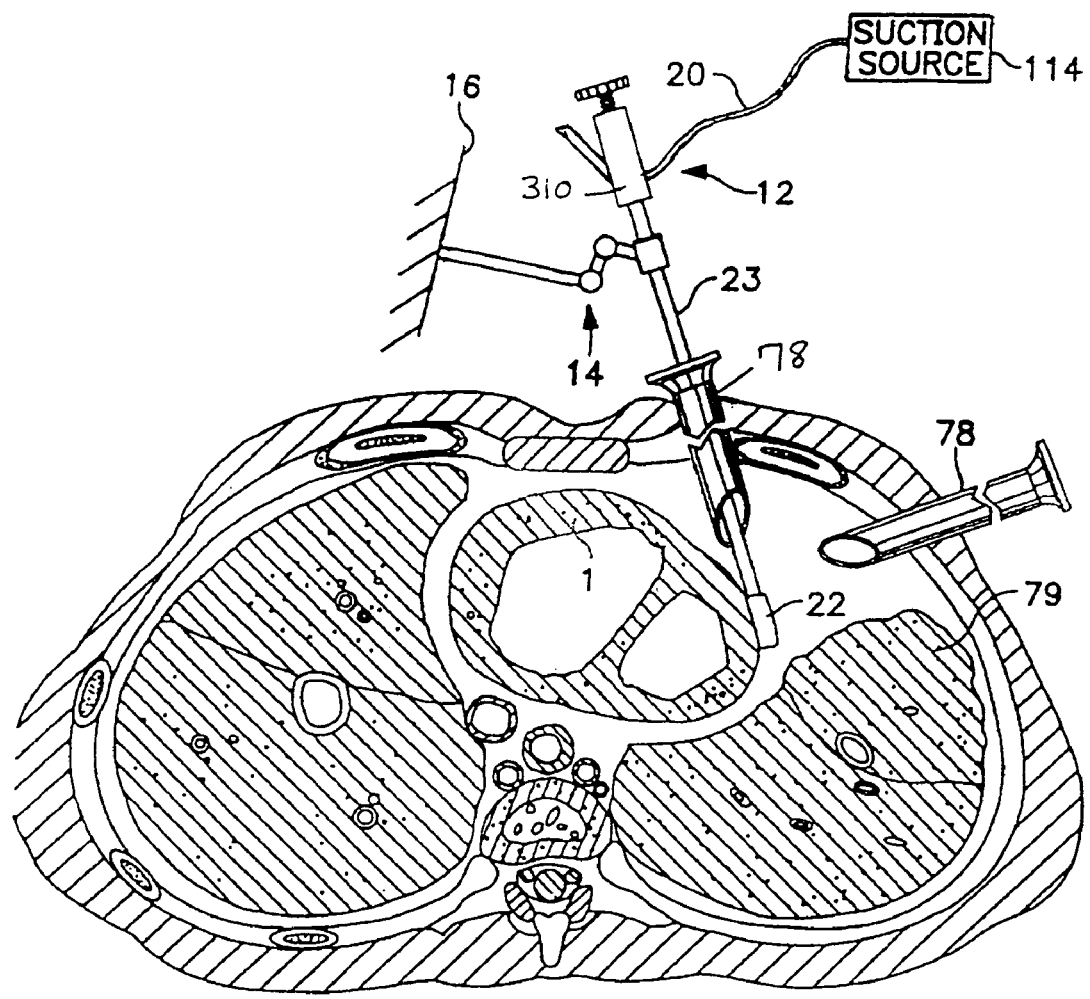
FIG. 48 is a cross-sectional view of a body showing one method of achieving access to a surface of the heart and using the present invention to immobilize an area of tissue.

FIG. 48 is a cross-sectional view of a body showing one method of achieving access to a surface of the heart and using the present invention to immobilize an area of tissue. As seen suction device 12 is sized to fit appropriately within a trocar sleeve. Preferably the trocar sleeve has an internal diameter of about 15 mm or less. In addition, suction device 12 has a length selected to reach a target site, such as a heart or other organ, in a body cavity, such as the thoracic cavity or abdomen, and to extend sufficiently out of the body cavity to facilitate easy manipulation and securing of the device. A trocar sleeve, port or cannula may be positioned in a percutaneous intercostal penetration. Suction device 12 may be sized appropriately to be introduced through a small cut, incision, stab wound, hole, port, cannula, trocar sleeve or the like, for example, through the chest wall between two adjacent ribs which does not require cutting, removing, or significantly, displacing or retracting the ribs or sternum. Usually, a percutaneous intercostal penetration will require a puncture or incision of less than about 5 cm in length. Additional ports, cannulae or surgical trocars may be introduced to permit additional suction devices to be introduced or to permit endoscopy and surgical access to heart 1. Usually, trocar sleeves will be positioned within intercostal spaces in the left lateral chest of the patient, generally within the second, third, fourth, fifth, sixth or seventh intercostal spaces. In addition the left lung 79 may be partially collapsed so as to provide an unencumbered area in which to manipulate surgical instruments.

To introduce this embodiment of suction device 12 through a small cut, incision, stab wound, hole, port, cannula or trocar sleeve or the like, a surgeon would first use actuator knob 360 on handle 310 to pivot suction paddles 22 about a transverse axis so that the paddles are oriented generally parallel to suction arm 23. Next, the surgeon would fully actuate lever 420 on handle 310, as shown in FIG. 45, thereby causing spreader 180 to move suction paddles 22 together into a fully non-spread position. The distal-end of suction device 12, including suction paddles 22 and spreader 180, may then be introduced into the body cavity such as the chest through, for example a trocar sleeve as shown in FIG. 48. After suction paddles 22 and spreader 180 have passed through a trocar sleeve 78 and into the body cavity, spreader 180 may be actuated to allow suction paddles 22 to partially or fully spread apart in a parallel orientation to each other, thereby creating a gap between suction paddles 22. If additional spreading of suction paddles 22 is desired following their engagement to heart tissue then spreader 180 may be partially actuated at this time. If no additional spreading of suction paddles 22 is desired following their engagement to heart tissue then spreader 180 may be allowed to fully spread suction paddles 22, as shown in FIG. 34, at this time.

After suction paddles 22 and spreader 180 have passed into the body cavity and suction paddles 22 have been partially or fully spread apart, a surgeon may use actuator knob 360 on handle 310 to pivot suction paddles 22 about a transverse axis (see FIGS. 35 and 36) so that their contact surfaces are oriented generally parallel to the area in which temporary immobilization of the heart tissue is desired. For example, the surgeon may pivot the paddles upwards with respect to suction arm (see FIG. 35) and push suction device in the distal direction to place at least portions of paddles against the heart surface. If the tissue surface has a different orientation, e.g., facing away from the surgeon, the surgeon may pivot the paddles downwards (see FIG. 36) with respect to suction arm and pull suction device in the proximal direction to place at least portions of paddles against the heart surface. Alternatively a surgeon may change the orientation of the paddles prior to spreading of the paddles.

Suction paddles generally are placed in the area in which temporary immobilization of the heart tissue is desired. When used for a coronary artery bypass graft procedure, suction paddles are generally placed such that the target coronary artery is positioned between the paddles, i.e., one paddle is placed on each side of the artery. Once suction paddles are placed, suction is then created in suction ports. Through the suction, the device then is fixed to or grabs hold of the heart tissue. Once the suction is created and the paddles are secured to the heart tissue, the paddles may again be spread slightly further apart if they had been only partially spread prior to placement. The effect of this further spreading in a parallel orientation after the paddles have been secured or engaged to the heart tissue is to cause an even tension to be created in the area of the heart tissue between the paddles. This increase in epicardial tension further immobilizes the area by dampening or decreasing the motion due to the intrinsic beating of the heart in the area of the heart tissue between the paddles. In addition, the spreading apart of paddles after they have been secured or engaged to the heart tissue helps to increase exposure of the target coronary artery.

If friction paddles are used instead of suction paddles, once paddles have been placed, for example, on each side of the target coronary artery, a force may be used to engage friction paddles to the heart tissue as opposed to using suction to engage suction paddles to the heart tissue. Once friction paddles have been secured or engaged to the heart tissue they may be further spread as discussed above.

Referring again to FIG. 48, once paddles 22 are suitably positioned and engaged to the heart tissue, suction device 12 may be clamped or secured by a securing device 14 to a stationary object or stable support, such as operating table 16 to fix the position of suction arm 23 relative to the beating heart. Alternatively, suction device 12 may be secured to a mounting rail 999 or a mounting 224 as discussed previously or to a stationary rib retractor, trocar sleeve, cannula or port that is fixed to the patient's chest and does not move relative to the beating heart. For example, suction device 12 may be introduced through a locking cannula or trocar sleeve that is fixed to a patient's chest and that will clamp onto suction device 12, thereby securing its position with respect to the beating heart. Suction device 12 may be secured to a stable object using a variety of methods, for example, a clamp, a screw, a wing nut, a slip and grip-type holder or a lockable footing which in turn locks onto a rail. Slip and grip-type holders and lockable footings are previously discussed.

Once the paddles are suitably secured, positioned and engaged to the heart tissue thereby temporarily immobilizing the area of tissue, the coronary artery in that area, for example, may be operated upon. The anastomosis of the coronary artery may be accomplished through any acceptable end-to-end, end-to-side or side-to-side technique, for example manual suturing. In addition, other methods of performing the anastomosis may be used, for example, tissue-bonding techniques such as tissue adhesives and laser welding of tissue may be used. Mechanical anastomotic devices including stapling devices, clipping devices, ring and pin coupling devices and suturing devices may also be used. These anastomotic devices may be automated or semi-automated Mechanical couplers including stents, ferrules, and/or rings may also be used to form an anastomosis. Materials used to form an anastomosis via a mechanical device and/or coupler may be biocompatible, bioabsorbable, bioactive and/or bioinert. Following completion of the surgical procedure, e.g., the anastomosis, the paddles are disengaged from the heart surface, positioned in a non-spread configuration and aligned with arm, see FIG. 45 The suction device is unsecured from the stationary object and removed from the patient's body It should be understood that the present invention may be used in conjunction with a conventional thoracotomy and in various surgical procedures including throascopic, laparoscopic, and arthroscopic procedures as well as in conventional open heart surgical procedures. The invention is also useful for repositioning an organ in a body cavity to facilitate a surgical procedure. As discussed earlier, a suction device comprising a remotely controllable spreader means is particularly useful in minimally-invasive and endoscopic procedures.

FIG. 49 depicts a further alternate embodiment of the present invention, and in particular of a suction device that may be used in an endoscopic procedure, as described earlier, featuring at its distal end a suction arm 23 and a pair of suction paddles 22, each of which is coupled to a spreader 180. The distal end of the suction device is suitably configured for delivery through a small, percutaneous penetration, for example a small cut, incision, stab wound, hole, port, cannula, trocar sleeve or the like. Suction arm 23 of the suction device has a proximal end (not shown) and a distal end (as shown in FIGS. 49, 50 and 51). In this embodiment suction arm 23 has a circular cross-sectional shape, however suction arm 23 may alternatively have a rectangular, triangular, oval or channel cross-sectional shape. The suction device may feature a handle (not shown) located at the proximal end of suction arm 23. As previously discussed, the suction device may be coupled to a suction source through a suction line to a suction fitting located on the arm or handle. For an example of a suitable suction device handle, see FIG. 34 Referring again to FIGS. 49, 50 and 51, suction paddles 22 are shown pivotably coupled to spreader 180 at pivot points 901, 902, 903 and 904, each comprising pins.

Spreader 180 may be rigidly coupled to suction arm 23 at 340. Alternatively, spreader may be rotatably or pivotably coupled to suction arm 23 at 340, thereby permitting spreader 180 to freely or controllably move or rotate relative to suction arm 23. As seen in FIG. 49, in this embodiment of the invention, spreader 180 may be controllably moved relative to suction arm 23 since spreader 180 is coupled to suction arm 23 via remotely actuable joint 800. In this embodiment, the distal end of suction arm 23 is shown to comprise one remotely actuated linkage or joint 800. However, suction arm 23 may include, for example, a plurality of remotely actuable variable joints, elbows, wrists, hinges, linkages and/or ball and sockets, as is well known in the art. See for example, U.S. Pat. No. 5,374,277 of Hassler, again incorporated herein by reference. FIG. 47 is a side view of joint 800. As seen in FIG. 47, 49, 50 and 51, joint 800 pivots at pivot point 810 which may comprise a pin. Joint 800 may be remotely actuable via cables (not shown) extending between joint 800 and a handle (not shown) through suction arm 23. The distal end of the cables would be connected to joint 800. The proximal end of the cables would be connected to an actuator mechanism (not shown) on the arm or handle. The actuator mechanism used to remotely control joint 800 may be, for example, a knob, a lever mechanism, a plunger mechanism, a pair of scissor-type handles, or a slidable button within a longitudinal slot in handle. The actuator mechanism may be, for example, voice-activated comprising voice-recognition technologies. A visual and/or audible signal, such as a flashing light and/or beeping tone, may be incorporated to alert a surgeon to the completion or resumption of the actuator. Joint 800 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

Suction paddles 22 in this embodiment comprise a series of two suction ports each of which is connected in fluid communication to a suction conduit through suction aperture (not shown). Note that the exact number, position and/or size of suction ports may vary. Each suction conduit is connected in fluid communication to a suction lumen (not shown) located within suction arm 23 through a separate suction line (not shown). The suction lumen within arm 23 would be connected in fluid communication to a suction fitting located on the arm or handle (both not shown). Therefore, when the suction fitting is connected to a suction source through a suction line (both not shown), suction would be created in the suction ports. Note that the suction device may include a suction controller to control the amount of suction at the suction ports. Suction controller may be, for example, a valve. Suction controller may also be, for example, voice-activated comprising voice-recognition technologies. A visual and/or audible signal, such as a flashing light and/or beeping tone, may be incorporated to alert a surgeon to the completion or resumption of suction. Suction controller may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

In this embodiment, suction paddles, suction ports, suction apertures and suction conduits are all generally similar to those previously described. In addition, the suction device may be constructed such that each suction paddle and/or each suction port is coupled to a separate suction source allowing them to be independently disconnected from their respective suction source or the suction device may be constructed such that each suction paddle and/or each suction port is coupled to the same suction source, as described in this embodiment.

FIG. 49 is a top view of spreader 180 with coupled suction paddles 22 in a non-spread position, whereas FIG. 50 and 51 are top views of spreader 180 with coupled suction paddles 22 in a partially spread position and a fully spread position, respectively. As seen in FIGS. 49, 50 and 51, in this embodiment of the invention, suction paddles 22 are attached to spreader 180 such that suction paddles 22 are oriented generally parallel to each other. A cable (not shown) would extend between spreader 180 and an actuator mechanism located at the proximal end of suction arm 23. The proximal end of the cable would be connected to an actuator mechanism located on the arm or handle. The distal end of cable would be connected to spreader 180. An actuator mechanism may be used to remotely and controllably actuate spreader 180.

The actuator mechanism may be, for example, a knob, a lever mechanism, a plunger mechanism, a pair of scissor-type handles, or a slidable button within a longitudinal slot in handle. The actuator mechanism may be, for example, voice-activated comprising voice-recognition technologies. A visual and/or audible signal, such as a flashing light and/or beeping tone, may be incorporated to alert a surgeon to the completion or resumption of the actuator. Spreader 180 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

The cable (not shown) may be made of stainless steel. The distal end of the cable would be attached to spreader member 915 of spreader 180. Spreader member 915 is pivotably coupled to suction paddles 22 at pivot points 901, 904. Spreader member 915 also comprises a pin at 910 that fits slidably into longitudinal slot 921 of anchor member 920. Anchor member 920 of spreader 180 is pivotably coupled to suction paddles 22 at pivot points 902, 903. Anchor member 920 is also coupled to joint 800 at 340.

As shown in FIGS. 49, 50 and 51, spreader 180 maintains suction paddles 22 parallel to one another throughout movement between a non-spread and a spread position. Controllably moving spreader member 915 distally relative to anchor member 920, for example via a cable, will move suction paddles into a non-spread position as shown in FIG. 49. Controllably moving spreader member 915 proximally relative to anchor member 920 will move suction paddles into a fully spread position as shown in FIG. 51. The pin and slot configuration of spreader member 915 and anchor member 920 allows spreader 180 to controllably move suction paddles 22 parallel to one another as shown in FIGS. 49, 50 and 51. In addition, handle 310 may alternatively include another type of actuator mechanism to remotely control spreader 180, for example, a knob or a plunger. Although, in this embodiment both suction paddles 22 are seen movable between the non-spread position of FIG. 49 and the spread position of FIG. 51, spreader 180 may also be configured with only one suction paddle 22 being movable. A spreader 180 wherein only one suction paddle moves relative to the other is shown in FIGS. 52 and 53.

Another embodiment of the distal end of suction arm 23, is shown in FIGS. 52 and 53. The distal end of suction arm 23 comprises two remotely actuated variable joints 800 which pivot about pins at pivot points 810. Joints 800 may be remotely actuable via cables (not shown) extending between joints 800 and a handle (not shown) through suction arm 23. The distal end of the cables would be connected to joints 800. The proximal end of the cables would be connected to one or more actuator mechanisms (not shown) on the arm or handle. The actuator mechanism used to remotely control a joint 800 may be, for example, a knob, a lever mechanism, a plunger mechanism, a pair of scissor-type handles, or a slidable button within a longitudinal slot in handle. The actuator mechanism may be, for example, voice-activated comprising voice-recognition technologies. A visual and/or audible signal, such as a flashing light and/or beeping tone, may be incorporated to alert a surgeon to the completion or resumption of the actuator. Joint 800 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor. Joint 800 may be locked into position, for example, via tube 802 located within arm 23. Pushing tube 802 distally against joint 800, thereby applying pressure to joint 800, locks joint 800 into position. The actuator mechanism used to remotely control the movement of tube 802 may be, for example, a knob, a lever mechanism, a plunger mechanism, a pair of scissor-type handles, or a slidable button within a longitudinal slot in handle. In addition, tube 802 may be used as a suction lumen located within suction arm 23 for providing suction to suction ports 33.

As shown in FIGS. 52 and 53, suction paddles 22 are shown rigidly coupled to spreader 180 at 330. Spreader 180 may be controllably moved relative to suction arm 23 since spreader 180 is coupled to suction arm 23 via the two remotely actuable joints 800. FIG. 52 is a top view of spreader 180 with coupled suction paddles 22 in a non-spread position, whereas FIG. 53 is a top view of spreader 180 with coupled suction paddles in a fully spread position In this embodiment of the invention, suction paddles 22 are attached to spreader 180 such that suction paddles 22 are oriented generally parallel to each other. Cable 931 extends between spreader 180 and an actuator mechanism (not shown) that would be located at the proximal end of suction arm 23. The proximal end of the cable would be connected to an actuator mechanism located on the arm or handle. The distal end of cable is connected to spreader 180. An actuator mechanism may be used to remotely and controllably actuate spreader 180.

Cable 931 may be made of stainless steel. The distal end of the cable would be attached to spreader member 950 of spreader 180. Spreader member 950 is pivotably coupled to the distal end of spreader member 932 at pivot point 936 and to the distal end of spreader member 933 at pivot point 937. The proximal end of spreader member 932 is pivotably coupled to spreader member 951 at pivot point 934. The adjacent sides of spreader members 932 and 933 may be designed to engage or interlock with one another when they are in direct contact, for example when spreader is in a spread position. Spreader member 932, for example, may include a groove or slot that spreader member 933 will fit or slide into. The interlocking of spreader members 932 and 933 provides increased strength. The proximal end of spreader member 933 is pivotably coupled to spreader member 951 at pivot point 935. Spreader member 951 is coupled to the most distal joint 800 of suction arm 23. Spreader 180 may include a spring to provide a biasing force to position suction paddles in a non-spread overlapping position as shown in FIG. 52 when spreader 180 is not actuated. Moving cable 931 in a proximal position relative to suction arm 23 will force suction paddles into a parallel spread position as shown in FIG. 53.

The actuator mechanism for remotely controlling spreader 180 may be, for example, a knob, a lever mechanism, a plunger mechanism, a pair of scissor-type handles, or a slidable button within a longitudinal slot. The actuator mechanism may be, for example, voice-activated comprising voice-recognition technologies. A visual and/or audible signal, such as a flashing light and/or beeping tone, may be incorporated to alert a surgeon to the completion or resumption of the actuator. Spreader 180 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor. As previously discussed, spreader 180 may be coupled to gearing, which in turn, is coupled to a motor. The motor is further coupled to a power source. The motor and power source which may be used together are coupled to a controller which detects and controls the amount of spread or area between the suction paddles. Of course, further designs to control the spreading of suction paddles may also be used, such as other mechanical or hydraulic activated or controlled systems.

Another embodiment of suction arm 23, is shown in FIGS. 54 and 55. At least a portion of suction arm 23 comprises a plurality of flexible, lockable interconnecting links thereby allowing it to be positioned in every direction until the desired configuration is achieved at which point the flexible arm may be locked into a fixed configuration by an actuator mechanism attached to the proximal end of cable 965. Cable 965 runs axially through the interconnecting links of suction arm 23 and is coupled to spreader 180. FIG. 54 is a bottom view of spreader 180 with coupled suction paddles 22 in a non-spread position, whereas FIG. 55 is a bottom view of spreader 180 with coupled suction paddles in a fully spread position. In this embodiment of the invention, suction paddles 22 are attached to spreader 180 such that suction paddles 22 are oriented generally parallel to each other. Cable 936 extends between spreader 180 and an actuator mechanism (not shown) that would be located at the proximal end of suction arm 23 The proximal end of the cable would be connected to an actuator mechanism located on the arm or handle. An actuator mechanism is used to remotely and controllably actuate spreader 180. The actuator mechanism may be, for example, a knob, a lever mechanism, a plunger mechanism, a pair of scissor-type handles, or a slidable button within a longitudinal slot in handle. The actuator mechanism may be, for example voice-activated comprising voice-recognition technologies. A visual and/or audible signal, such as a flashing light and/or beeping tone, may be incorporated to alert a surgeon to the completion or resumption of the actuator. Spreader 180 may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

The distal end of cable 965 is connected to spreader 180. The cable may be made of stainless steel. The distal end of cable 965 is anchored to slide 960 of spreader 180 using cable anchor 966. The distal end of slide 960 is pivotably coupled to the proximal ends of spreader members 963, 964, 965, 966 at pivot points 967, 968 both comprising pins. The distal ends of spreader members 963, 964, 965, 966 are, in turn, pivotably coupled to suction paddles 22 at pivot points 969, 970, 971, 972 which all comprise pins. The adjacent sides of spreader members 963 and 964 may be designed to engage or interlock with one another when they are in direct contact, for example when spreader is in a spread position. Spreader member 963, for example, may include a groove or slot that spreader member 964 will fit or slide into. The interlocking of spreader members 963 and 964 provides increased strength. The adjacent sides of spreader members 965 and 966 may also be designed to engage or interlock with one another when they are in direct contact again, for example when spreader is in a spread position. Spreader member 965, for example, may include a groove or slot that spreader member 966 will fit or slide into. The interlocking of spreader members 965 and 966 provides increased strength. Slide 960 is slidably coupled to anchor 961. Slide 960 is also slidably coupled to wedge 973 Wedge 973 is rigidly coupled to anchor 961 via spreader member 962.

When no tension is placed on cable 965 attached to spreader 180 and running through the length of suction arm 23, the paddles are in a non-spread, overlapping position, as shown in FIG. 54, and the arm is relatively flexible within the region of the interconnecting links. It is in this configuration that the suction device is suitable for endoscopic delivery as discussed previously, for example through a trocar access. The arm may comprise cables for remotely controlling its orientation. Following endoscopic delivery, tension is applied to cable 965, i.e., the cable moves proximally relative to suction arm 23, causing the paddles to spread apart in a parallel orientation as shown in FIG. 55. The distance between suction paddles 22 is controllable by the movement of cable 965. Once the paddles have been generally placed in the area in which temporary immobilization of the heart tissue is desired, suction is applied to secure the paddles to the heart tissue. Once suction is created and the paddles are secured to the heart tissue, the paddles are again spread slightly further apart in a parallel orientation by moving or pulling the cable further in the proximal direction which also locks the arm in place. The further spreading of the paddles after the paddles have been secured or engaged to the heart tissue is to cause an even tension to be created in the area of the heart tissue between the paddles. This increase in epicardial tension further immobilizes the area by dampening or decreasing the motion due to the intrinsic beating of the heart in the area of the heart tissue between the paddles. In addition, the spreading apart of paddles after they have been secured or engaged to the heart tissue helps to increase exposure of the target coronary artery.

Referring again to FIGS. 54 and 55, suction paddles 22 are shown in this embodiment to comprise a two suction ports 33 each of which is connected in fluid communication to a suction conduit through a suction aperture (both not shown). Note that the exact number, position and/or size of suction ports 33 may vary. Each suction conduit is connected in fluid communication to a suction line 72 which, in this embodiment, is shown to run along the outer surface of suction arm 23. Therefore, when suction lines 72 are connected to a suction source (not shown), suction is created in suction ports 33. Note that the suction device may include a suction controller, for example, a valve. Suction controller may also be, for example, voice-activated comprising voice-recognition technologies. A visual and/or audible signal, such as a flashing light and/or beeping tone, may be incorporated to alert a surgeon to the completion or resumption of suction. Suction controller may be slaved to a robotic system which may include, for example, head-mounted displays which integrate 3-D visualization of surgical anatomy and related diagnostic and monitoring data, miniature high resolution 2-D and 3-D digital cameras, a computer, a high power light source and a standard video monitor.

In this embodiment, suction paddles 22, suction ports 33, suction apertures and suction conduits are all generally similar to those previously described. As shown in this embodiment, the suction device is constructed such that each suction paddle 22 is coupled to a separate suction line allowing them to be independently disconnected from their respective suction source.

Figure 56:
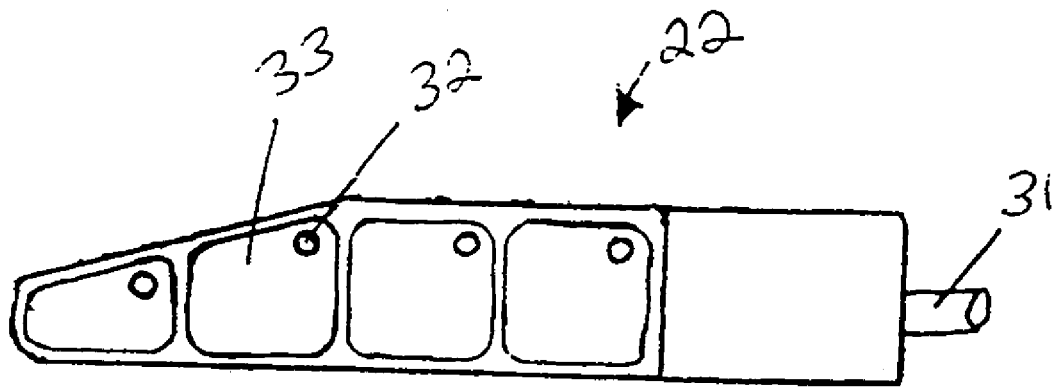
FIG. 56 is a bottom view of an alternate embodiment of suction paddle of the present invention.
Figure 57:
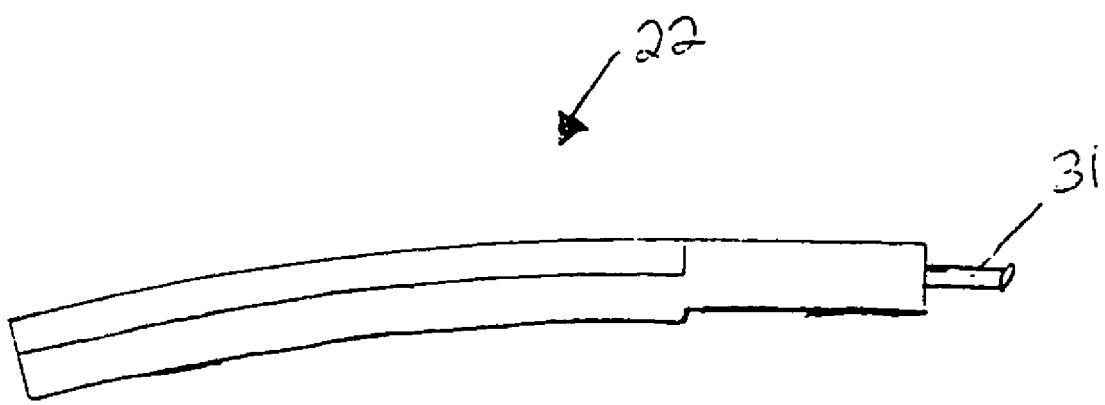
FIG. 57 is a side view of an alternate embodiment of suction paddle of the present invention.

Another embodiment of suction paddles 22, is shown in FIG. 56. Suction paddle 22 is shown in this embodiment to comprise a series of four suction ports 33 each of which is connected in fluid communication to suction conduit 31 through suction aperture 32. In this embodiment, suction paddle 22, suction ports 33, suction apertures 32 and suction conduits 31 are all generally similar to those previously described. FIG. 57 is a side view of suction paddle 22 showing the low profile design of suction paddle 22 in this embodiment. A low profile suction paddle helps provide more room for performing a surgical procedure, such as sewing an anastomosis in the area of the suction paddles.

The term "tissue engager array" used herein comprises a first tissue engaging member, a second tissue engaging member and a spreader. A tissue engager array may be used with other components to form a tissue immobilizing device. As discussed earlier, the tissue immobilizing devices described herein may include additional features, for example, the ability to provide for the distribution of irrigation fluid onto the area of the heart where the surgical procedure will be performed. The suction device may feature the ability to provide light to where the surgical procedure will be performed, for example, via an optical fiber coupled to a remote light source. The suction device may feature a suture securing or retaining means, such as a suture coil or a plurality of slots formed in the upper surfaces of suction paddles. The suction device may feature one or more electrodes, a cutting apparatus or a visual means.

As disclosed, the present invention relates to a method and apparatus for immobilizing tissue. In the preferred embodiment, the invention is used to immobilize heart tissue for a coronary artery bypass graft procedure using either an open or closed chest approach, without the need for a cardiopulmonary bypass. Other surgical techniques, however, which require immobilizing body tissue may also be performed using the present invention, such as surgery on other organs such as the stomach, gall bladder, etc., as well as on other body tissues, such as the eye or the skin, for example. In addition, while the present invention has been described in detail with particular reference to a preferred embodiment and alternate embodiments, it should be understood variations and modifications can be effected within the scope of the following claims. Such modifications may include substituting elements or components which perform substantially the same function in substantially the same way to achieve substantially the same result for those described herein.

What is claimed is:

1. A device for temporarily grasping an area of tissue of a beating heart within a closed chest of a patient, the device comprising:
    a suction member having a contact surface adapted to be positioned on a surface of the beating heart within the closed chest, the suction member having a suction lumen open to the atmosphere through the contact surface, the suction member comprising one or more electrodes;
    a securing member to secure the suction member to an operating table, the securing member coupled to the suction member; and,
    a remote actuator for moving the suction member relative to the securing member within the chest of the patient, the remote actuator adapted for positioning outside the chest of the patient.

2. The device of claim 1 wherein access to the beating heart is achieved through a small incision, stab wound, trocar or mini-thoracotomy.

3. The device of claim 1 wherein the suction member is sized to be introduced into the chest of the patient through a small incision, stab wound or mini-thoracotomy.

4. The device of claim 1 further comprising an endoscope.

5. The device of claim 1 wherein the securing device comprises at least one joint or hinge.

6. The device of claim 5 wherein the remote actuator is adapted to actuate the at least one joint or hinge from a position outside the chest of the patient.

7. The device of claim 1 wherein the remote actuator is capable of locking the position of the suction member relative to the securing member.

8. The device of claim 1 wherein the device further comprises a means for dispensing or removing a fluid in the chest of the patient.

9. The device of claim 1 wherein the device further comprises a means for delivering light in the chest of the patient.

10. The device of claim 1 further comprising a suture fixation member.

11. The device of claim 1 wherein a pulse generator is electronically coupled to the electrodes.

12. The device of claim 1 wherein the securing member comprises an arm.

13. The device of claim 12 wherein the arm is bendable.

14. The device of claim 12 wherein the arm is a variable friction arm.

15. The device of claim 1 wherein the securing member comprises at least one ball and socket joint.

16. The device of claim 1 wherein the securing member comprises a clamp.

17. The device of claim 1 wherein the securing member comprises a slip-grip type holder.

18. The device of claim 1 wherein the suction member comprises at least one paddle.

19. The device of claim 1 wherein the contact surface of the suction member conforms generally to the curvature of a patient's heart.

20. The device of claim 1 further comprising a suction line for communicating a suction from a source of negative pressure to the suction lumen.

21. The device of claim 20 wherein the suction is provided at a negative pressure between about 200 and about 600 mm Hg.

22. The device of claim 1 wherein the contact surface of the suction member comprises at least one suction port in communication with the suction lumen.

23. The device of claim 22 wherein the at least one suction port is cylindrical-shaped.

24. The device of claim 22 wherein the at least one suction port is cone-shaped.

25. The device of claim 22 wherein the at least one suction port is dome-shaped.

26. The device of claim 1 wherein the securing member includes a clamp for clamping to the operating table.

27. The device of claim 1 wherein the operating table includes a mounting rail.

28. The device of claim 27 wherein the securing member includes a clamp for clamping to the mounting rail.

29. The device of claim 27 wherein the mounting rail includes a clamp for clamping the mounting rail to the operating table.

30. A device for temporarily grasping an area of tissue of a beating heart within a closed chest of a patient, the device comprising:
a suction member having a contact surface adapted to be positioned on a surface of the beating heart within the closed chest, the suction member having a suction lumen open to the atmosphere through the contact surface;
a suture fixation member, wherein the suture fixation member comprises a coil;
a securing member to secure the suction member to an operating table, the securing member coupled to the suction member; and,
a remote actuator for moving the suction member relative to the securing member within the chest of the patient, the remote actuator adapted for positioning outside the chest of the patient.

31. A device for temporarily grasping an area of tissue of a beating heart within a closed chest of a patient, the device comprising:
a suction member having a contact surface adapted to be positioned on a surface of the beating heart within the closed chest, the suction member having a suction lumen open to the atmosphere through the contact surface;
a securing member to secure the suction member to an operating table, the securing member coupled to the suction member, the securing member comprising an arm, the arm having a proximal end and a distal end, the arm comprising:
a plurality of links, the links being free to move relative to one another so that the arm articulates;
a cable extending through the links, the cable having a distal end and a proximal end; and,
a locking actuator coupled to the proximal end of the cable and the proximal end of the arm to tension the cable thereby locking the links relative to one another so that the arm changes from an articulating condition to a locked rigid condition; and,
a remote actuator for moving the suction member relative to the securing member within the chest of the patient, the remote actuator adapted for positioning outside the chest of the patient.

32. A device for temporarily grasping an area of tissue of a beating heart within a closed chest of a patient, the device comprising:
a suction member having a contact surface adapted to be positioned on a surface of the beating heart within the closed chest, the suction member having a suction lumen open to the atmosphere through the contact surface;
a securing member to secure the suction member to an operating table, the securing member coupled to the suction member, the securing member comprising at least one ball and socket joint, wherein the ball and socket securing member comprises a plurality of tube elements jointed together by a plurality of ball elements, the tube elements having socket ends shaped to mate with the ball elements, a cable disposed throughout the series of ball elements and tube elements and a locking actuator coupled to the cable, the locking actuator being capable of tightening the cable to lock the securing member into position; and,
a remote actuator for moving the suction member relative to the securing member within the chest of the patient, the remote actuator adapted for positioning outside the chest of the patient.

33. The device of claim 32 further comprising a means for maintaining the same length of the cable within the securing device regardless of the orientation of any tube element to an adjacent ball element.

34. The device of claim 33 wherein the means for maintaining the same length of the cable within the securing device comprises tapered bushings positioned within the lumen of the ball elements, the tapered bushings having a passage way thereout which has a first diameter at a first end, a second diameter in the middle and a first diameter at an end opposite the first end, the first diameter being larger than the second diameter.

35. The device of claim 32 wherein the locking actuator is actuated remotely from a position outside a patient's chest.

36. A minimally invasive surgical method of grasping tissue of a beating heart without creating an incision through the sternum of a patient and spreading apart the chest of the patient, the method comprising the following steps:

providing a medical device having a suction member, a securing member and a remote actuator, the suction member having a contact surface adapted to grasp tissue of the beating heart, the suction member having a suction lumen open to the atmosphere through the contact surface, the suction lumen adapted to be coupled to a suction source, wherein suction is communicated to the tissue of the beating heart to grasp it, the suction member comprising one or more electrodes, the securing member coupled to the suction member, the securing member adapted to secure the suction member to an operating table, the remote actuator coupled to the suction member, the remote actuator adapted to move the suction member relative to the securing member within the chest of the patient, the remote actuator adapted for positioning the suction member from outside the chest of the patient;

creating a small incision or stab wound between the ribs of the patient to access the beating heart;

introducing the suction member into the chest of the patient through the small incision or stab wound;

moving the suction member within the chest of the patient so as to contact tissue of the beating heart;

creating suction in the suction lumen to grasp tissue of the beating heart; and, securing the suction member to an operating table.

37. The method of claim 36 further comprising the step of performing a surgical procedure on the beating heart.

38. The method of claim 37 wherein the surgical procedure is performing a coronary artery bypass graft.

39. The method of claim 38 wherein the coronary artery bypass graft procedure comprises grafting a mammary artery to a coronary artery.

40. The method of claim 36 further comprising the step of mobilizing an artery or vein.

41. The method of claim 40 wherein the step of mobilizing an artery or vein comprises mobilizing a mammary artery or saphenous vein.

42. The method of claim 36 further comprising the step of moving or repositioning the beating heart to achieve better access to an area of the beating heart which would otherwise be difficult to access.

43. The method of claim 42 wherein the step of moving or repositioning the beating heart to achieve better access to an area of the beating heart which would otherwise be difficult to access comprises moving or repositioning the beating heart to access the posterior or backside of the heart.

44. The method of claim 42 wherein the step of moving or repositioning the beating heart to achieve better access to an area of the beating heart which would otherwise be difficult to access comprises moving or repositioning the beating heart without significant deterioration of the pumping function of the beating heart.

45. The method of claim 36 further comprising the step of immobilizing an area of tissue on a beating heart.

46. The method of claim 36 further comprising the step of dispensing or removing a fluid in the chest of the patient, wherein the medical device comprises a means for dispensing or removing the fluid.

47. The method of claim 36 further comprising the step of delivering light in the chest of the patient, wherein the medical device comprises a means for delivering the light.

48. The method of claim 36 further comprising the step of injecting a medicinal substance into the heart.

49. The method of claim 36 further comprising the step of at least partially collapsing at least one lung so as to provide an unencumbered area in which to manipulate at least one surgical instrument.

50. The method of claim 36 further comprising the step of using an endoscope.

51. The method of claim 36 wherein the securing member comprises at least one joint or hinge.

52. The method of claim 51 wherein the remote actuator actuates the at least one joint or hinge.

53. The method of claim 36 wherein the remote actuator is capable of locking the position of the suction member relative to the securing member.

54. The method of claim 36 wherein the securing member comprises an arm, the arm having a proximal end and a distal end, the arm comprising:
a plurality of links, the links being free to move relative to one another so that the arm articulates; and,
a cable extending through the links.

55. The method of claim 54 wherein the securing member further comprises a locking actuator coupled to one end of the cable and one end of the arm to tension the cable thereby locking the links relative to one another so that the arm changes from an articulating condition to a locked rigid condition.

56. The method of claim 36 wherein the securing member comprises an arm.

57. The method of claim 56 wherein the arm is bendable.

58. The method of claim 56 wherein the arm is a variable friction arm.

59. The method of claim 36 wherein the securing member comprises at least one ball and socket joint.

60. The method of claim 36 wherein the securing member comprises a clamp.

61. The method of claim 36 wherein the securing member comprises a slip-grip type holder.

62. The method of claim 36 wherein the suction member comprises at least one paddle.

63. The method of claim 36 wherein the contact surface of the suction member conforms generally to the curvature of the beating heart.

64. The method of claim 36 wherein the medical device comprises a suction line for communicating a suction from a source of negative pressure to the suction lumen.

65. The method of claim 36 wherein suction is created at a negative pressure between about 200 and about 600 mm Hg.

66. The method of claim 36 wherein the contact surface of the suction member comprises at least one suction port in communication with the suction lumen.

67. The method of claim 66 wherein the at least one suction port is cylindrical-shaped.

68. The method of claim 66 wherein the at least one suction port is cone-shaped.

69. The method of claim 66 wherein the at least one suction port is dome-shaped.

70. The method of claim 36 wherein the securing member includes a clamp for clamping to the operating table.

71. The method of claim 36 wherein the operating table includes a mounting rail.

72. The method of claim 71 wherein the securing member includes a clamp for clamping to the mounting rail.

73. A minimally invasive surgical method performed on a beating heart without creating an incision through the sternum of a patient and spreading apart the chest of the patient, the method comprising the following steps:

providing a first medical device having a tissue engaging member, a securing member and a remote actuator, the tissue engaging member having a contact surface adapted to engage tissue of the beating heart, the tissue engaging member having a suction lumen open to the atmosphere through the contact surface, the suction lumen adapted to be coupled to a suction source, wherein suction is communicated to the tissue of the beating heart to engage it, the tissue engaging member comprising one or more electrodes, the securing member coupled to the tissue engaging member, the securing member adapted to secure the tissue engaging member to an operating table, the remote actuator coupled to the tissue engaging member, the remote actuator adapted to move the tissue engaging member relative to the securing member within the chest of the patient, the remote actuator adapted for positioning the tissue engaging member from outside the chest of the patient;

providing a second medical device having a tissue engaging member, a securing member and a remote actuator, the tissue engaging member having a contact surface adapted to engage tissue of the beating heart, the securing member coupled to the tissue engaging member, the securing member adapted to secure the tissue engaging member to an operating table, the remote actuator coupled to the tissue engaging member, the remote actuator adapted to move the tissue engaging member relative to the securing member within the chest of the patient, the remote actuator adapted for positioning the tissue engaging member from outside the chest of the patient;

introducing the tissue engaging member of the first medical device into the chest of the patient;

moving the tissue engaging member of the first medical device within the chest of the patient to engage tissue of the beating heart;

securing the tissue engaging member of the first medical device to an operating table;

introducing the tissue engaging member of the second medical device into the chest of the patient;

moving the tissue engaging member of the second medical device within the chest of the patient to engage tissue of the beating heart; and securing the tissue engaging member of the second medical device to an operating table.

74. A minimally invasive surgical method of grasping tissue of a beating heart without creating an incision through the sternum of a patient and spreading apart the chest of the patient, the method comprising the following steps:

providing a medical device having a suction member, a securing member and a remote actuator, the suction member having a contact surface adapted to grasp tissue of the beating heart, the suction member having a suction lumen open to the atmosphere through the contact surface, the securing member coupled to the suction member, the securing member adapted to secure the suction member to an operating table, the securing member comprising at least one ball and socket joint, wherein the ball and socket securing member comprises a plurality of tube elements jointed together by a plurality of ball elements, the tube elements having socket ends shaped to mate with the ball elements, a cable disposed throughout the series of ball elements and tube elements and a locking actuator coupled to the cable, the locking actuator being capable of tightening the cable to lock the securing device into position, the remote actuator coupled to the suction member, the remote actuator adapted to move the suction member relative to the securing member within the chest of the patient, the remote actuator adapted for positioning the suction member from outside the chest of the patient;

creating a small incision or stab wound between the ribs of the patient to access the beating heart;

introducing the suction member into the chest of the patient through the small incision or stab wound;

moving the suction member within the chest of the patient so as to contact tissue of the beating heart;

creating suction in the suction lumen to grasp tissue of the beating heart; and, securing the suction member to an operating table.

75. The method of claim 74 further comprising the step of remotely actuating the locking actuator from a position outside the chest of the patient.

76. The method of claim 73 wherein the tissue engaging member of the second medical device includes a suction lumen open to the atmosphere through the contact surface of the second medical device.

77. The method of claim 76 further comprising the step of creating suction in the suction lumen of the second medical device to engage tissue of the beating heart.

78. The method of claim 73 further comprising the step of performing a surgical procedure on the beating heart.

79. The method of claim 78 wherein the surgical procedure is performing a coronary artery bypass graft.

80. The method of claim 79 wherein the coronary artery bypass graft procedure comprises grafting a mammary artery to a coronary artery.

81. The method of claim 73 further comprising the step of mobilizing an artery or vein.

82. The method of claim 81 wherein the step of mobilizing an artery or vein comprises mobilizing a mammary artery or saphenous vein.

83. The method of claim 73 further comprising the step of moving or repositioning the beating heart to achieve better access to an area of the beating heart which would otherwise be difficult to access.

84. The method of claim 83 wherein the step of moving or repositioning the beating heart to achieve better access to an area of the beating heart which would otherwise be difficult to access comprises moving or repositioning the beating heart to access the posterior or backside of the heart.

85. The method of claim 83 wherein the step of moving or repositioning the beating heart to achieve better access to an area of the beating heart which would otherwise be difficult to access comprises moving or repositioning the beating heart without significant deterioration of the pumping function of the beating heart.

86. The method of claim 73 further comprising the step of immobilizing an area of tissue on a beating heart.

87. The method of claim 73 further comprising the step of dispensing or removing a fluid in the chest of the patient, wherein the first or second medical device comprises a means for dispensing or removing the fluid.

88. The method of claim 73 further comprising the step of delivering light in the chest of the patient, wherein the first or second medical device comprises a means for delivering light.

89. The method of claim 73 further comprising the step of injecting a medicinal substance into the heart.

90. The method of claim 73 further comprising the step of at least partially collapsing at least one lung so as to provide an unencumbered area in which to manipulate at least one surgical instrument.

91. The method of claim 73 further comprising the step of using an endoscope.

92. The method of claim 73 wherein the securing member of the first medical device comprises at least one joint or hinge.

93. The method of claim 92 wherein the remote actuator of the first medical device actuates the at least one joint or hinge of the first medical device.

94. The method of claim 92 wherein the securing member of the second medical device comprises at least one joint or hinge.

95. The method of claim 94 wherein the remote actuator of the second medical device actuates the at least one joint or hinge of the second medical device.

96. The method of claim 73 wherein the remote actuator of the first medical device is capable of locking the position of the suction member of the first medical device relative to the securing member of the first medical device.

97. The method of claim 96 wherein the remote actuator of the second medical device is capable of locking the position of the suction member of the second medical device relative to the securing member of the second medical device.

98. The method of claim 73 wherein the securing member of the first medical device comprises an arm.

99. The method of claim 98 wherein the securing member of the second medical device comprises an arm.

100. The method of claim 73 wherein the securing member of the first medical device comprises at least one ball and socket joint.

101. The method of claim 100 wherein the securing member of the second medical device comprises at least one ball and socket joint.

102. The method of claim 73 wherein the securing member of the first or second medical device comprises a clamp.

103. The method of claim 73 wherein the securing member of the first or second medical device comprises a slip-grip type holder.

104. The method of claim 73 wherein the tissue engaging member of the first or second medical device comprises at least one paddle.

105. The method of claim 73 wherein the contact surface of the tissue engaging member of the first or second medical device conforms generally to the curvature of the beating heart.

106. The method of claim 73 wherein the securing member of the first medical device includes a clamp for clamping to the operating table.

107. The method of claim 106 wherein the securing member of the second medical device includes a clamp for clamping to the operating table.

108. The method of claim 73 wherein the operating table includes a mounting rail.

109. The method of claim 108 wherein the securing member of the first medical device includes a clamp for clamping to the mounting rail.

110. The method of claim 109 wherein the securing member of the second medical device includes a clamp for clamping to the mounting rail.

111. A minimally invasive surgical method performed on a beating heart without creating an incision through the sternum of a patient and spreading apart the chest of the patient, the method comprising the following steps:

providing a first medical device having a tissue engaging member, a securing member and a remote actuator, the tissue engaging member having a contact surface adapted to engage tissue of the beating heart, the securing member coupled to the tissue engaging member, the securing member adapted to secure the tissue engaging member to an operating table, the securing member comprising an arm, the arm having a proximal end and a distal end, the arm comprising:

a plurality of links, the links being free to move relative to one another so that the arm articulates; and, a cable extending through the links, the remote actuator coupled to the tissue engaging member, the remote actuator adapted to move the tissue engaging member relative to the securing member within the chest of the patient, the remote actuator adapted for positioning the tissue engaging member from outside the chest of the patient;

providing a second medical device having a tissue engaging member, a securing member and a remote actuator, the tissue engaging member having a contact surface adapted to engage tissue of the beating heart, the securing member coupled to the tissue engaging member, the securing member adapted to secure the tissue engaging member to an operating table, the remote actuator coupled to the tissue engaging member, the remote actuator adapted to move the tissue engaging member relative to the securing member within the chest of the patient, the remote actuator adapted for positioning the tissue engaging member from outside the chest of the patient;

introducing the tissue engaging member of the first medical device into the chest of the patient;

moving the tissue engaging member of the first medical device within the chest of the patient to engage tissue of the beating heart;

securing the tissue engaging member of the first medical device to an operating table;

introducing the tissue engaging member of the second medical device into the chest of the patient;

moving the tissue engaging member of the second medical device within the chest of the patient to engage tissue of the beating heart; and securing the tissue engaging member of the second medical device to an operating table.

112. The method of claim 111 wherein the securing member of the first medical device further comprises a locking actuator coupled to one end of the cable and one end of the arm to tension the cable thereby locking the links relative to one another so that the arm changes from an articulating condition to a locked rigid condition.

113. The method of claim 111 wherein the securing member of the second medical device comprises an arm, the arm having a proximal end and a distal end, the arm comprising:

a plurality of links, the links being free to move relative to one another so that the arm articulates; and, a cable extending through the links.

114. The method of claim 113 wherein the securing member of the second medical device further comprises a locking actuator coupled to one end of the cable of the second medical device and one end of the arm of the second medical device to tension the cable of the second medical device thereby locking the links of the second medical device relative to one another so that the arm of the second medical device changes from an articulating condition to a locked rigid condition.

* * * * *